(12) United States Patent
Yoon et al.

(10) Patent No.: US 11,342,505 B2
(45) Date of Patent: May 24, 2022

(54) ORGANIC COMPOUNDS AND ORGANIC ELECTROLUMINESCENT DEVICE INCLUDING THE SAME

(71) Applicants: LG Display Co., Ltd., Seoul (KR); Material Science Co., Ltd., Seoul (KR)

(72) Inventors: Seunghee Yoon, Seoul (KR); Inbum Song, Seoul (KR); Hyun Bin Kang, Suwon-si (KR); Jaemin Ryu, Bucheon-si (KR); Jin Sung Kim, Anyang-si (KR); Tae-Ho Kwak, Goyang-si (KR); Sunghoon Kim, Seoul (KR)

(73) Assignees: MATERIAL SCIENCE CO., LTD., Seoul (KR); LG DISPLAY CO., LTD., Seoul (KR)

( * ) Notice: Subject to any disclaimer, the term of this patent is extended or adjusted under 35 U.S.C. 154(b) by 160 days.

(21) Appl. No.: 16/366,975

(22) Filed: Mar. 27, 2019

(65) Prior Publication Data
US 2019/0305227 A1    Oct. 3, 2019

(30) Foreign Application Priority Data

Mar. 28, 2018  (KR) .................. 10-2018-0036167
Aug. 24, 2018  (KR) .................. 10-2018-0099515

(51) Int. Cl.
*C07D 307/77*    (2006.01)
*H01L 51/00*     (2006.01)
*C09K 11/06*     (2006.01)
(Continued)

(52) U.S. Cl.
CPC ........ *H01L 51/0058* (2013.01); *C07D 307/77* (2013.01); *C07D 307/91* (2013.01);
(Continued)

(58) Field of Classification Search
None
See application file for complete search history.

(56) References Cited

U.S. PATENT DOCUMENTS

| 2011/0037057 | A1* | 2/2011 | LeCloux | C07D 307/87 257/40 |
| 2014/0001459 | A1* | 1/2014 | Gao | H01L 51/0052 257/40 |

(Continued)

FOREIGN PATENT DOCUMENTS

| KR | 20090086015 A * | 8/2009 | .............. C07C 15/28 |
| KR | 10-2013-0010633 A | 1/2013 | |

(Continued)

OTHER PUBLICATIONS

Machine translation of KR-20090086015, translation generated Nov. 2020, 23 pages. (Year: 2020).*

(Continued)

*Primary Examiner* — Robert S Loewe
(74) *Attorney, Agent, or Firm* — Seed IP Law Group LLP

(57) ABSTRACT

The present disclosure relates to a novel organic compound and an organic electroluminescent device including the same. More specifically, the present disclosure relates to a deuterated organic compound and an organic electroluminescent device including at least one organic layer made of the deuterated organic compound. Thus, the organic electroluminescent device exhibits a longer lifetime, lower voltage implementation, and improved luminous efficiency.

6 Claims, 3 Drawing Sheets

(51) Int. Cl.
    *C07D 333/76*     (2006.01)
    *C07D 409/10*     (2006.01)
    *C07D 307/91*     (2006.01)
    *H01L 51/50*     (2006.01)

(52) U.S. Cl.
    CPC ......... *C07D 333/76* (2013.01); *C07D 409/10* (2013.01); *C09K 11/06* (2013.01); *H01L 51/0052* (2013.01); *H01L 51/0073* (2013.01); *H01L 51/0074* (2013.01); *C09K 2211/1018* (2013.01); *H01L 51/504* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5096* (2013.01)

(56) References Cited

U.S. PATENT DOCUMENTS

| | | | | |
|---|---|---|---|---|
| 2014/0034943 | A1* | 2/2014 | Mizuki | C07D 209/88 257/40 |
| 2015/0041792 | A1* | 2/2015 | Suzuki | H01L 27/3211 257/40 |
| 2015/0357579 | A1* | 12/2015 | Itoi | C07F 7/0812 257/40 |
| 2015/0357580 | A1* | 12/2015 | Itoi | H01L 51/0072 257/40 |
| 2016/0111653 | A1* | 4/2016 | Itoi | H01L 51/0061 257/40 |
| 2016/0141361 | A1 | 5/2016 | Wang et al. | |
| 2016/0155952 | A1* | 6/2016 | Hwang | C09K 11/06 257/40 |
| 2016/0190467 | A1* | 6/2016 | Jang | H01L 51/0073 257/40 |
| 2016/0351817 | A1* | 12/2016 | Kim | H01L 51/0052 |
| 2017/0010724 | A1 | 1/2017 | Cao et al. | |
| 2017/0018723 | A1* | 1/2017 | Cha | C07D 307/94 |
| 2017/0025608 | A1* | 1/2017 | Herron | C09K 11/06 |
| 2017/0133604 | A1* | 5/2017 | Lee | C07D 493/04 |
| 2017/0155049 | A1* | 6/2017 | Kim | H01L 51/0052 |
| 2017/0213969 | A1* | 7/2017 | Shin | H01L 51/0055 |
| 2018/0009776 | A1* | 1/2018 | Cha | C07C 13/567 |
| 2018/0182971 | A1* | 6/2018 | Park | H01L 51/0073 |
| 2018/0233669 | A1* | 8/2018 | Lee | C09K 11/06 |
| 2018/0269419 | A1* | 9/2018 | Tu | H01L 51/5221 |
| 2018/0277772 | A1* | 9/2018 | Wu | H01L 51/56 |
| 2019/0198766 | A1* | 6/2019 | Suh | H01L 51/5012 |
| 2019/0296243 | A1* | 9/2019 | Suh | H01L 51/0072 |
| 2020/0111972 | A1* | 4/2020 | Nakano | C09K 11/06 |

FOREIGN PATENT DOCUMENTS

| | | | | |
|---|---|---|---|---|
| KR | 10-1368164 | B1 | 2/2014 | |
| KR | 10-2014-0039187 | A | 4/2014 | |
| KR | 10-2016-0089693 | A | 7/2016 | |
| KR | 10-2016-0090443 | A | 8/2016 | |
| KR | 10-2016-0107669 | A | 9/2016 | |
| KR | 10-2016-0141361 | A | 12/2016 | |
| KR | 10-2017-0009714 | A | 1/2017 | |
| KR | 10-2017-0010724 | A | 2/2017 | |
| WO | WO-2018120369 | A1 * | 7/2018 | ......... H01L 27/3209 |

OTHER PUBLICATIONS

Tang et al. "Organic Electroluminescent Diodes," *Applied Physics Letters*, 51:913, 1987.

* cited by examiner

[FIG. 1]
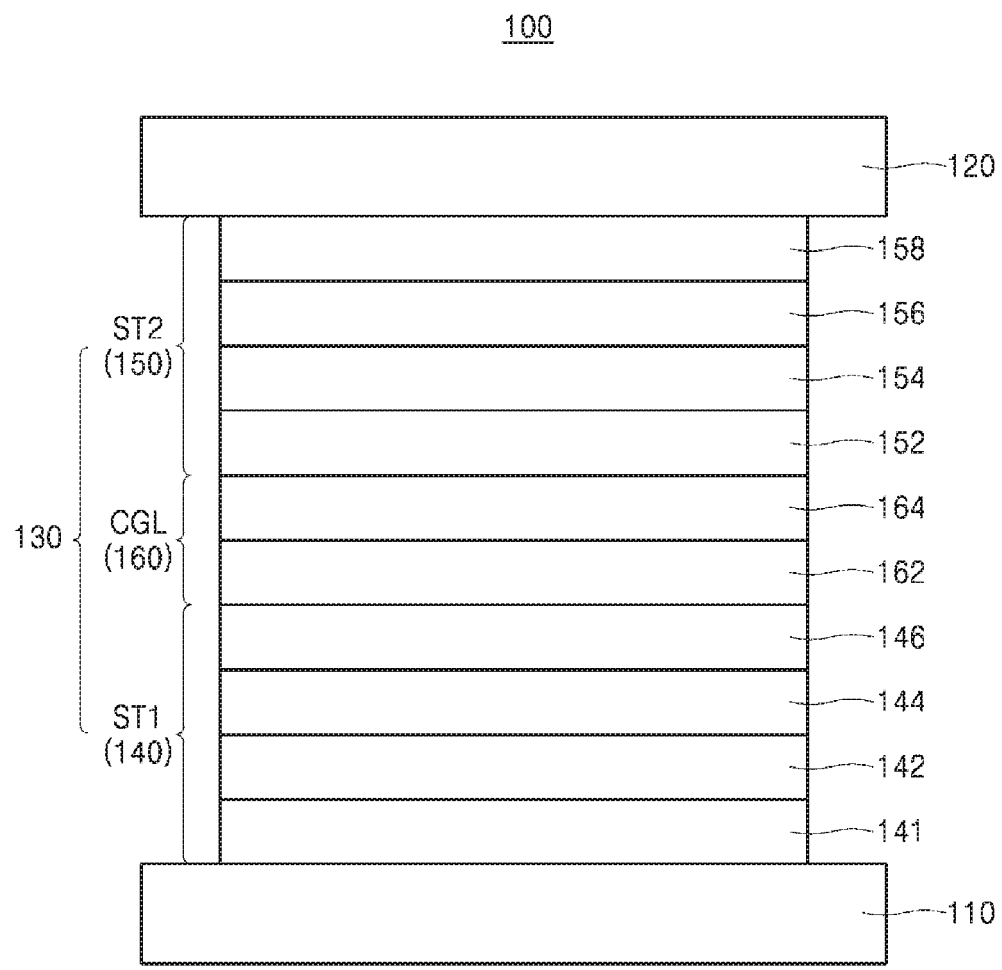

[FIG. 2]
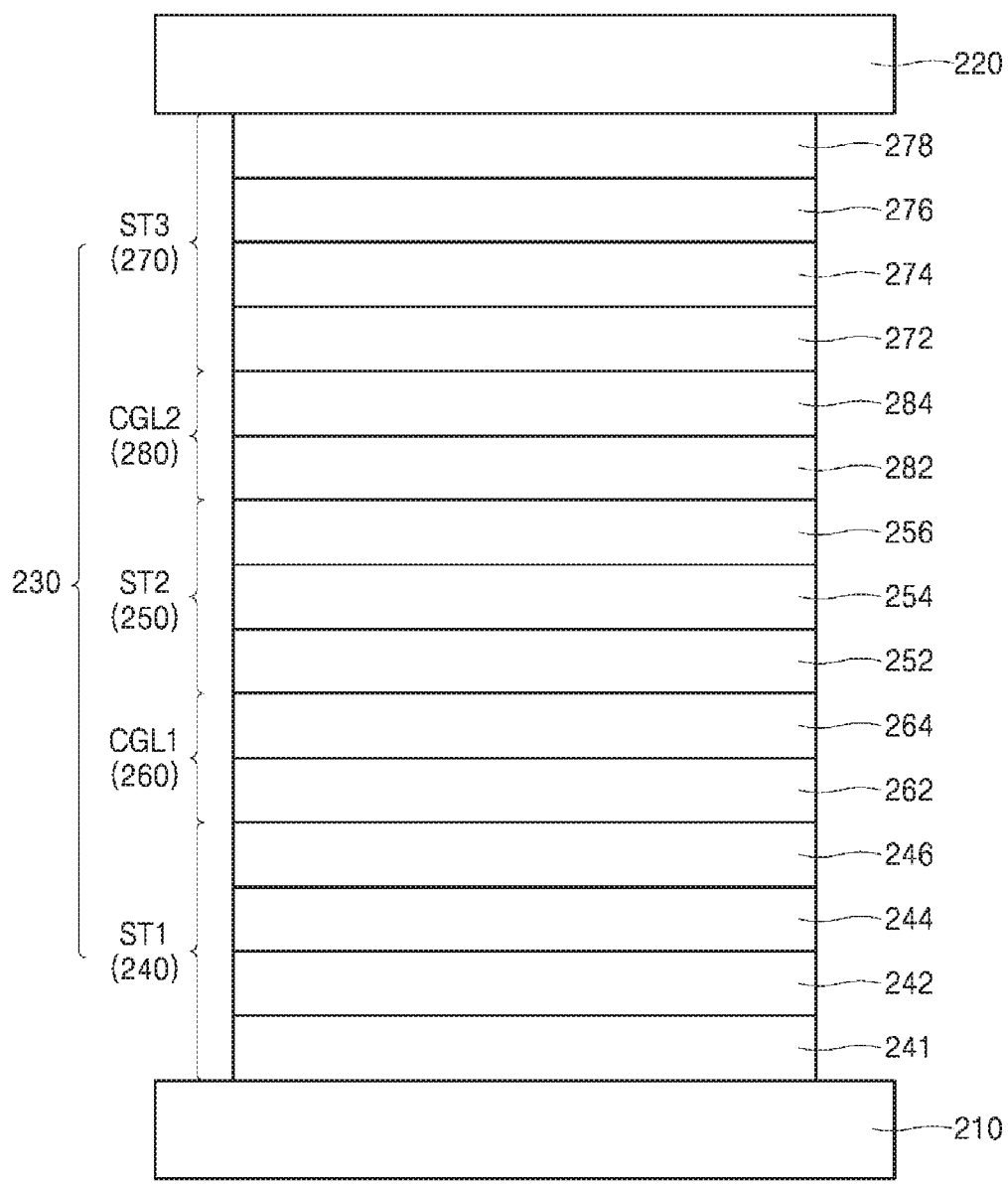

[FIG. 3]
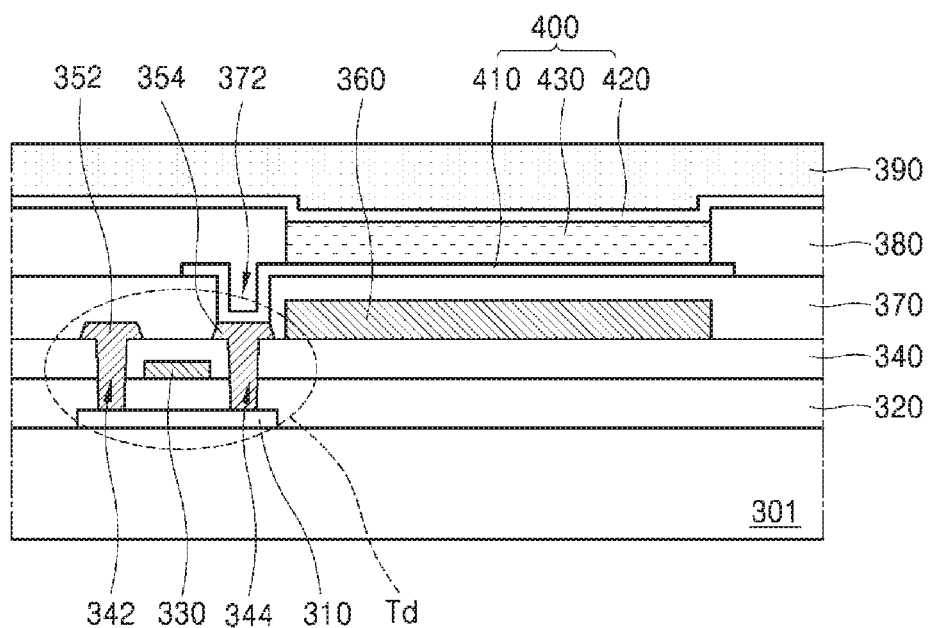

ORGANIC COMPOUNDS AND ORGANIC ELECTROLUMINESCENT DEVICE INCLUDING THE SAME

CROSS-REFERENCE TO RELATED APPLICATIONS

This application claims the priority of Korean Patent Application Nos. 10-2018-0036167 filed on Mar. 28, 2018, and 10-2018-0099515 filed on Aug. 24, 2018, in the Korean Intellectual Property Office, the disclosure of which is hereby incorporated by reference in its entirety.

BACKGROUND

Technical Field

The present disclosure relates to a novel organic compound and an organic electroluminescent device including the same. More specifically, the present disclosure relates to a deuterated organic compound and an organic electroluminescent device including at least one organic layer made of the deuterated organic compound.

Description of the Related Art

An organic electroluminescent device has a simpler structure than those of other flat panel display devices such as a liquid crystal display (LCD), a plasma display panel (PDP), and a field emission display (FED). The organic electroluminescent device has various advantages in a manufacturing process, has excellent luminance and viewing angle characteristics, and a high response speed and a low driving voltage. Thus, the organic electroluminescent device is being actively developed so as to be used for a flat panel display such as a wall-hanging TV or as a light source such as a backlight of a display, a illumination device, and a billboard.

Generally, in the organic electroluminescent device, when a voltage is applied thereto, holes injected from a anode and electrons injected from a cathode are recombined with each other to form excitons as electron-hole pairs. Then, energy of the excitons is transmitted to a light emitting material to emit light beams.

C. W. Tang reported a low voltage-driven organic electroluminescent device including an organic thin film stack formed between two opposing electrodes to improve efficiency and stability of the organic electroluminescent device (C. W. Tang, S. A. Vanslyke, Applied Physics Letters, vol. 51, p. 913, 1987). Subsequently, researches on organic materials for the organic electroluminescent device having the organic thin film stack have been actively conducted.

Generally, the organic electroluminescent device has a structure including a cathode (electron injection electrode), a anode (hole injection electrode), and at least one organic layer between the two electrodes.

Most of organic materials used in the organic electroluminescent device are pure organic materials or coordination complexes between organic materials and metals. The organic materials used in the organic electroluminescent device may be classified into a hole-injecting material, a hole-transporting material, a light-emitting material, an electron-transporting material, and an electron-injecting material. In this connection, the hole-injecting materials or hole-transporting materials may mainly employ organic materials which are easily oxidized and which are electrochemically stable in the oxidized state. The electron-injecting materials and electron-transporting materials may mainly employ organic materials that are easily reduced and electrochemically stable in the reduced state.

The light-emitting layer material preferably employs a material electrochemically stable in both the oxidized and reduced states. Further, the light-emitting layer material preferably employs a material having high efficiency of light emission in which excitons are applied thereto to emit light beams. In the light-emitting layer made of the materials having such properties, electrons recombines with holes to create an excited state. When the excited state returns to a ground state, the light emission may occur. The compound type of each organic layer ultimately affects characteristics and implementations of the organic electroluminescent device.

Recently, the organic electroluminescent device requires a longer lifetime, lower voltage implementation, and improved luminous efficiency. Those requirements may lead to the lower power consumption and improved durability of the device.

To this end, the present inventors attempted to achieve the low voltage implementation and improved lifetime using deuterated anthracene organic compounds including polar molecules.

PRIOR ART DOCUMENT

[Patent Literature] Korean Patent Application Publication No. 10-2013-0010633; Korean Patent No. 10-1368164

BRIEF SUMMARY

One purpose of the present disclosure is to provide a novel compound that may be employed as a blue host material for a light-emitting layer.

Another purpose of the present disclosure is to provide an organic electroluminescent device in which the device includes the novel compound containing polar molecules to allow a driving voltage to be lower and in which the device includes a deuterated anthracene organic compound to realize the increased lifetime, and excellent luminescence efficiency and external quantum efficiency (EQE) characteristics.

The purposes of the present disclosure are not limited to the above-mentioned purposes. Other purposes and advantages of the present disclosure, as not mentioned above, may be understood from the following descriptions and more clearly understood from the embodiments of the present disclosure. Further, it will be readily appreciated that the objects and advantages of the present disclosure may be realized by features and combinations thereof as disclosed in the claims.

In a first aspect of the present disclosure, there is provided a compound represented by a following Chemical Formula 1:

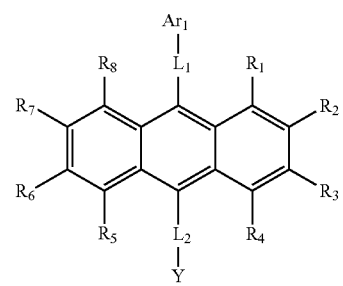

Chemical Formula 1 wherein Y denotes a substituent represented by a following Chemical Formula 2:

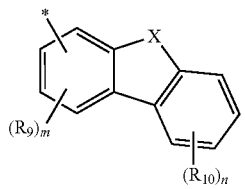

Chemical Formula 2 wherein X is O or S,
n is an integer of 0 to 4,
m is an integer of 0 to 3,
wherein $L_1$ and $L_2$ are the same or different from each other, and each of $L_1$ and $L_2$ independently are selected from a group consisting of a direct bond, a substituted or unsubstituted arylene group having 6 to 30 carbon atoms, a substituted or unsubstituted heteroarylene group having 6 to 30 ring constituting atoms, a substituted or unsubstituted alkylene group having 2 to 10 carbon atoms, a substituted or unsubstituted cycloalkylene group having 2 to 10 carbon atoms, a substituted or unsubstituted alkenylene group having 2 to 10 carbon atoms, a substituted or unsubstituted cycloalkenylene group having 2 to 10 carbon atoms, a substituted or unsubstituted heteroalkylene group having 2 to 10 carbon atoms, a substituted or unsubstituted heterocycloalkylene group having 2 to 10 carbon atoms, a substituted or unsubstituted heteroalkenylene group having 2 to 10 carbon atoms, and a substituted or unsubstituted heterocycloalkenylene group having 2 to 10 carbon atoms, wherein $Ar_1$ is selected from a group consisting of a substituted or unsubstituted aryl group having 6 to 30 carbon atoms, a substituted or unsubstituted heteroaryl group having 3 to 30 carbon atoms, a substituted or unsubstituted alkyl group having 1 to 20 carbon atoms, a substituted or unsubstituted cycloalkyl group having 1 to 20 carbon atoms, a substituted or unsubstituted heteroalkyl group having 1 to 20 carbon atoms, a substituted or unsubstituted heterocycloalkyl group having 1 to 20 carbon atoms, a substituted or unsubstituted alkenyl group having 1 to 20 carbon atoms, a substituted or unsubstituted cycloalkenyl group having 1 to 20 carbon atoms, and a substituted or unsubstituted heteroalkenyl group having 1 to 20 carbon atoms, wherein $R_1$, $R_2$, $R_3$, $R_4$, $R_5$, $R_6$, $R_7$, $R_8$, $R_9$, and $R_{10}$ are, at each occurrence, independently selected from a group consisting of hydrogen, deuterium, a substituted or unsubstituted alkyl group having 1 to 30 carbon atoms, a substituted or unsubstituted cycloalkyl group having 3 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, and a substituted or unsubstituted heteroarylalkyl group having 3 to 30 carbon atoms, or wherein each occurrence of $R_9$ may, together with the carbon to which it is attached, join with an adjacent $R_9$ to form a ring, or wherein each occurrence of $R_{10}$ may, together with the carbon to which it is attached, join with an adjacent $R_{10}$ to form a ring, wherein each of $R_1$, $R_2$, $R_3$, $R_4$, $R_5$, $R_6$, $R_7$, $R_8$, $R_9$, $R_{10}$, $L_1$, $L_2$, and $Ar_1$ is independently substituted with at least one substituent selected from a group consisting of hydrogen, deuterium, a cyano group, a nitro group, a halogen group, a hydroxy group, a substituted or unsubstituted alkyl having 1 to 30 carbon atoms, a substituted or unsubstituted cycloalkyl group having 3 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or a heteroaryl group having 2 to 30 carbon atoms, a substituted or unsubstituted heteroarylalkyl group having 3 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl group having 6 to 30 carbon atoms, and a substituted or unsubstituted aryloxy group having 6 to 30 carbon atoms, and wherein at least one of substituents of $L_1$, $L_2$, $Ar_1$, $R_1$, $R_2$, $R_3$, $R_4$, $R_5$, $R_6$, $R_7$, $R_8$, $R_9$, or $R_{10}$ includes deuterium.

Further, according to the present disclosure, at least one of $R_1$, $R_2$, $R_3$, $R_4$, $R_5$, $R_6$, $R_7$, or $R_8$ preferably includes deuterium.

Furthermore, according to the present disclosure, $L_1$ preferably is one selected from a group consisting of a direct bond, a substituted or unsubstituted arylene group having 6 to 30 carbon atoms, and a substituted or unsubstituted heteroarylene group having 6 to 30 ring constituting atoms. $L_2$ preferably is a direct bond or substituted or unsubstituted phenylene group. More preferably, $L_1$ is a direct bond or a substituted or unsubstituted arylene group having 6 to 30 carbon atoms.

According to one preferred implementation of the present disclosure, there is provided an organic electroluminescent device including a first electrode; a second electrode facing away the first electrode; and at least one organic layer interposed between the first electrode and the second electrode, wherein the at least one organic layer contains one or more compounds of the Chemical Formula 1.

Further, the organic layer according to the present disclosure defines one selected from a group consisting of a hole-injecting layer, a hole-transporting layer, an electron-blocking layer, a light-emitting layer, a hole-blocking layer, an electron-transporting layer and an electron-injecting layer.

Furthermore, the organic layer in accordance with the present disclosure defines a light-emitting layer, wherein the light-emitting layer contains a compound of the Chemical Formula 1 as a host material.

The organic electroluminescent device may include a vertical stack of a anode, a hole-injecting layer HIL), a hole-transporting layer HTL), a light-emitting layer EML), an electron-transporting layer ETL) and an electron-injecting layer EIL) in this order. The device may further include an electron-blocking layer (EBL) and a hole-blocking layer (HBL) to enhance the light-emitting efficiency of the light-emitting layer, wherein the electron-blocking layer (EBL) and hole-blocking layer (HBL) sandwich the light-emitting layer (EML) therebetween.

Specifically, the organic electroluminescent device may further include an additional organic layer between the first electrode and the light-emitting layer or between the light-emitting layer and the second electrode, wherein the additional organic layer defines at least one selected from a group consisting of a hole-injecting layer, a hole-transporting layer, an electron-blocking layer, a light-emitting layer, a hole-blocking layer, an electron-transporting layer and an electron-injecting layer.

Further, when the device is embodied as a tandem organic electroluminescent device, a single light emission unit may be composed of a stack of at least two light emission layers and a charge generation layer (CGL) therebetween. The organic electroluminescent device may include two or more stacks on a substrate, wherein each stack include a vertical stack of a first electrode and a second electrode facing away each other, and a light-emitting layer disposed between the first and second electrodes to emit a specific light beam. The light-emitting layer coupled to a charge-generating layer (CGL) composed of an N-type charge-generating layer and a P-type charge-generating layer may render blue, yellow or green or red.

In one implementation of the present disclosure, there is provide an organic electroluminescent device including a first light emission sub-stack for rendering first color light, and a second light emission sub-stack stacked on the first light emission sub-stack for rendering second color light, wherein at least one of the first light emission sub-stack and the second light emission sub-stack contains a host material, wherein the host material includes a compound represented by a following Chemical Formula 1:

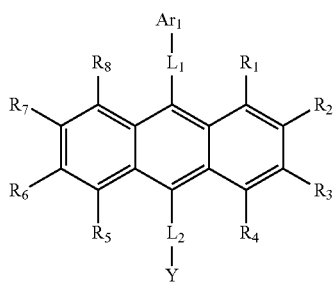

Chemical Formula 1 wherein Y denotes a substituent represented by a following Chemical Formula 2:

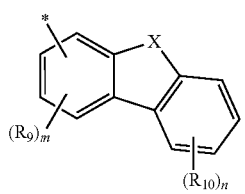

Chemical Formula 2 wherein X is O or S,
n is an integer of 0 to 4,
m is an integer of 0 to 3,
wherein $L_1$ and $L_2$ are the same or different from each other, and each of $L_1$ and $L_2$ independently are selected from a group consisting of a direct bond, a substituted or unsubstituted arylene group having 6 to 30 carbon atoms, a substituted or unsubstituted heteroarylene group having 6 to 30 ring constituting atoms, a substituted or unsubstituted alkylene group having 2 to 10 carbon atoms, a substituted or unsubstituted cycloalkylene group having 2 to 10 carbon atoms, a substituted or unsubstituted alkenylene group having 2 to 10 carbon atoms, a substituted or unsubstituted cycloalkenylene group having 2 to 10 carbon atoms, a substituted or unsubstituted heteroalkylene group having 2 to 10 carbon atoms, a substituted or unsubstituted heterocycloalkylene group having 2 to 10 carbon atoms, a substituted or unsubstituted heteroalkenylene group having 2 to 10 carbon atoms, and a substituted or unsubstituted heterocycloalkenylene group having 2 to 10 carbon atoms, wherein $Ar_1$ is one selected from a group consisting of a substituted or unsubstituted aryl group having 6 to 30 carbon atoms, a substituted or unsubstituted heteroaryl group having 3 to 30 carbon atoms, a substituted or unsubstituted alkyl group having 1 to 20 carbon atoms, a substituted or unsubstituted cycloalkyl group having 1 to 20 carbon atoms, a substituted or unsubstituted heteroalkyl group having 1 to 20 carbon atoms, a substituted or unsubstituted heterocycloalkyl group having 1 to 20 carbon atoms, a substituted or unsubstituted alkenyl group having 1 to 20 carbon atoms, a substituted or unsubstituted cycloalkenyl group having 1 to 20 carbon atoms, and a substituted or unsubstituted heteroalkenyl group having 1 to 20 carbon atoms, wherein $R_1$, $R_2$, $R_3$, $R_4$, $R_5$, $R_6$, $R_7$, $R_8$, $R_9$, and $R_{10}$ are, at each occurrence, independently selected from a group consisting of hydrogen, deuterium, a substituted or unsubstituted alkyl group having 1 to 30 carbon atoms, a substituted or unsubstituted cycloalkyl group having 3 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or unsubstituted heteroaryl group having 2 to 30 carbon atoms, and a substituted or unsubstituted heteroarylalkyl group having 3 to 30 carbon atoms, or wherein each occurrence of $R_9$ may, together with the carbon to which it is attached, join with an adjacent $R_9$ to form a ring, or wherein each occurrence of $R_{10}$ may, together with the carbon to which it is attached, join with an adjacent $R_{10}$ to form a ring, wherein each of $R_1$, $R_2$, $R_3$, $R_4$, $R_5$, $R_6$, $R_7$, $R_8$, $R_9$, $R_{10}$, $L_1$, $L_2$, and $Ar_1$ is independently substituted with at least one substituent selected from a group consisting of hydrogen, deuterium, a cyano group, a nitro group, a halogen group, a hydroxy group, a substituted or unsubstituted alkyl having 1 to 30 carbon atoms, a substituted or unsubstituted cycloalkyl group having 3 to 30 carbon atoms, a substituted or unsubstituted alkenyl group having 2 to 30 carbon atoms, a substituted or unsubstituted alkynyl group having 2 to 24 carbon atoms, a substituted or unsubstituted heteroalkyl group having 2 to 30 carbon atoms, a substituted or unsubstituted aralkyl group having 7 to 30 carbon atoms, a substituted or unsubstituted aryl group having 6 to 30 carbon atoms, a substituted or a heteroaryl group having 2 to 30 carbon atoms, a substituted or unsubstituted heteroarylalkyl group having 3 to 30 carbon atoms, a substituted or unsubstituted alkoxy group having 1 to 30 carbon atoms, a substituted or unsubstituted alkylamino group having 1 to 30 carbon atoms, a substituted or unsubstituted arylamino group having 6 to 30 carbon atoms, a substituted or unsubstituted aralkylamino group having 6 to 30 carbon atoms, a substituted or unsubstituted heteroarylamino group having 2 to 24 carbon atoms, a substituted or unsubstituted alkylsilyl group having 1 to 30 carbon atoms, a substituted or unsubstituted arylsilyl group having 6 to 30 carbon atoms, and a substituted or unsubstituted aryloxy group having 6 to 30 carbon atoms, and wherein at least one of $L_1$, $L_2$, $Ar_1$, $R_1$, $R_2$, $R_3$, $R_4$, $R_5$, $R_6$, $R_7$, $R_8$, $R_9$, or $R_{10}$ includes deuterium.

Details of the compounds represented by the Chemical Formula 1 are as described above.

In one implementation, the first light emission sub-stack includes a vertical stack of a first electrode, a first hole-transporting layer, a first light-emitting layer, and a first electron-transporting layer in this order. The second light emission sub-stack includes a vertical stack of a second hole-transporting layer, a second light-emitting layer and a second electron-transporting layer in this order. At least one of the first light-emitting layer and the second light-emitting layer may contain the host material.

FIG. 1 is a schematic cross-sectional view of a tandem organic electroluminescent device having two light emission sub-stacks according to an exemplary first embodiment of the present disclosure. As shown in FIG. 1, the organic electroluminescent device 100 according to the first embodiment of the present disclosure has a first electrode 110 and a second electrode 120 facing away each other, and an organic light-emitting stack 130 positioned between the first electrode 110 and the second electrode 120. The organic light-emitting stack 130 includes a first light emission sub-stack (ST1) 140 located between the first electrode 110 and the second electrode 120 and containing a first light-emitting layer 144; a second light emission sub-stack (ST2) 150 located between the first light emission sub-stack 140 and the second electrode 120 and containing a second light-emitting layer 154; and a charge-generating layer (CGL) 160 disposed between the first and second light emission sub-stacks 140 and 150.

The first electrode 120 acts as an anode for injecting holes. The first electrode 120 may be made of a conductive material with a high work function, for example, indium-tin-oxide (ITO), indium-zinc-oxide (IZO), and zinc-oxide (ZnO). The second electrode 120 acts as a cathode for injecting electrons. The second electrode 120 may be made of a conductive material having a low work function, for example, aluminum (Al), magnesium (Mg), and aluminum-magnesium alloy (AlMg).

The first light emission sub-stack 140 includes a vertical stack of a hole-injecting layer 141 located between the first electrode 110 and first light-emitting layer 144, a first hole-transporting layer 142 located between the hole-injecting layer 141 and the first light-emitting layer 144, and a first electron-transporting layer 146 located between first light-emitting layer 144 and charge-generating layer 160.

The hole-injecting layer 141 improves properties of an interface between the inorganic first electrode 120 and the first hole-transporting layer 142 as an organic layer. The hole-injecting layer 141 may contain a compound represented by the Chemical Formula 1 described above. In one example, the hole-injecting layer 141 may contain at least one selected from a group consisting of 4,4',4"-tris(3-methylphenylphenylamino)triphenylamine (MTDATA), copper phthalocyanine (CuPc), Tris(4-carbazoyl-9-yl-phenyl)amine (TCTA), N,N'-diphenyl-N,N'-bis(1-naphthyl)-1,1'-biphenyl-4,4"-diamine (NPB; NPD), 1,4,5,8,9,11-hexaazatriphenylenehexacarbonitrile (HATCN), 1,3,5-tris[4-(diphenylamino)phenyl]benzene (TDAPB), poly(3,4-ethylenedioxythiophene)polystyrene sulfonate (PEDOT/PSS), 2,3,5,6-tetrafluoro-7,7,8,8-tetracyanoquinodimethane (F4-TCNQ), and/or N-(biphenyl-4-yl)-9,9-dimethyl-N-(4-(9-phenyl-9H-carbazol-3-yl)phenyl)-9H-fluoren-2-amine.

In one example, a thickness of the hole-injecting layer 141 may be in a range of 1 to 150 nm. When the thickness of the hole-injecting layer 141 is greater than or equal to 1 nm, the hole injection characteristics may be improved. When the thickness is 150 nm or smaller, a problem of an increase in the driving voltage due to an increase in the thickness of the hole-injecting layer 141 may be prevented. The hole-injecting layer 141 may be omitted depending on a structure and properties of the organic electroluminescent device.

The first hole-transporting layer 142 is located between the hole-injecting layer 141 and the first light-emitting layer 144. The first light-emitting layer 144 is located between the first hole-transporting layer 142 and the first electron-transporting layer 146. The first electron-transporting layer 146 is located between the first light-emitting layer 144 and the charge-generating layer 160.

The second light emission sub-stack 150 includes a vertical stack of a second hole-transporting layer 152, a second light-emitting layer 154, a second electron-transporting layer 156, and an electron-injecting layer 158 in this order. The second hole-transporting layer 152 is located between the charge-generating layer 160 and the second light-emitting layer 154. The second light-emitting layer 154 is located between the second hole-transporting layer 152 and the second electrode 120. Further, the second electron-transporting layer 156 is located between the second light-emitting layer 154 and the second electrode 120. The electron-injecting layer 158 is located between the second electron-transporting layer 156 and the second electrode 120.

Each of the first and second hole-transporting layers 142 and 152 may contain a compound represented by the Chemical Formula 1 as described above. In one example, Each of the first and second hole-transporting layers 142 and 152 may contain at least one selected from a group consisting of N,N'-diphenyl-N,N'-bis(3-methylphenyl)-1,1'-biphenyl-4,4'-diamine (TPD), NPD, MTDATA, 1,3-bis(N-carbazolyl)benzene (mCP), CuPC, TCTA, tris(trifluorovinyl ether)-tris(4-carbazoyl-9-yl-phenyl)amine (TFV-TCTA), tris[4-(diethylamino)phenyl]amine, N-(biphenyl-4-yl)-9,9-dimethyl-N-(4-(9-phenyl-9H-carbazol-3-yl)phenyl)-9H-fluorene-2-amine, tri-p-tolylamine, N-[1,1'-biphenyl]-4-yl-9,9-diMethyl-N-[4-(9-phenyl-9H-carbazol-3-yl)phenyl]-amine), 4,4'-bis(N-carbazolyl)-1,1'-biphenyl; CBP) and/or 1,1-bis(4-(N,N'-di(ptolyl)amino)phenyl)cyclohexane (TAPC).

Each of the first hole-transporting layer 142 and the second hole-transporting layer 152 may have a thickness of 1 to 150 nm. In this connection, when the thickness of each of the first and second hole-transporting layers 142 and 152 is 1 nm or greater, the hole transporting property may be improved. When the thickness is 150 nm or smaller, the problem of the increase in a driving voltage due to an increase in the thickness of each of the first and second hole-transporting layers 142 and 152 may be prevented. The first hole-transporting layer 142 and the second hole-transporting layer 152 may be made of the same material or may be made of different materials.

In one exemplary embodiment, each of the first and second light-emitting layers 144, 154 may contain a host and dopants doped into the host. The first and second light-emitting layers 144, 154 may render different colors. The dopant material may be added in a content of about 1 to 30% by weight based on a weight of the host material.

In one example, the first light-emitting layer 144 may render blue (B), red (R), green (G) or yellow (Y). When the first light-emitting layer 144 renders blue (B), the layer 144 includes one of a blue light-emitting material layer or a dark blue light-emitting material layer or sky blue light-emitting material layer. Alternatively, when the first light-emitting layer 144 may be composed of a combination (BR) of a blue light-emitting material layer and a red light-emitting material layer, a combination (BYG) of a blue light-emitting material layer and a yellow-green (YG) light-emitting material layer, or a combination (BG) of a blue light-emitting material layer and a green light-emitting material layer.

In one example, the second light-emitting layer 154 may render red (R), green (G), blue (B), or yellow green (YG). In one exemplary embodiment, the first light-emitting layer 144 may render blue, while the second light-emitting layer 154 may render green (G), yellow-green (YG), yellow (Y) or orange (O) having a longer wavelength than blue.

In one example, when the first light-emitting layer 144 emits blue light, the first light-emitting layer 134 may contain at least one fluorescent host material selected from a group consisting of anthracene and its derivatives, pyrene and its derivatives, and the compound represented by the Chemical Formula 1, and fluorescence dopants doped into the host material.

In one example, the blue light-emitting host material employed for the first light-emitting layer 144 may include at least one selected from a group consisting of 4,4'-bis(2, 2'-diphenylyinyl)-1,1'-biphenyl (DPVBi), 9,10-di-(2-naphtyl)anthracene (ADN), 2,5,8,11-(tetra-t-butylperylene (TBADN), 2-tert-butyl-9,10-di(2-naphthyl)anthracene, 2-methyl-9,10-di(2-naphtyl)anthracene (MADN), and/or 2,2',2''-(1,3,5-benzinetriyl)-tris(1-phenyl-1-H-benzimidazole (TBPi).

Details of the compounds represented by the Chemical Formula 1 are as described above.

Further, the blue light dopant material employed for the first light-emitting layer 144 may include at least one selected from a group consisting of 4,4'-bis(9-ethyl-3-carbazovinylene)-1,1'-biphenyl (BCzVBi) and/or diphenyl-[4-(2-[1,1;4,1]terphenyl-4-yl-vinyl)-phenyl]-amine (BD-1), spiro-DPVBi, spiro-CBP, distyrylbenzene (DSB) and its derivatives, distyryl arylene (DSA) and its derivatives, polyfluoorene (PF)-based polymer, and polyphenylene vinylene (PPV)-based polymer. Alternatively, the blue dopant may include a phosphorescent dopant as an iridium-based dopant. In this connection, the first light-emitting layer 144 may include a sky blue light-emitting material layer or a deep blue light-emitting material layer. In this connection, an emission wavelength from the first light emission sub-stack (144) may be in a range of 440 nm to 480 nm.

In one example, when the first light-emitting layer 144 is embodied as a green (G) light-emitting material layer, the first light-emitting layer 144 may include a phosphorescent light-emitting material layer containing a host such as CBP and an iridium-based dopant (for example, dp2Ir (acac), op2Ir (acac)), or may contain the compound represented by the Chemical Formula 1 as described above. However, the present disclosure is not limited thereto. Alternatively, the first light-emitting layer 144 may include a fluorescent light-emitting material layer containing tris(8-hydroxyquinolinato)aluminum (Alq). In this connection, the emission wavelength from the first light-emitting layer 144 may range from 510 nm to 570 nm.

Further, when the first light-emitting layer 144 is embodied as a red (R) light-emitting material layer, the first light-emitting layer 144 may include a phosphorescent light-emitting material layer containing a host material such as CBP, the compound represented by the Chemical Formula 1 as described above, and at least one dopant selected from a group consisting of bis(1-phenylisoquinoline)acetylacetonate iridium (PIQIr(acac)), bis((1-phenylquinoline)acetylacetonate iridium (PQIr(acac)), and octaethylporphyrin platinum (PtOEP). However, the present disclosure is not limited thereto.

Alternatively, the first light-emitting layer 144 may include a fluorescent light-emitting material layer that contains 1,3,4-oxadiazole: Tris(dibenzoylmethane)mono(1,10-phentathroline)europium(III) (PBD:Eu(DBM)3(Phen)) or perylene and its derivatives. In this connection, the emission wavelength from the first light-emitting layer 144 may range from 600 nm to 650 nm.

Alternatively, when the first light-emitting layer 144 is embodied as a yellow (Y) light-emitting material layer, the first light-emitting layer 144 may be composed of a single yellow-green (YG) light-emitting material layer or a double layer of a YG light-emitting material layer and green (G) light-emitting material layer. In one example, when the first light-emitting layer 144 is embodied as the single yellow light-emitting material layer, the yellow light-emitting material layer may contain a host material selected from a group consisting of CBP, bis(2-methyl-8-quinolinolate)-4-(phenylphenolato)aluminium (BAlq), and the compound represented by the Chemical Formula 1 as described above, and a yellow-green phosphorescent dopant that emits yellow-green light. In this connection, the emission wavelength from the first light-emitting layer 144 may range from 510 nm to 590 nm.

In an alternative embodiment, in order to improve the red emission efficiency of the light emitting diode 100 having a tandem structure, the first light-emitting layer 144 may be embodied as a combination of two light-emitting material layers, for example, a combination of a yellow-green light-emitting material layer and a red light emission material layer, or a combination of a blue light-emitting material layer and a red light-emitting material layer.

In one example, when the second light-emitting layer 154 is embodied as a yellow-green light-emitting material layer, the second light-emitting layer 154 may be composed of a single yellow-green (YG) light-emitting material layer or a combination of a yellow-green light-emitting material layer and a green (G) light-emitting material layer. When the emitting layer 154 is composed of a single layer structure of a yellow-green light-emitting material layer, the second light-emitting layer 154 may contain a host material selected from a group consisting of CBP, BAlq, and the compound represented by the Chemical Formula 1 as described above, and a yellow-green phosphorescent dopant that emits yellow-green. However, the present disclosure is not limited thereto.

Alternatively, when the second light-emitting layer 154 is embodied as a yellow light-emitting material layer, the second light-emitting layer 154 may contain a host material selected from a group consisting of CBP, BAlq, and the compound represented by the Chemical Formula 1 as described above, and a phosphorescent dopant that emits yellow. However, the present disclosure is not limited thereto.

In one implementation according to the present disclosure, at least one of the first light-emitting layer and the second light-emitting layer may contain a host material including the compound of the chemical formula 1 as described above.

In one example, the first electron-transporting layer 146 and the second electron-transporting layer 156 facilitate electrons transport in the first light emission sub-stack 140 and the second light emission sub-stack 150, respectively. Each of the first and second electron-transporting layers 146 and 156 may contain one selected from a group consisting of oxadiazole, triazole, phenanthroline, benzoxazole, benzothiazole, benzimidazole, triazine and derivatives thereof.

In one example, each of the first and second electron-transporting layers 146 and 156 may contain at least one selected from a group consisting of Alq3, 2-biphenyl-4-yl-5-(4-tbutylphenyl)-1,3,4-oxadiazole (PBD), spiro-PBD, lithiumquinolate (Liq), 2-[4-(9,10-Di-2-naphthalenyl-2-anthracenyl)phenyl]-1-phenyl-1Hbenzimidazol, 3-(biphenyl-4-yl)-5-(4-tertbutylphenyl)-4-phenyl-4H-1,2,4-triazole (TAZ), 4,7-diphenyl-1,10-phenanthroline (Bphen), tris(phenylquinoxaline) (TPQ), 1,3,5-Tri[(3-pyridyl)-phen-3-yl]benzene (TmPyPB) and/or 1,3,5-tris(N-phenylbenzimiazole-2-yl)benzene (TPBI).

Alternatively, each of the first and second electron-transporting layers 146 and 156 may contain the compound represented by the Chemical Formula 1 as described above.

Alternatively, each of the first and second electron-transporting layers 146 and 156 may be doped with an alkali metal or an alkaline earth metal compound. The metal components that may be employed as the dopants for each of the first and second electron-transporting layers 146 and 156 may include alkali metals such as lithium (Li), sodium (Na), potassium (K), and cesium (Cs), and/or alkaline earth metals such as magnesium (Mg), strontium (Sr), barium (Ba), and radium (Ra). However, the present disclosure is not limited thereto. The alkali metal or alkaline earth metal compound may be added in a ratio of approximately 1 to 20% by weight. The present disclosure is not limited thereto.

Each of the first and second electron-transporting layers 146 and 156 may have a thickness of 1 to 150 nm. When the thickness of each of the first and second electron-transporting layers 146 and 156 is 1 nm or greater, this may prevent the electrons transporting property from being degraded. When the thickness of each of the first and second electron-transporting layers 146 and 156 is 150 nm or smaller, this may prevent a driving voltage rise due to an increase in the thickness of each of the first and second electron-transporting layers 146 and 156. The first and second electron-transporting layers 146 and 156 may be of the same material or of different materials.

The electron-injecting layer 158 serves to facilitate the injection of the electrons. The electron-injecting layer 158 may contain alkali halide-based materials such as LiF, NaF, KF, RbF, CsF, FrF, BeF$_2$, MgF$_2$, CaF$_2$, SrF$_2$, BaF$_2$ and RaF$_2$ and/or organic materials such as Liq (lithium quinolate), lithium benzoate, sodium stearate, Alq3, BAlq, PBD, spiro-PBD, and TAZ. Alternatively, the electron-injecting layer 158 may contain the compound represented by the Chemical Formula 1 as described above.

A thickness of the electron-injecting layer 158 may be in a range of 0.5 to 50 nm. When the electron-injecting layer 158 is 0.5 nm or larger thick, this may prevent electrons injection characteristics from being degraded. When the thickness of the electron-injecting layer 158 is 50 nm or smaller, this may prevent the driving voltage from rising due to an increase in the thickness of the electron-injecting layer 158.

According to an exemplary embodiment of the present disclosure, in the organic electroluminescent device 100 having a tandem structure, the charge-generating layer (CGL) 160 to increase current efficiency in each light-emitting layer and to distribute the charge smoothly may be disposed between the first light emission sub-stack 140 and the second light emission sub-stack 150. That is, the charge-generating layer 160 is located between the first light emission sub-stack 140 and the second light emission sub-stack 150, and the first light emission sub-stack 140 and the second light emission sub-stack 150 are connected with each other via the charge-generating layer 160. The charge-generating layer 160 may be embodied as a PN-junction charge-generating layer composed of a vertical stack of a N-type charge-generating layer 162 and the P-type charge-generating layer 164.

The N-type charge-generating layer 162 is located between the first electron-transporting layer 146 and the second hole-transporting layer 152. The P-type charge-generating layer 164 is located between the N-type charge-generating layer 162 and the second hole-transporting layer 152. The charge-generating layer 160 generates charges and divides charges into holes and electrons to provide electrons and holes to the first and second light emission sub-stacks 140 and 150 respectively.

That is, the N-type charge-generating layer 162 supplies electrons to the first electron-transporting layer 146 of the first light emission sub-stack 140. Then, the first electron-transporting layer 146 supplies electrons to the first light-emitting layer 144 adjacent the first electrode 110. Meanwhile, the P-type charge-generating layer 164 supplies holes to the second hole-transporting layer 152 of the second light emission sub-stack 150. Then, the second hole-transporting layer 152 supplies holes to the second light-emitting layer 154 adjacent to the second electrode 120.

In this connection, the P-type charge-generating layer 164 may be made of a metal or an organic host material doped with a P-type dopant. In this connection, the metal may include one selected from a group consisting of Al, Cu, Fe, Pb, Zn, Au, Pt, W, In, Mo, Ni and Ti and alloys of at least two thereof. Further, the P-type dopant and the host material may employ materials known well to the skilled person to the art. In one example, the P-type dopant may include one selected from a group consisting of F4-TCNQ, iodine, FeCl$_3$, FeF$_3$ and SbCl$_5$. Further, the host material may include at least one selected from a group consisting of NPB, TPD, N, N, N', N'-tetranaphthalenyl-benzidine (TNB) and HAT-CN.

Alternatively, the N-type charge-generating layer 162 may contain, as a dopant, a metal compound such as an alkali metal or alkaline earth metal compound. The alkali metal or alkaline earth metal may be added at a ratio of about 1 to 30% by weight based on a weight of the organic compound according to the present disclosure. However, the present disclosure is not limited thereto.

The N-type charge-generating layer 162 may be doped with an alkali metal or alkaline earth metal compound to improve electrons injection ability into the first electron-transporting layer 146. Specifically, when an alkali metal or an alkaline earth metal is used as a dopant for the N-type charge-generating layer 162, the alkali metal or an alkaline earth metal used as the dopant bonds with the organic compound in accordance with the present disclosure to form a gap state. Thus, a difference between energy levels of the N-type charge-generating layer 162 and the P-type charge-generating layer 164 is reduced, and, thus, electrons injection ability from the N-type charge-generating layer 162 to the first electron-transporting layer 146 is improved.

In FIG. 2, the organic electroluminescent device 200 includes a first electrode 210 and a second electrode 220 facing away each other, and an organic light-emitting layer 230 positioned between the first electrode 210 and the second electrode 220. The organic light-emitting layer 230 may include a vertical stack of a first light emission sub-stack (ST1) 240, a second light emission sub-stack (ST2) 250, a third light emission sub-stack (ST3) 270, a first charge-generating layer (CGL1) 260, and a second charge-generating layer (CGL2) 280. Alternatively, at least four light emission sub-stacks and at least three charge-generating layers may be disposed between the first and second electrodes 210 and 220.

As described above, the first electrode 210 may act as an anode for injecting holes, and may be made of any one of a conductive material having a high work function, for example, ITO, IZO, or ZnO. The second electrode 220 may act as a cathode for injecting electrons and may be made of any conductive material having a low work function, for example, aluminum (Al), magnesium (Mg), or aluminum-magnesium alloy (AlMg).

The first and second charge-generating layers 260 and 280 are located between the first and second light emission sub-stacks 240 and 250 and between the second and third light emission sub-stacks 250 and 270, respectively. The first light emission sub-stack 240, first charge-generating layer 260, second light emission sub-stack 250, second charge-generating layer 280 and third light emission sub-stack 270 are sequentially stacked on the first electrode 210. That is, the first light emission sub-stack 240 is positioned between the first electrode 210 and the first charge-generating layer 260. The second light emission sub-stack 250 is positioned between the first charge-generating layer 260 and the second charge-generating layer 280. The third light emission sub-stack 270 is located between the second electrode 220 and the second charge-generating layer 280.

The first light emission sub-stack 240 may include a vertical stack of the hole-injecting layer 241, the first hole-transporting layer 242, the first light-emitting layer 244, and the first electron-transporting layer 246 on the first electrode 210. In this connection, the hole-injecting layer 241 and the first hole-transporting layer 242 are located between the first electrode 210 and the first light-emitting layer 244. The hole-injecting layer 241 is located between the first electrode 210 and the first hole-transporting layer 242. Further, the first electron-transporting layer 246 is located between the first light-emitting layer 244 and the first charge-generating layer 260.

The hole-injecting layer 241, the first hole-transporting layer 242, the first light-emitting layer 244, and the first electron-transporting layer 246 may be respectively identical with the hole-injecting layer 141, the first hole-transporting layer 142, the first light-emitting layer 144 and the first electron-transporting layer 146. Thus, a description thereof will be omitted. For example, the first light-emitting layer 244 may be embodied as a blue (B) light-emitting material layer. In this connection, the emission wavelength from the first light emission sub-stack 240 may range from 440 nm to 480 nm.

The second light emission sub-stack 250 may include a vertical stack of the second hole-transporting layer 252, the second light-emitting layer 254, and the second electron-transporting layer 256. The second hole-transporting layer 252 is located between the first charge-generating layer 260 and the second light-emitting layer 254. The second electron-transporting layer 256 is located between the second light-emitting layer 254 and the second charge-generating layer 280.

The second hole-transporting layer 252, the second light-emitting layer 254 and the second electron-transporting layer 256 may be respectively identical with the second hole-transporting layer 152, the second light-emitting layer 154 and the second electron-transporting layer 156. Thus, a description thereof will be omitted. For example, the second light-emitting layer 254 may be embodied as a yellow-green (YG) or yellow (Y) light-emitting material layer. In this connection, the emission wavelength from the second light emission sub-stack 250 may range from 510 nm to 590 nm or range from 460 nm to 510 nm.

The third light emission sub-stack 270 may include a vertical stack of a third hole-transporting layer 272, a third light-emitting layer 274, a third electron-transporting layer 276, and an electron-injecting layer 278. The third hole-transporting layer 272 is located between the second charge-generating layer 280 and the third light-emitting layer 274. The third electron-transporting layer 276 is located between the third light-emitting layer 274 and the second electrode 220. The electron-injecting layer 278 is located between the third electron-transporting layer 276 and the second electrode 220.

The third hole-transporting layer 272, the third electron-transporting layer 276, and the electron-injecting layer 278 may be respectively identical with the second hole-transporting layer 152, the second electron-transporting layer 156, and the electron-injecting layer 158. Thus, a description thereof will be omitted. The third light-emitting layer 274 may be identical with the first light-emitting layer 144 or the second light-emitting layer 154. For example, the third light-emitting layer 274 may be embodied as a blue (B) light-emitting material layer. In this connection, the emission wavelength from the third light emission sub-stack 270 may range from 440 nm to 480 nm. In another alternative embodiment, the third light-emitting layer 274 may be embodied as a yellow-green (YG) or yellow (Y) light-emitting material layer. In this case, the emission wavelength from the third light emission sub-stack 270 may range from 460 nm to 590 nm.

In one implementation according to the present disclosure, at least one of the first light-emitting layer, the second light-emitting layer and the third light-emitting layer contains, as the host material, the compound having the chemical formula 1 as described above.

The first charge-generating layer 260 is located between the first light emission sub-stack 240 and the second light emission sub-stack 250. The second charge-generating layer 280 is located between the second light emission sub-stack 250 and the third light emission sub-stack 270. Each of the first and second charge-generating layers 260 and 280 may embodied as a PN-junction charge-generating layer composed of a vertical stack of each of the N-type charge-generating layers 262 and 282 and each of the P-type charge-generating layers 264 and 284.

In the first charge-generating layer 260, the N-type charge-generating layer 262 is located between the first electron-transporting layer 246 and the second hole-transporting layer 252. The P-type charge-generating layer 264 is located between the N-type charge-generating layer 262 and the second hole-transporting layer 252.

Further, in the second charge-generating layer 280, the N-type charge-generating layer 282 is located between the second electron-transporting layer 256 and the third hole-transporting layer 272. The P-type charge-generating layer 284 is located between the N-type charge-generating layer 282 and the third hole-transporting layer 272.

Each of the first and second charge-generating layers 260 and 280 generates charges and/or divides the charges into electrons and holes to supply the electrons and holes into each of the first to third light emission sub-stacks 240, 250 and 270.

That is, in the first charge-generating layer 260, the N-type charge-generating layer 262 supplies electrons to the first electron-transporting layer 246 of the first light emission sub-stack 250. The P-type charge-generating layer 264 supplies holes to the second hole-transporting layer 252 of the second light emission sub-stack 250.

Further, in the second charge-generating layer 280, the N-type charge-generating layer 282 supplies electrons to the second electron-transporting layer 256 of the second light emission sub-stack 250. The P-type charge-generating layer 284 supplies holes to the third hole-transporting layer 272 of the third light emission sub-stack 270.

In this connection, each of the P-type charge-generating layers 262 and 282P may be made of a metal or an organic host material doped with a P-type dopant. In this connection, the metal may include one or more selected from a group consisting of Al, Cu, Fe, Pb, Zn, Au, Pt, W, In, Mo, Ni, Ti and alloys of at least two thereof. Further, the P-type dopant and the host material may include materials conventionally employed by the skilled person to the art. For example, the P-type dopant may include a material selected from a group consisting of F4-TCNQ, iodine, $FeCl_3$, $FeF_3$ and $SbCl_5$. Further, the host material may include at least one material selected from the group consisting of NPB, TPD, TNB and HAT-CN.

Alternatively, each of the N-type charge-generating layer 262, 282 may contain, as a dopant, a metal compound including an alkali metal or alkaline earth metal.

For example, each of the N-type charge-generating layers 262 and 282 may contain at least one material selected from a group consisting of LiQ, LiF, NaF, KF, RbF, CsF, FrF, $BeF_2$, $MgF_2$, $CaF_2$, $SrF_2$, $BaF_2$ and $RaF_2$ in addition to the organic compound according to the present disclosure. However, the present disclosure is not limited thereto.

The n-type charge-generating layers 262 and 282 may be doped with a metal or an alkaline earth metal compound to improve electrons injection ability into the electron-transporting layers 246 and 256.

The organic electroluminescent device according to the present disclosure may be applied to an organic light emitting display device and an illumination device using an organic electroluminescent device. In one example, FIG. 3 is a schematic cross-sectional view of an organic light emission display device according to an exemplary embodiment of the present disclosure.

As shown in FIG. 3, the organic light emission display device 300 may include a substrate 301, an organic electroluminescent device 400, and an encapsulation film 390 covering the organic electroluminescent device 400. On the substrate 301, a driving thin-film transistor Td as a driving element and an organic electroluminescent device 400 connected to the driving thin-film transistor Td are disposed.

Although not shown, following components may be disposed on the substrate 301: a gate line and a data line defining a pixel region and intersecting each other; a power line extending parallel to and spaced from either the gate line or the data line; a switching thin-film transistor connected to the gate line and data line; and a storage (capacitor) connected to one electrode of the switching thin-film transistor and the power line.

The driving thin-film transistor Td is connected to the switching thin-film transistor. The driving thin-film transistor Td includes a semiconductor layer 310, a gate electrode 330, a source electrode 352, and a drain electrode 354.

The semiconductor layer 310 is formed on the substrate 301 and is made of an oxide semiconductor or polycrystalline silicon. When the semiconductor layer 310 is made of an oxide semiconductor material, a screening pattern (not shown) may not be formed beneath the semiconductor layer 310. The screening pattern prevents light from entering the semiconductor layer 310, thereby preventing the semiconductor layer 301 from being deteriorated by light. Alternatively, the semiconductor layer 310 may be made of polycrystalline silicon. In this case, impurities may be doped into both edges of the semiconductor layer 310.

On the semiconductor layer 310, a gate insulating film 320 made of an insulating material may be formed over an entire surface of the substrate 301. The gate insulating film 320 may be made of an inorganic insulating material such as silicon oxide or silicon nitride.

On the gate insulating film 320, the gate electrode 330 made of a conductive material such as metal is formed in a center region of the semiconductor layer 310. The gate electrode 330 is connected to a switching thin-film transistor.

On the gate electrode 330, an inter-layer insulating film 340 made of an insulating material is formed over the entire surface of the substrate 301. The inter-layer insulating film 3402 may be made of an inorganic insulating material such as silicon oxide or silicon nitride, or an organic insulating material such as benzocyclobutene or photo-acryl.

The inter-layer insulating film 340 has contact holes 342 and 344 exposing both lateral portions of the semiconductor layer 310. The contact holes 342 and 344 are spaced apart from the gate electrode 330 and disposed on both sides of the gate electrode 330 respectively.

On the inter-layer insulating film 340, the source electrode 352 and drain electrode 354 made of a conductive material such as a metal are disposed. The source electrode 352 and drain electrode 354 are disposed about the gate electrode 330 and are spaced from each other. The source electrode 352 and drain electrode 354 contacts both sides of the semiconductor layer 310 via the contact holes 342 and 344, respectively. The source electrode 352 is connected to a power line (not shown).

The semiconductor layer 310, the gate electrode 330, the source electrode 352, and the drain electrode 354 define the driving thin-film transistor Td. The driving thin-film transistor Td has a coplanar structure in which the gate electrode 330, the source electrode 352, and the drain electrode 354 are disposed in a coplanar manner on the semiconductor layer 310.

Alternatively, the driving thin-film transistor Td may have an inverted staggered structure in which the gate electrode is located below the semiconductor layer, and the source electrode and the drain electrode are located above the semiconductor layer. In this case, the semiconductor layer may be made of amorphous silicon. In one example, the switching thin-film transistor (not shown) may have substantially the same structure as the driving thin-film transistor Td.

In one example, the organic light emission display device 300 may include a color filter 360 that absorbs light generated from the organic electroluminescent device 400. For example, the color filter 360 may absorb red (R), green (G), blue (B), and white (W) light. In this case, color filter patterns that absorb the red, green and blue light may be disposed separately on a pixel basis. Each of these color filter patterns may overlap with a corresponding organic light-emitting layer 430 of the organic electroluminescent device 400 that emits light having a corresponding wavelength. Adopting the color filter 360 may allow the organic light emission display device 300 to render a full color range.

For example, when the organic light emission display device 300 is of a bottom light emission type, the color filter 360, which absorbs light, may be located above the interlayer insulating film 340 in a region of the organic electroluminescent device 400. In an alternative embodiment, when the organic light emission display device 300 is of a top light emission type, the color filter may be located on top of the organic electroluminescent device 400, i.e., on top of the second electrode 420. In one example, the color filter 360 may have a thickness of 2 to 5 μm. In this connection, the organic electroluminescent device 400 may be embodied as an organic electroluminescent device having a tandem structure as shown in FIG. 1 and FIG. 2.

In one example, a protective layer 370 having a drain contact hole 372 exposing the drain electrode 354 of the driving thin-film transistor Td may be formed to cover the driving thin-film transistor Td.

On the protective layer 370, the first electrode 410 connected to the drain electrode 354 of the driving thin-film transistor Td via the drain contact hole 372 may be formed on a pixel region basis.

The first electrode 410 may act as an anode and may be made of a conductive material having a relatively higher work function value. For example, the first electrode 410 may be made of a transparent conductive material such as ITO, IZO or ZnO.

In one example, when the organic light emitting display device 300 is of a top light emission type, a reflective electrode or a reflective layer may be further formed below the first electrode 410. For example, the reflective electrode or reflective layer may be made of any one of aluminum (Al), silver (Ag), nickel (Ni), and aluminum-palladium-copper (APC alloy).

On the protective layer 370, a bank layer 380 covering an edge of the first electrode 410 is formed. The bank layer 380 exposes a center region of the first electrode 410 corresponding to the pixel region.

An organic light-emitting layer 430 is formed on the first electrode 410. In one example, the organic light-emitting layer 430 may have at least two light emission sub-stacks shown in FIG. 1 and FIG. 2. Accordingly, the organic electroluminescent device 400 may have a tandem structure.

A second electrode 420 is formed on the organic light-emitting layer 430. The second electrode 420 may be disposed over an entire display region and may be made of a conductive material having a relatively lower work function value and may act as a cathode. For example, the second electrode 420 may be made of any one of aluminum (Al), magnesium (Mg), and aluminum-magnesium alloy (AlMg).

The first electrode 410, the organic light-emitting layer 430 and the second electrode 420 together define the organic electroluminescent device 400.

On the second electrode 420, the encapsulation film 390 is formed to prevent external moisture from penetrating into the organic electroluminescent device 400. Although not shown, the encapsulation film 390 may have a triple layer structure in which a first inorganic layer and an organic layer and a second inorganic layer are sequentially stacked. However, the present disclosure is not limited thereto.

As used herein, the term "halogen group" may include fluorine, chlorine, bromine or iodine.

As used herein, the term "alkyl" means a monovalent substituent derived from straight or branched saturated hydrocarbons having 1 to 40 carbon atoms. Examples thereof include, but are not limited to, methyl, ethyl, propyl, isobutyl, sec-butyl, pentyl, iso-amyl and hexyl.

As used herein, the term "alkenyl" means a monovalent substituent derived from linear or branched unsaturated hydrocarbons having one or more carbon-carbon double bonds and having 2 to 40 carbon atoms. Examples thereof include, but are not limited to, vinyl, allyl, isopropenyl, 2-butenyl, and the like.

As used herein, the term "alkynyl" means a monovalent substituent derived from linear or branched unsaturated hydrocarbons having one or more carbon-carbon triple bonds and having 2 to 40 carbon atoms. Examples thereof include, but are not limited to, ethynyl, 2-propynyl, and the like.

As used herein, the term "aryl" means a monovalent substituent derived from aromatic hydrocarbons having a single ring or a combination of two or more rings and having 2 to 60 carbon atoms. Further, such aryl may have a form in which two or more rings are simply pendant with each other or are condensed with each other. Examples of such aryl include, but are not limited to, phenyl, naphthyl, phenanthryl, anthryl, dimethylfluorenyl, and the like.

As used herein, the term "heteroaryl" means a monovalent substituent derived from monoheterocyclic or polyheterocyclic aromatic hydrocarbons having 6 to 30 carbon atoms. In this connection, at least one carbon, preferably 1 to 3 carbons in a ring is substituted with a heteroatom such as N, O, S or Se. Furthermore, such heteroaryl may have a form in which two or more rings are simply pendant with each other or are condensed with each other or are condensed with the aryl group. Examples of such heteroaryl include 6-membered monocyclic rings such as pyridyl, pyrazinyl, pyrimidinyl, pyridazinyl, and triazinyl, polycyclic rings such as phenoxathienyl, indolizinyl, indolyl, purinyl, quinolyl, benzothiazole, carbazolyl, and 2-furanyl, N-imidazolyl, 2-isoxazolyl, 2-pyridinyl, 2-pyrimidinyl, etc. However, the present disclosure is not limited thereto.

As used herein, the term "aryloxy" refers to a monovalent substituent represented by RO—, wherein R represents aryl having 6 to 60 carbon atoms. Examples of such aryloxy include, but are not limited to, phenyloxy, naphthyloxy, diphenyloxy, and the like.

As used herein, the term "alkyloxy" means a monovalent substituent represented by R'O—, where R' means alkyl having 1 to 40 carbon atoms. Such alkyloxy has a linear, branched or cyclic structure. Examples of alkyloxy include, but are not limited to, methoxy, ethoxy, n-propoxy, 1-propoxy, t-butoxy, n-butoxy and pentoxy.

As used herein, the term "alkoxy" refers to a straight chain, branched chain or cyclic chain. A carbon number of the alkoxy is not particularly limited, but the alkoxy preferably has 1 to 20 carbon atoms. Specific examples thereof include, but are not limited to, methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3-dimethylbutyloxy, 2-ethylbutyloxy, n-octyloxy, n-nonyloxy, n-decyloxy, benzyloxy, p-methylbenzyloxy, As used herein, the term "aralkyl" means an univalent radical derived from an alkyl radical by replacing one or more hydrogen atoms with aryl groups. Preferred aralkyls includes lower alkyl groups. Non-limiting examples of suitable aralkyl groups include benzyl, 2-phenethyl and naphthalenylmethyl. A bond to a parent moiety is achieved via the alkyl.

As used herein, the term "arylamino group" means an amine substituted with an aryl group having 6 to 30 carbon atoms.

As used herein, the term "alkylamino group" means an amine substituted with an alkyl group having 1 to 30 carbon atoms.

As used herein, the term "aralkylamino group" means an amine substituted with an aryl-alkyl group having from 6 to 30 carbon atoms.

As used herein, the term "heteroarylamino group" means an amine group substituted with an aryl group having 6 to 30 carbon atoms and a heterocyclic group.

As used herein, the term "heteroaralkyl group" means an aryl-alkyl group substituted with a heterocyclic group.

As used herein, the term "cycloalkyl" means a monovalent substituent derived from monocyclic or polycyclic non-aromatic hydrocarbons having 3 to 40 carbon atoms. Examples of such cycloalkyls include, but are not limited to, cyclopropyl, cyclobutyl, cyclopentyl, cyclohexyl, norbornyl, adamantine, and the like.

As used herein, the term "heterocycloalkyl" means a monovalent substituent derived from non-aromatic hydrocarbon having 3 to 40 carbon atoms, where at least one carbon, preferably 1 to 3 carbons in a ring is substituted with a heteroatom such as N, O, S or Se. Examples of such heterocycloalkyl include, but are not limited to, morpholine, piperazine, and the like.

As used herein, the term "alkylsilyl" refers to silyl substituted with alkyl having 1 to 40 carbon atoms.

As used herein, the term "arylsilyl" means silyl substituted with aryl having 6 to 60 carbon atoms.

As used herein, the term "condensed rings" means condensed aliphatic rings, condensed aromatic rings, condensed hetero-aliphatic rings, condensed hetero-aromatic rings, or combinations thereof.

As used herein, a term "a specific group bonds to an adjacent group to form a ring" means that the specific group bonds to the adjacent group to form a substituted or unsubstituted aliphatic hydrocarbon ring; a substituted or unsubstituted aromatic hydrocarbon ring; a substituted or unsubstituted aliphatic heterocycle; a substituted or unsubstituted aromatic heterocycle; or condensed rings thereof.

As used herein, the term "aliphatic hydrocarbon ring" refers to a ring that is not aromatic and consists only of carbon and hydrogen atoms.

As used herein, examples of the "aromatic hydrocarbon ring" include, but are not limited to, phenyl group, naphthyl group, anthracenyl group, and the like.

As used herein, the term "aliphatic hetero ring" means an aliphatic ring containing one or more heteroatoms.

As used herein, the term "aromatic hetero ring" means an aromatic ring containing one or more heteroatoms.

As used herein, aliphatic hydrocarbon rings, aromatic hydrocarbon rings, aliphatic heterocyclic rings and aromatic heterocyclic rings may be monocyclic or polycyclic.

As used herein, the term "substituted" means that a hydrogen atom bonded to a carbon atom in the compound is changed to another substituent. A position at which substitution occurs may refer to a position where the hydrogen atom is substituted. That is, the position is not limited to a specific position as long as a substituent is able to substitute at the position. When two or substitutions occur, two or more substituents may be the same or different.

As used herein, the term "unsubstituted" means that a hydrogen atom replaces another substituent. As used herein, the hydrogen atom may include hydrogen, deuterium, and tritium.

In accordance with the present disclosure, the organic electroluminescent device has the organic layer containing the deuterated anthracene organic compound to realize the lowered driving voltage, the increased lifetime, and excellent luminescence efficiency and external quantum efficiency (EQE) characteristics.

BRIEF DESCRIPTION OF THE SEVERAL VIEWS OF THE DRAWINGS

FIG. 1 shows a schematic cross-sectional view of an organic electroluminescent device having a tandem structure having two light emission sub-stacks and containing a compound represented by the Chemical Formula 1 according to one embodiment of the present disclosure.

FIG. 2 shows a schematic cross-sectional view of an organic electroluminescent device having a tandem structure having three light emission sub-stacks and containing a compound represented by the Chemical Formula 1 according to another embodiment of the present disclosure.

FIG. 3 is a cross-sectional view schematically showing an organic light emission display device having an organic electroluminescent device according to still another embodiment of the present disclosure.

DETAILED DESCRIPTION

Embodiments of the present disclosure are provided to more fully describe the present disclosure to those skilled in the art. The following embodiments may be modified in various different forms. A scope of the present disclosure is not limited to the following embodiments. Rather, these embodiments are provided so that the present disclosure will be more thorough and complete and are provided to fully convey ideas of the present disclosure to those skilled in the art.

According to one preferred implementation of the present disclosure, the compound represented by the Chemical Formula 1 may be selected from a group consisting of following compounds, but are not limited thereto:

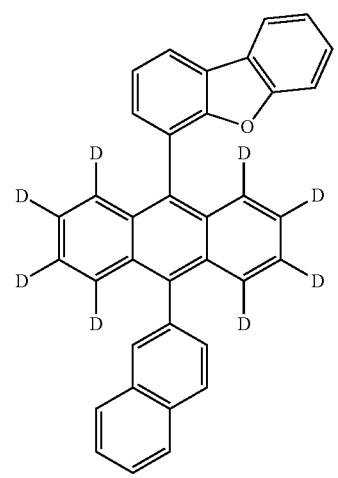

1

2
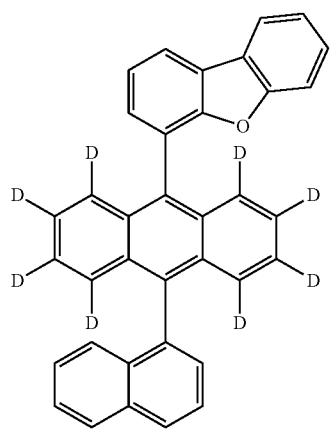
3
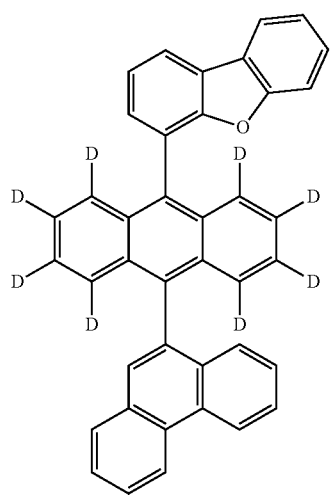
4
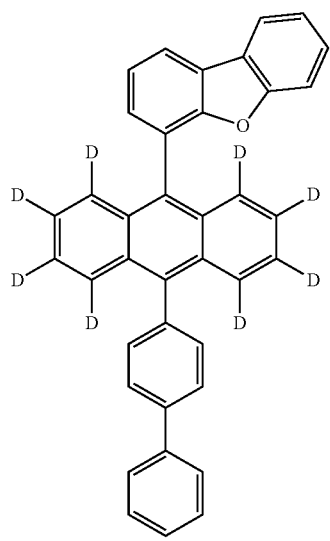
5
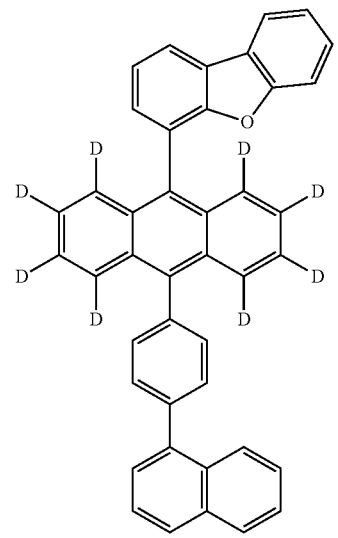
6
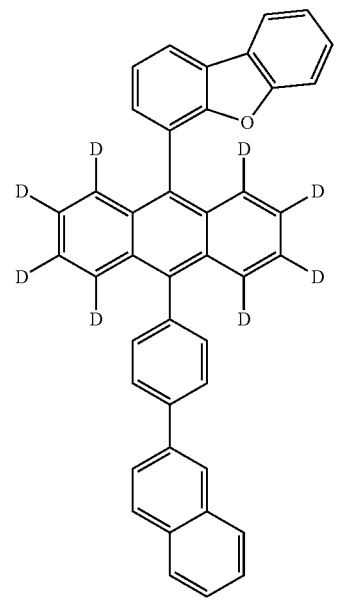
7
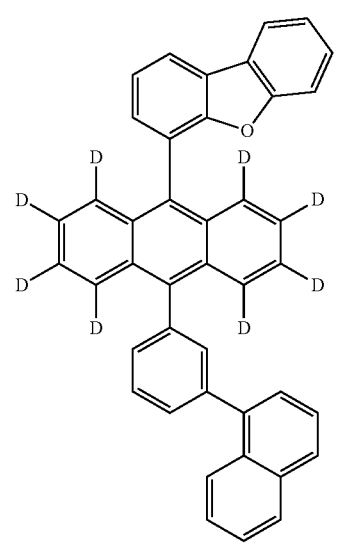

8
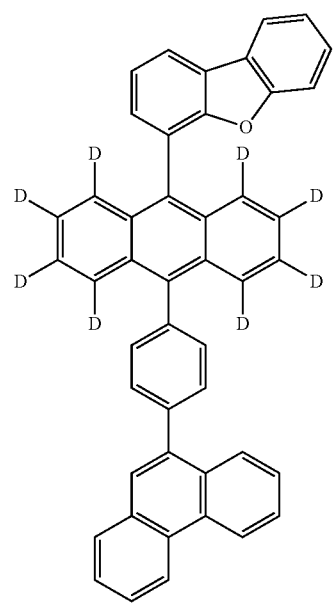
9
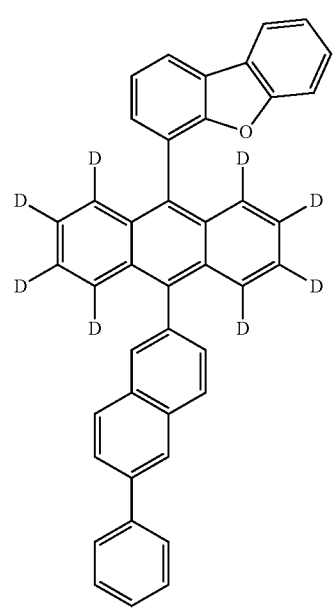
10
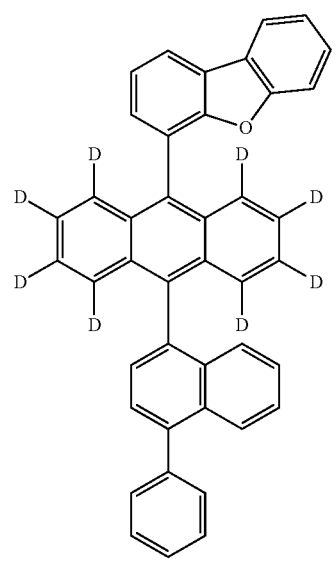
11
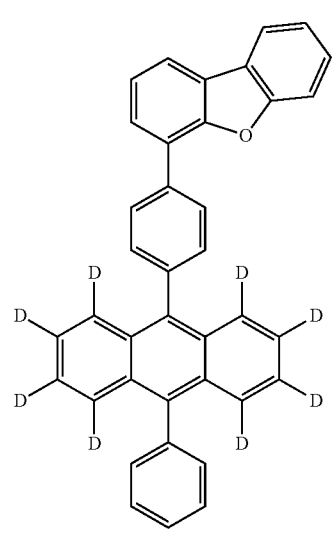
12
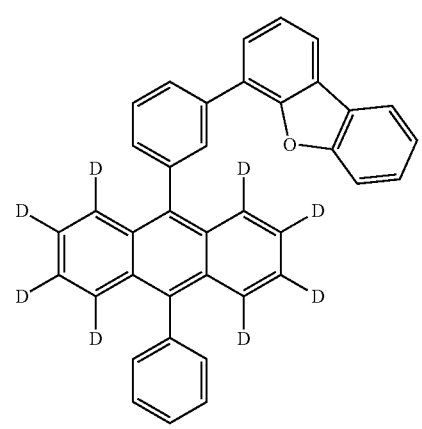

13
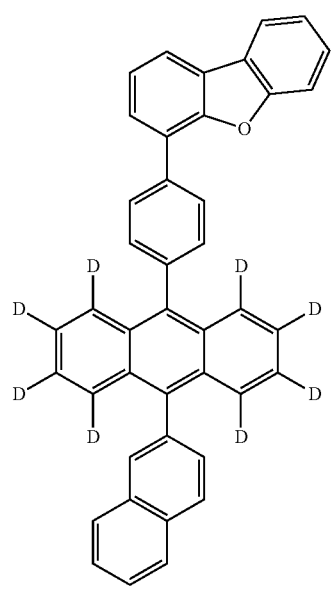
14
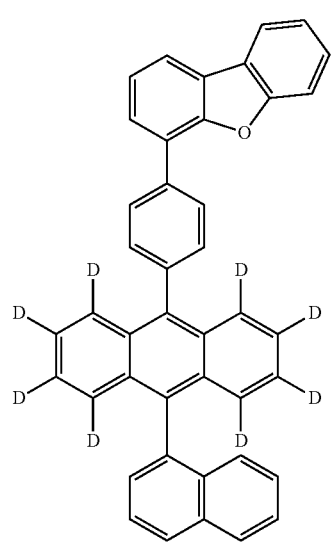
15
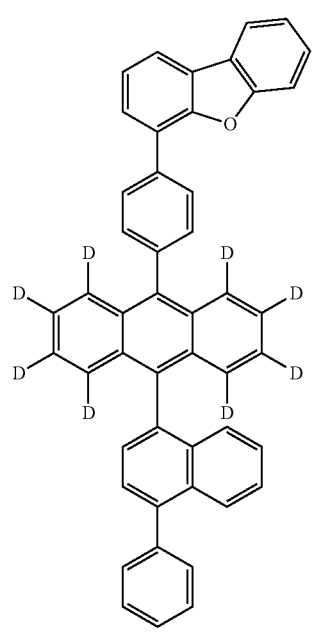
16
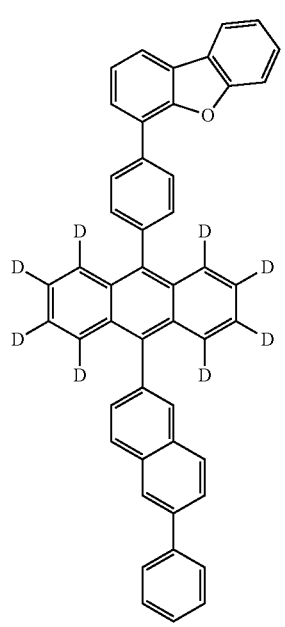

17
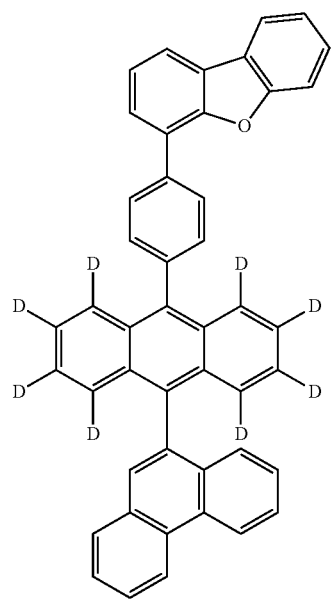
18
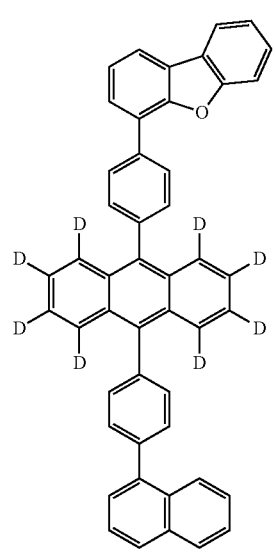
19
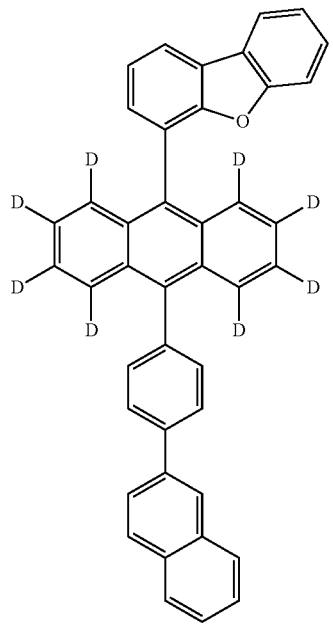
20
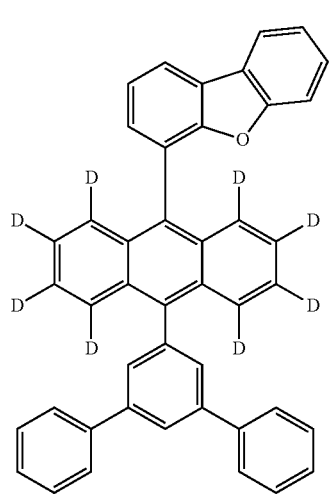

21
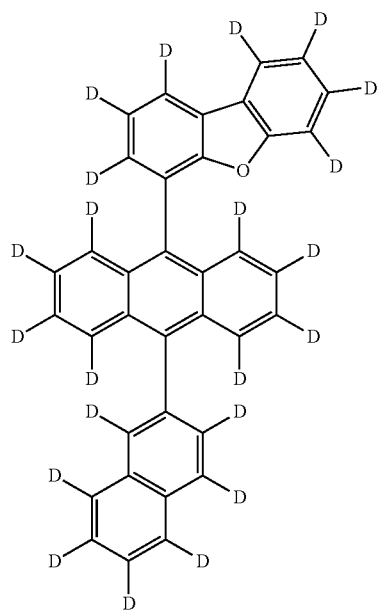
22
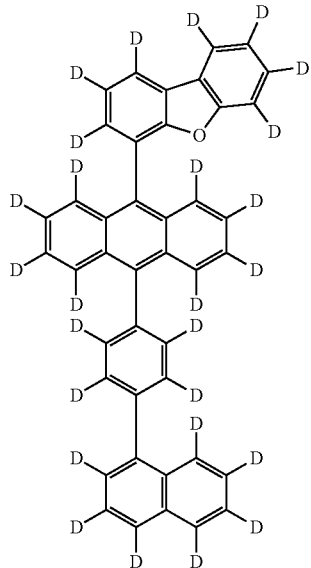
23
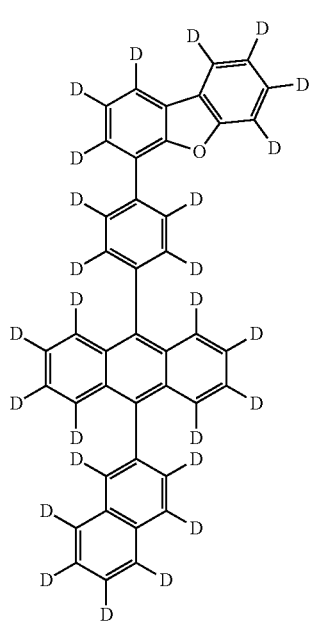
24

25
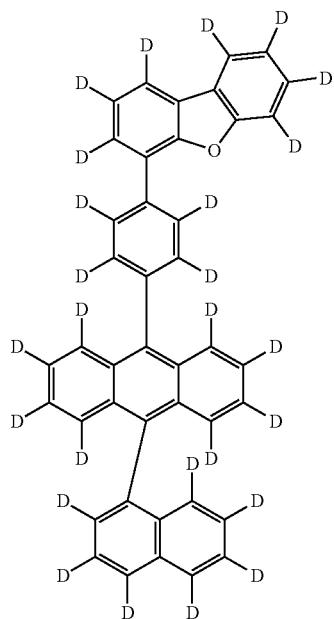
26
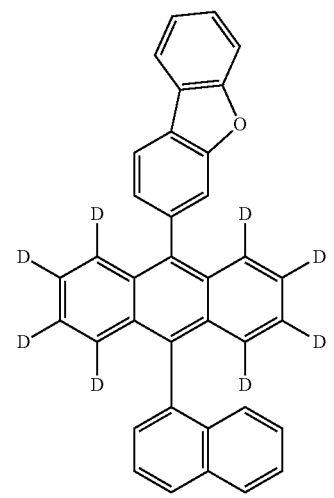
27
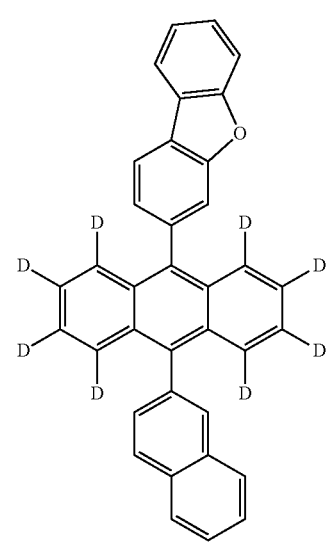
28
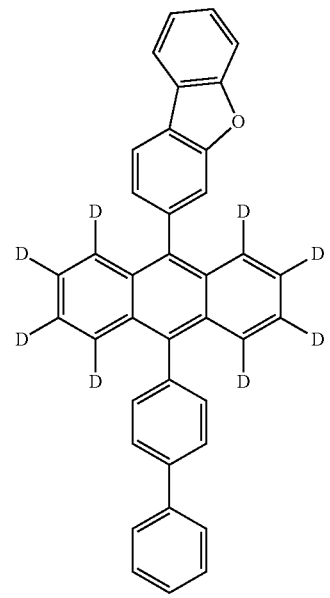
29
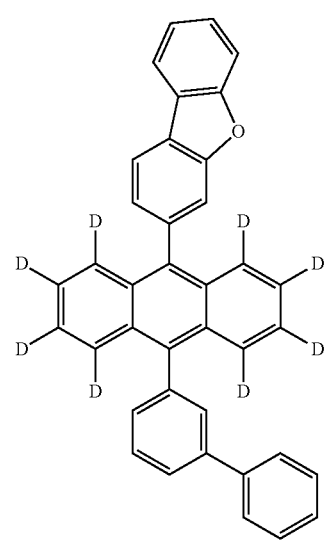

30
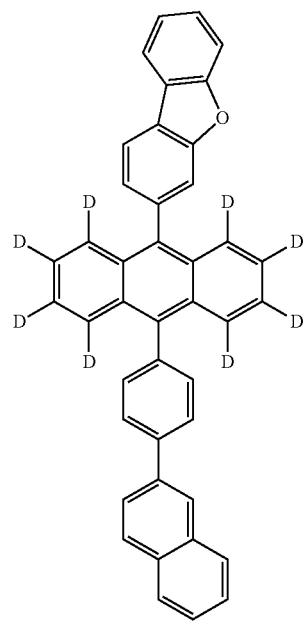
31
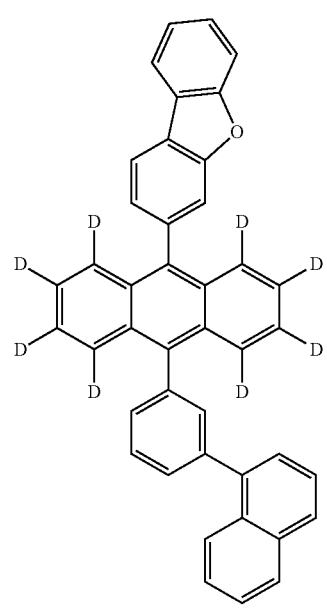
32
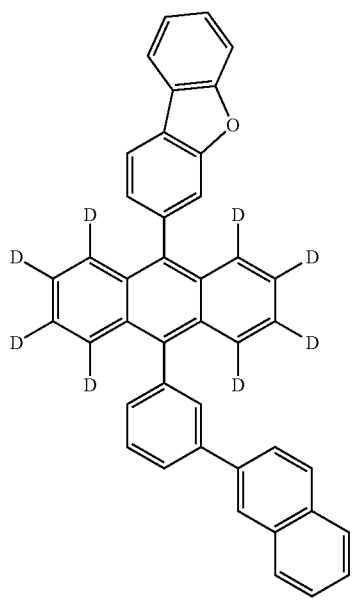
33
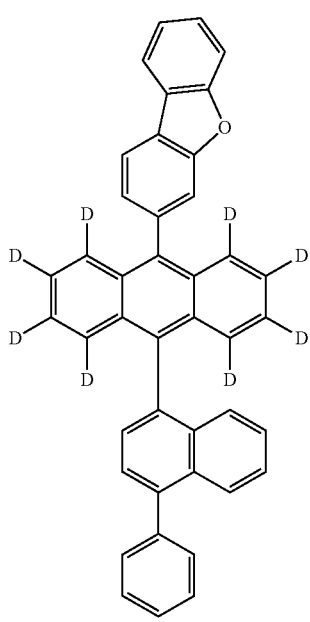

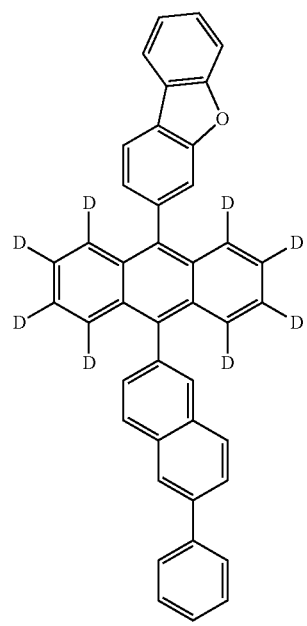
34
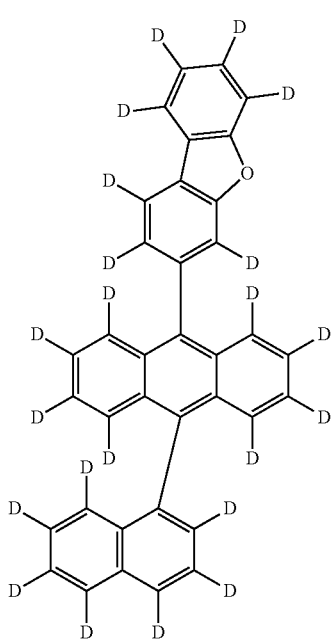
36
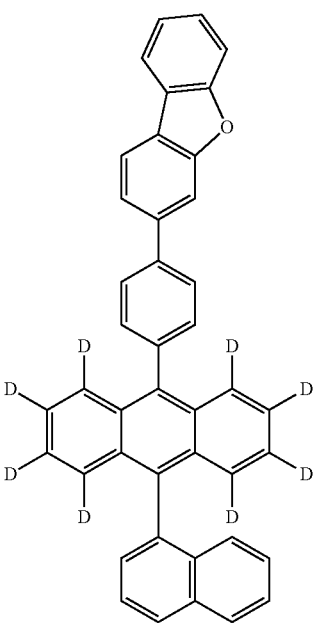
35
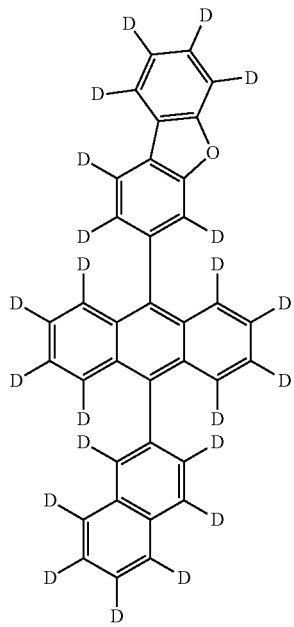
37

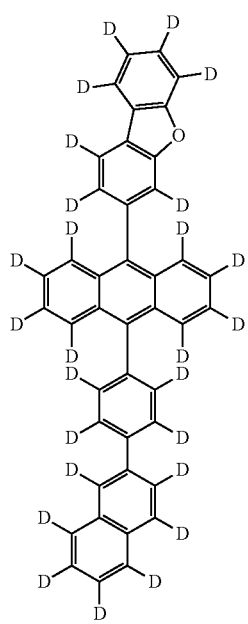
38
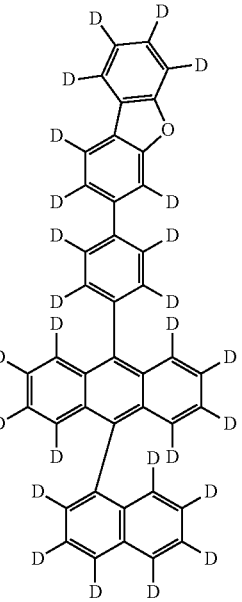
40
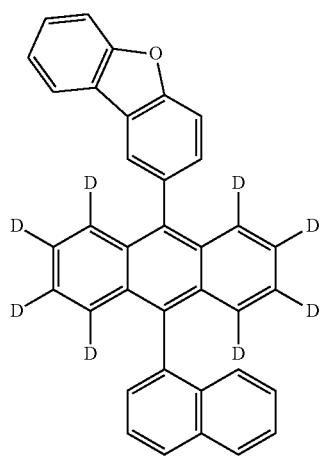
41
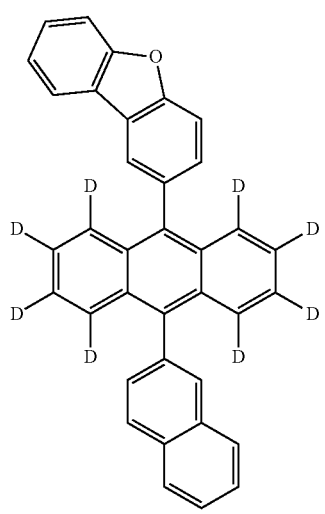
42

43
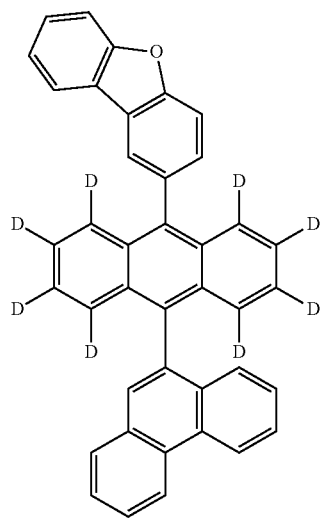
44
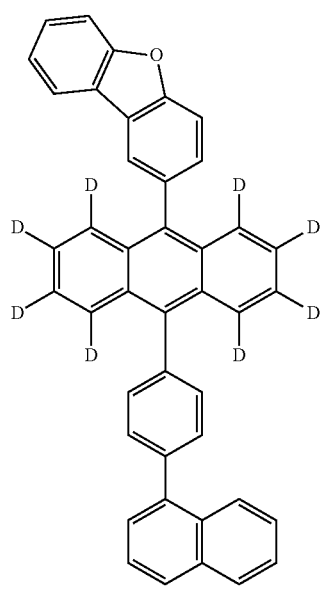
45
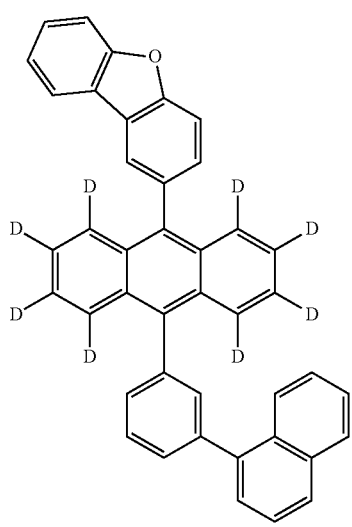
46
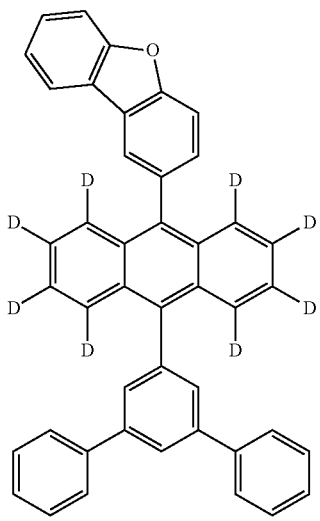
47
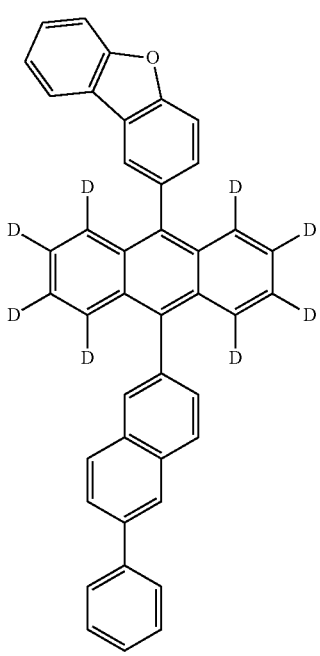

48
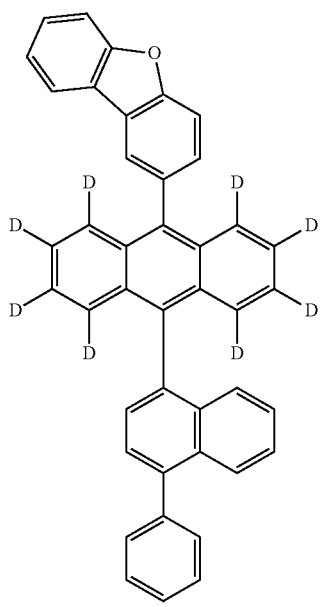
49
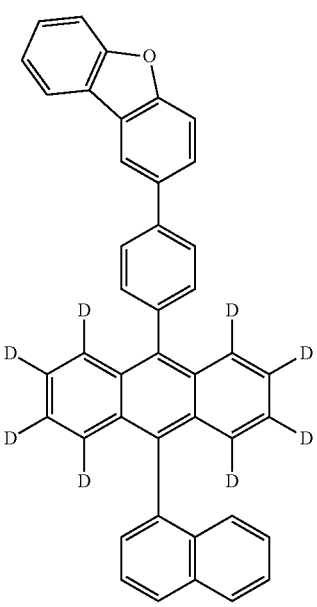
50
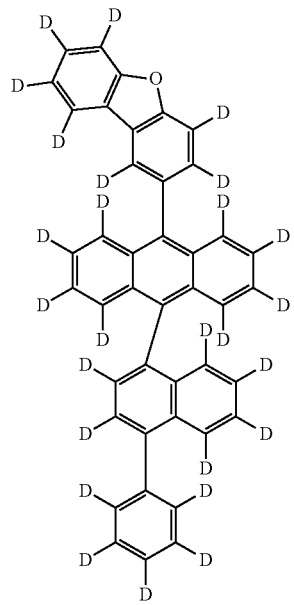
51
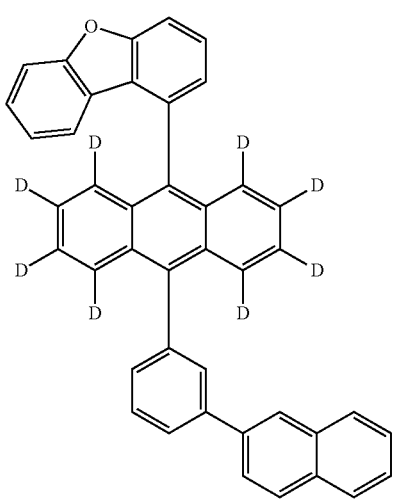
52
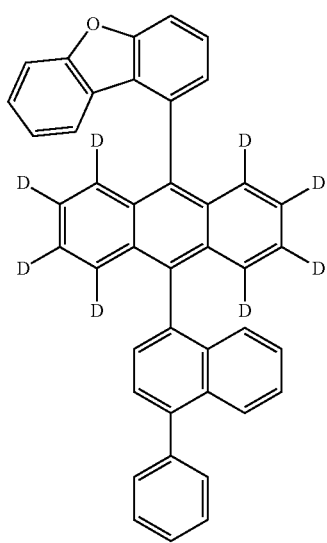

53
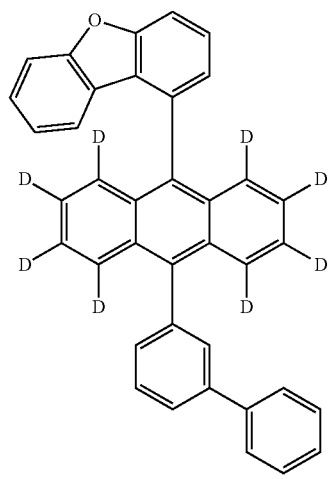
54
56
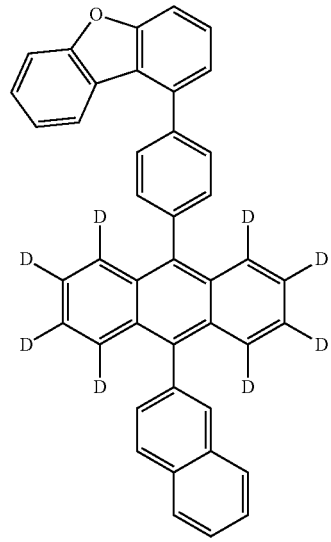
57
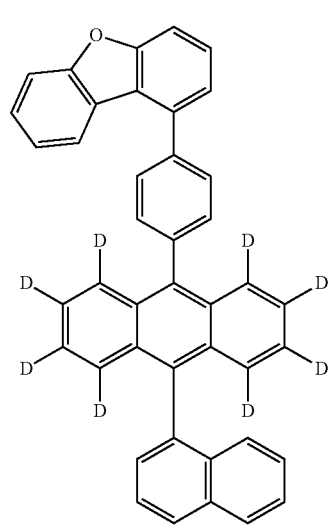
55
58
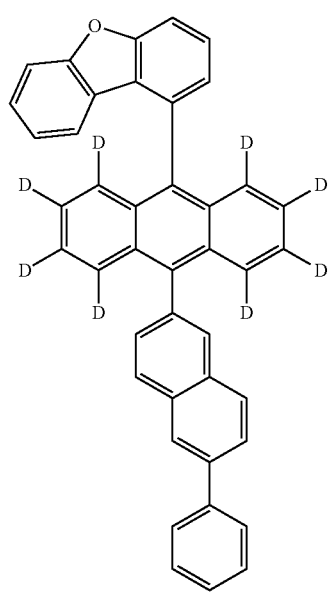
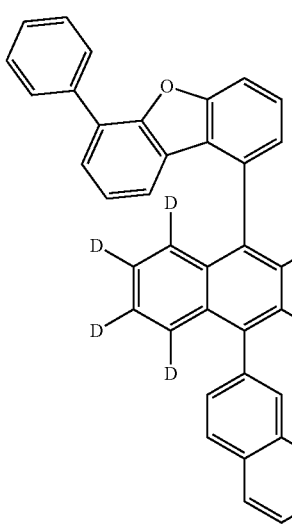

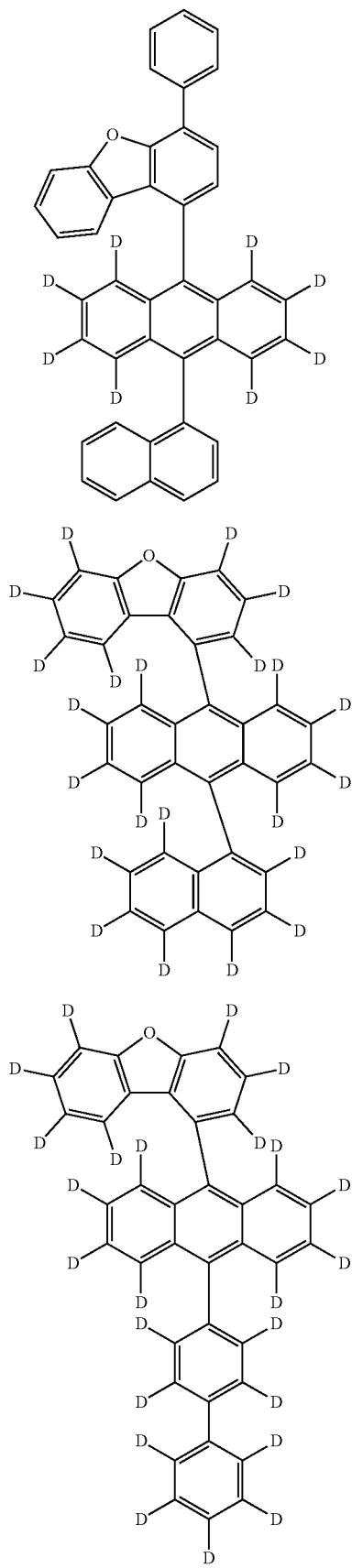

64
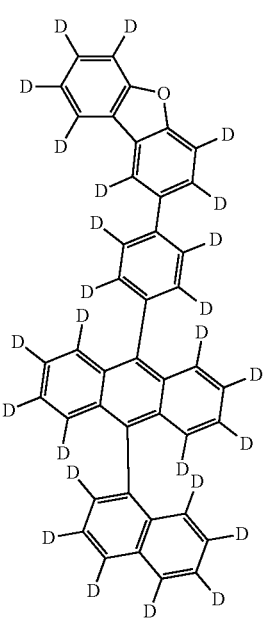
66
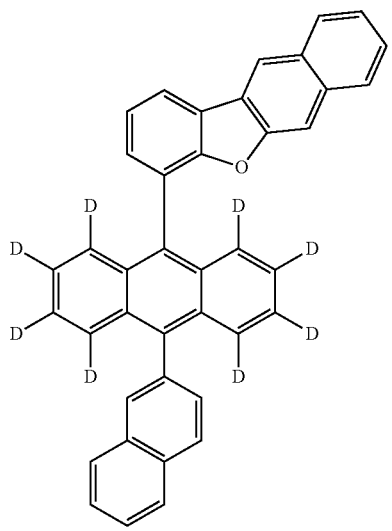
65
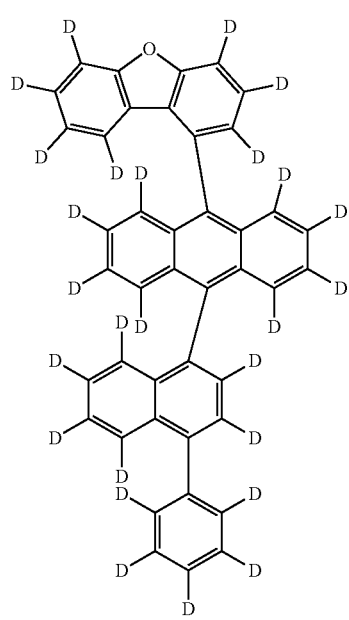
67
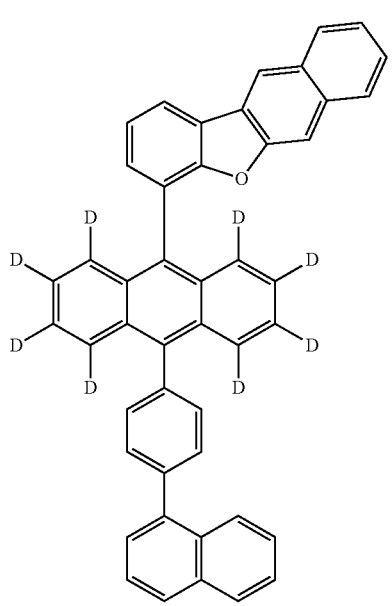

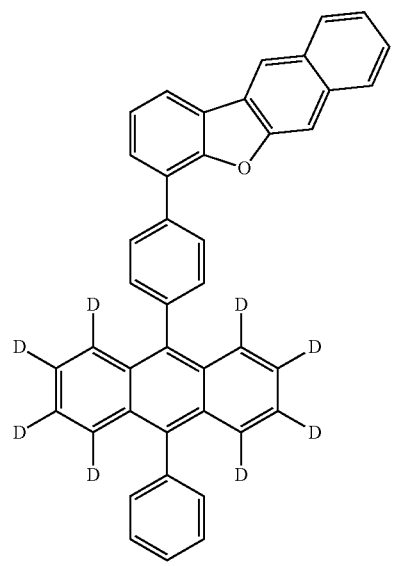
68
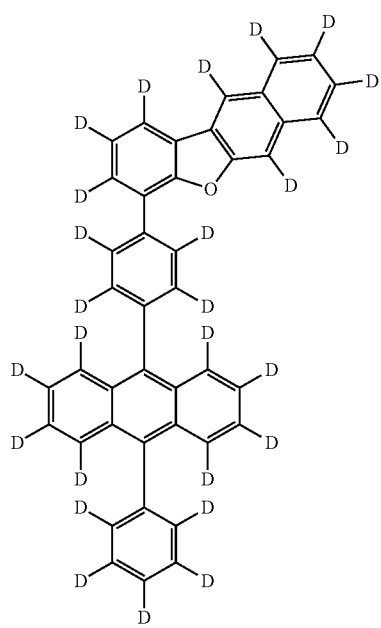
70
69
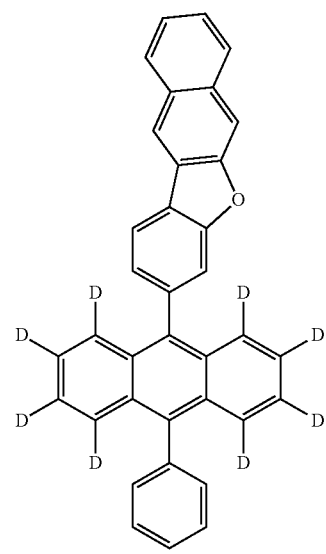
71

72
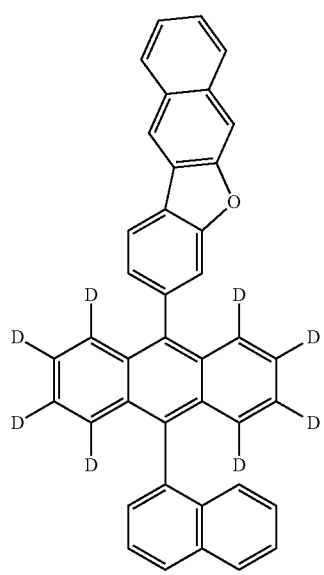
73
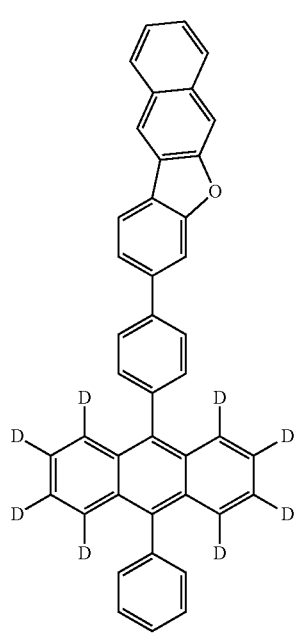
74
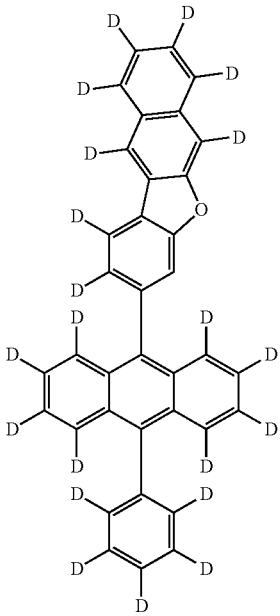
75
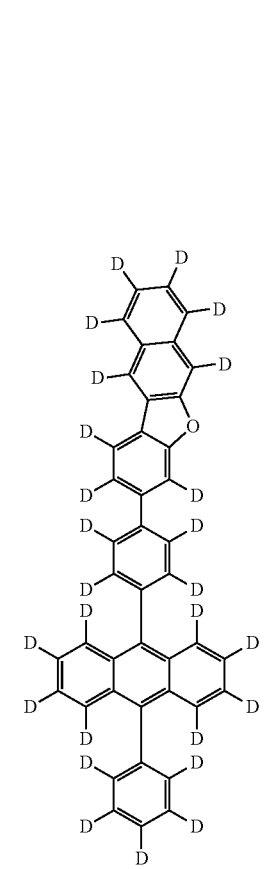

76
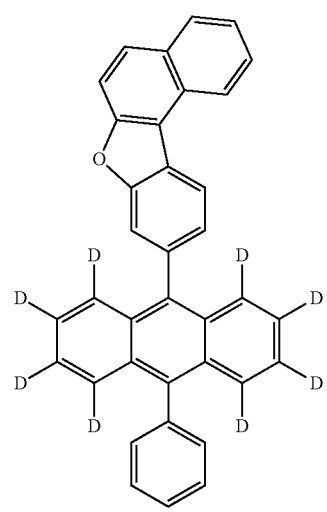
77
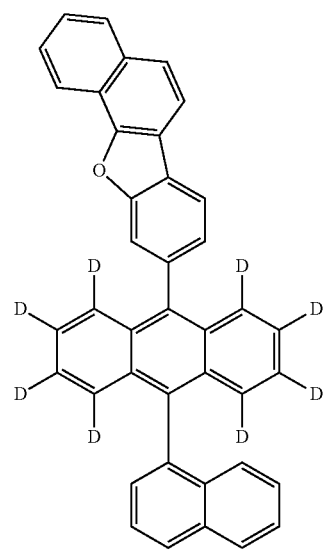
78
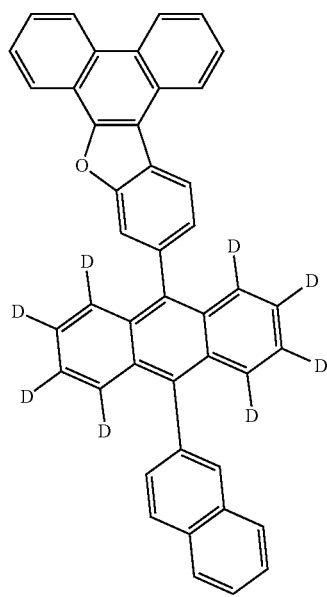
79
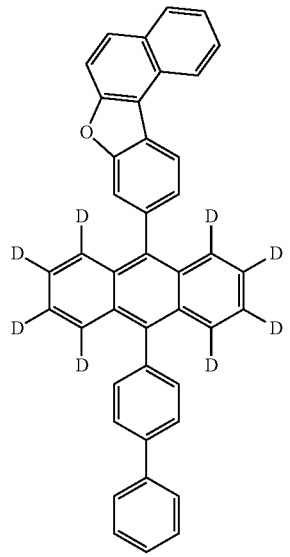
80
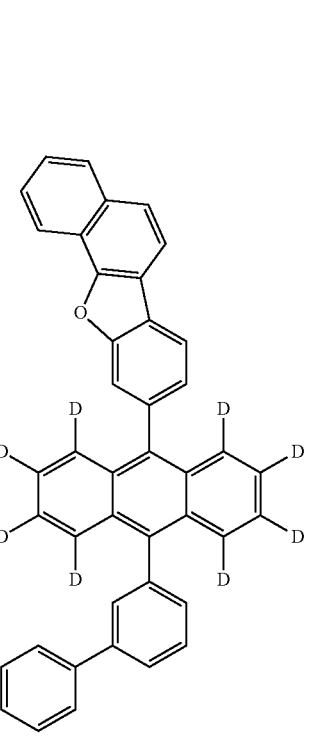

81
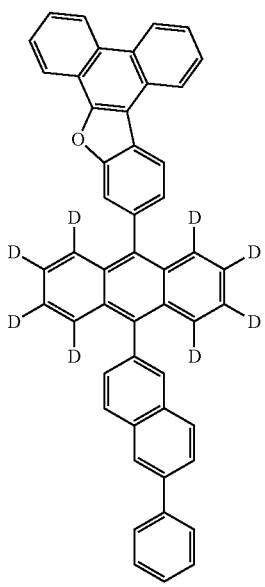
82
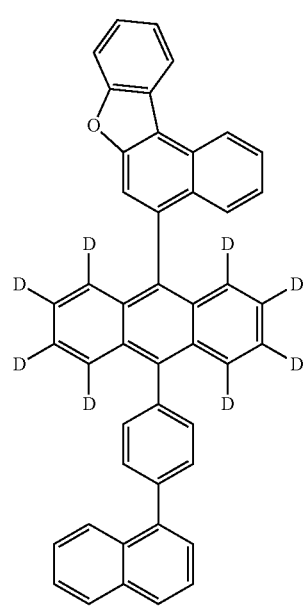
83
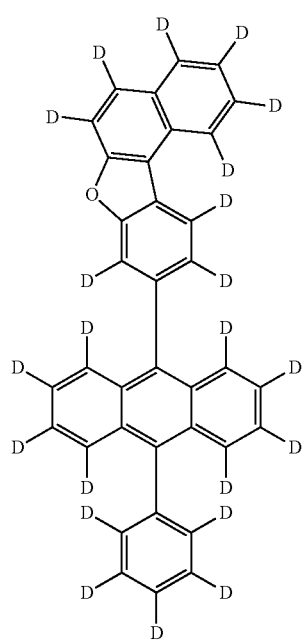
84
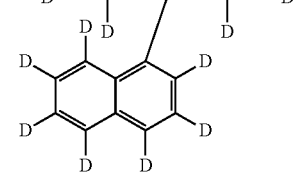

85
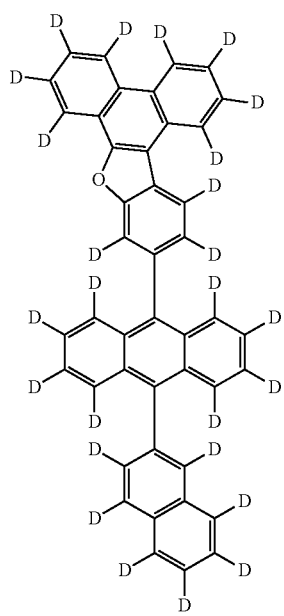
86
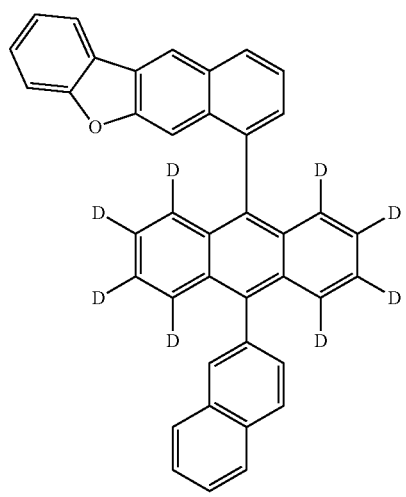
87
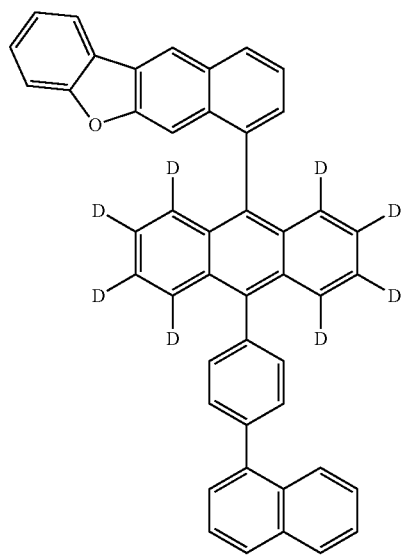
88
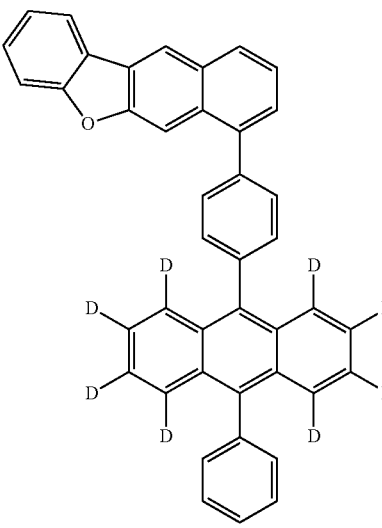
89
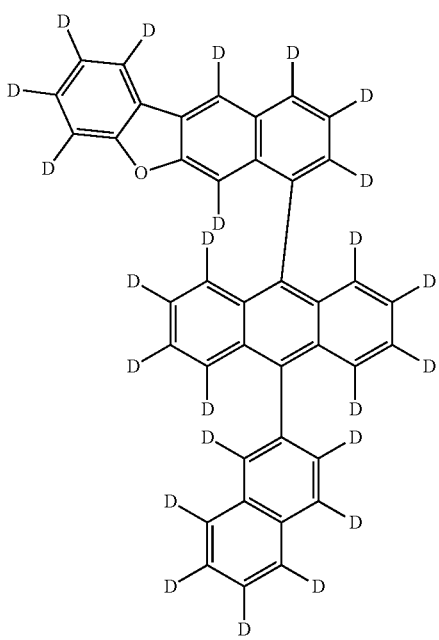

90
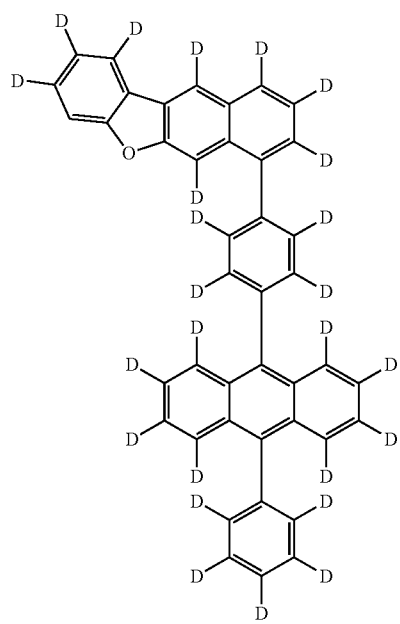
91
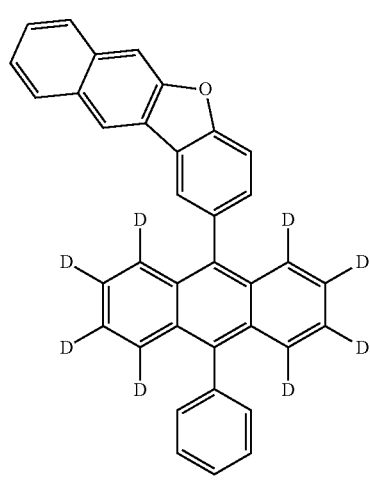
92
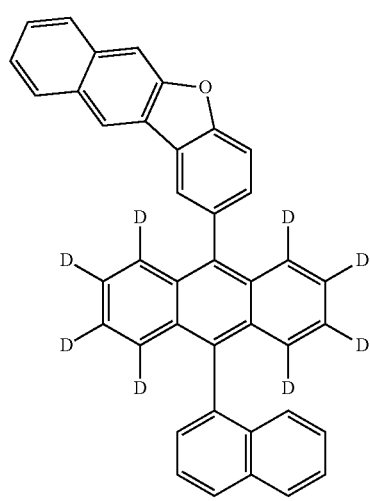
93
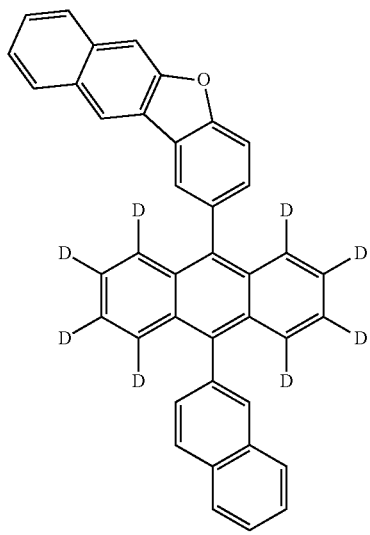
94
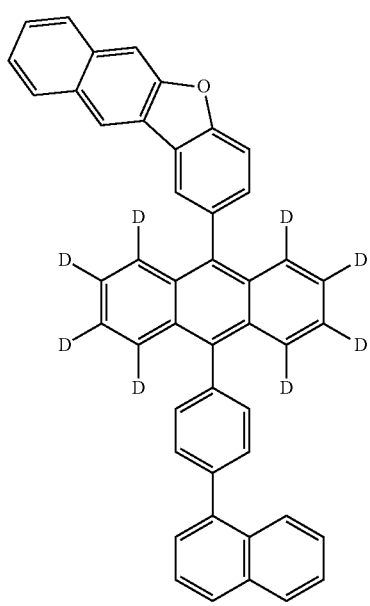

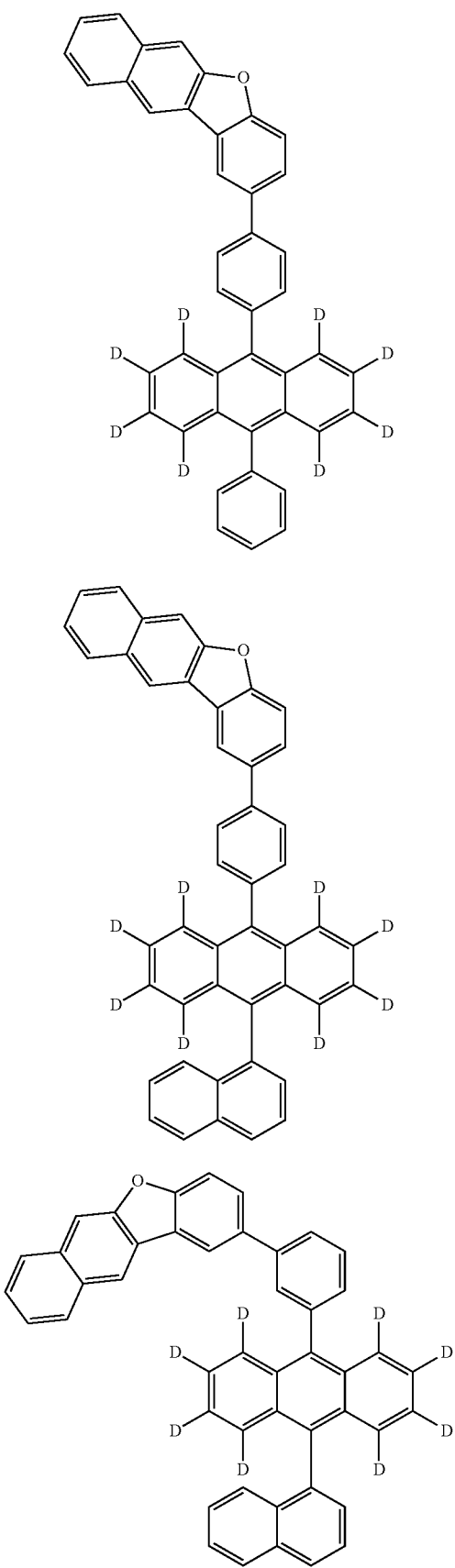
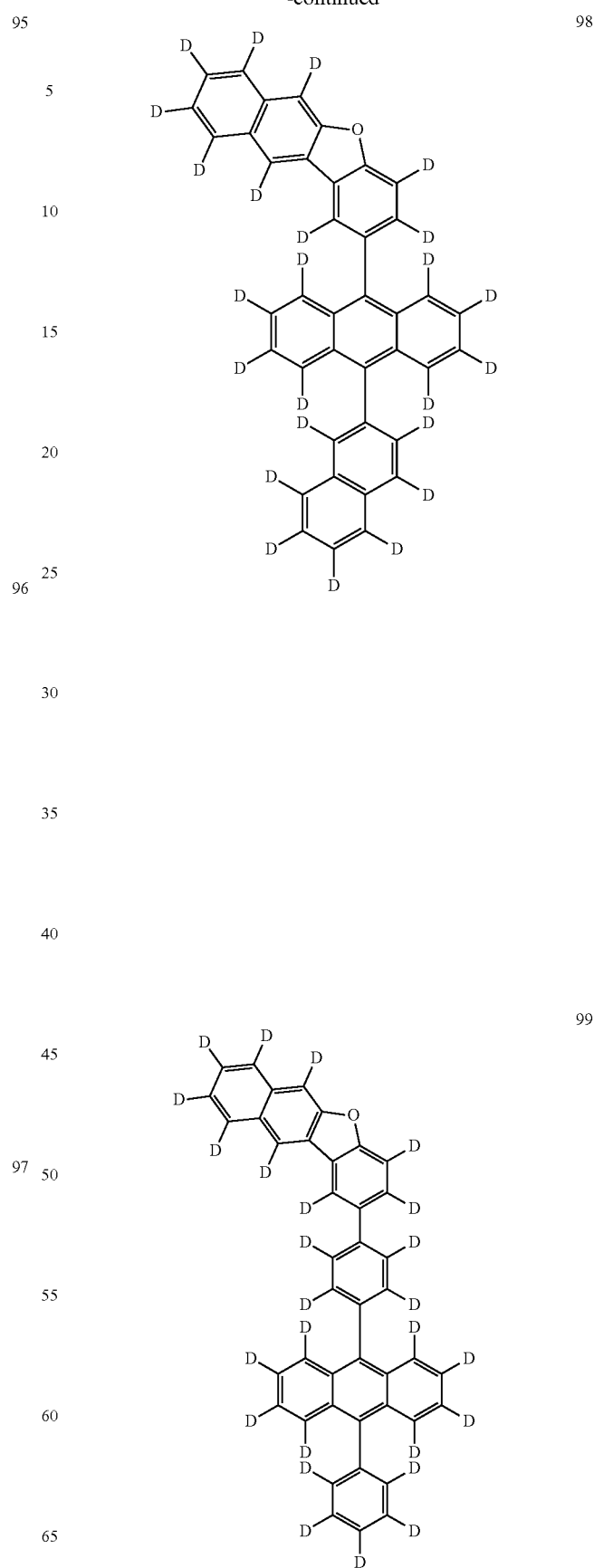

100
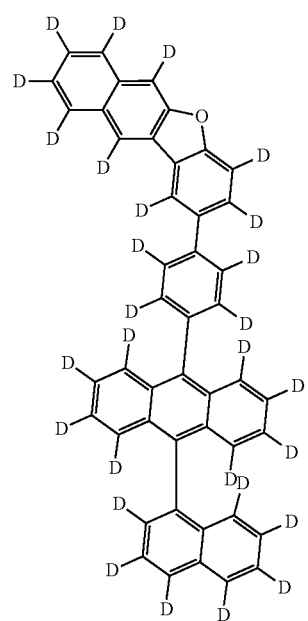
101
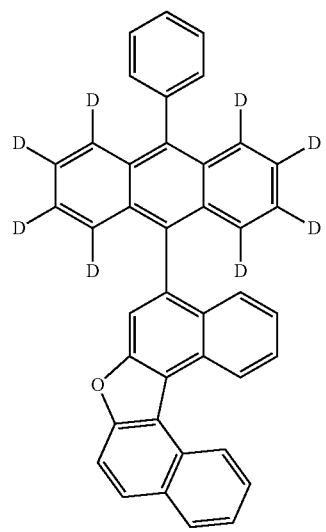
102
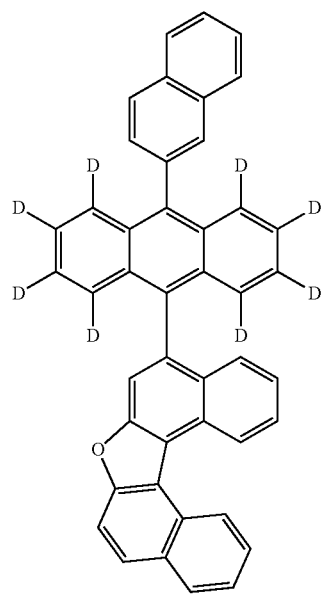
103
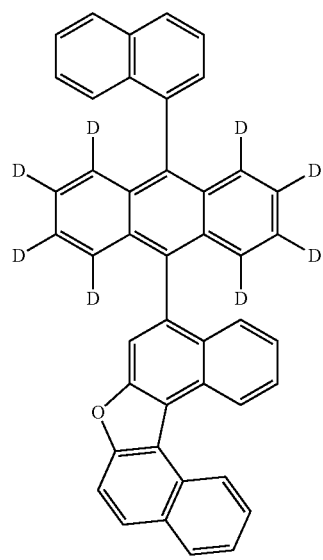

104

105

106

107

108
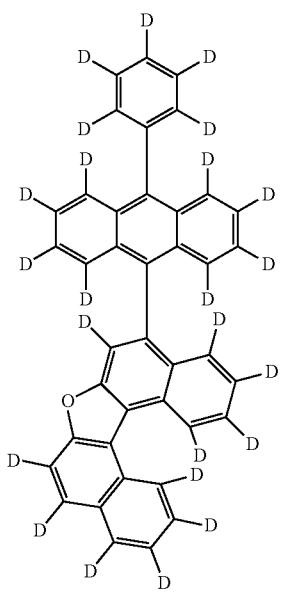
109
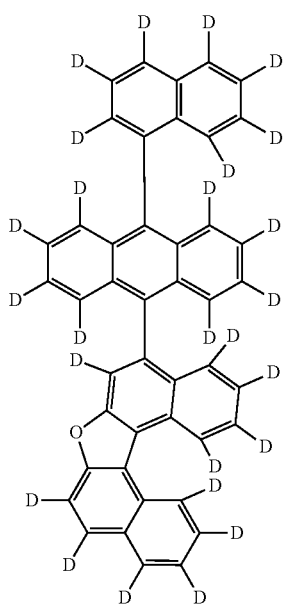
110
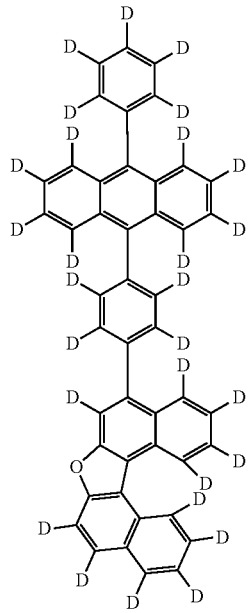
111
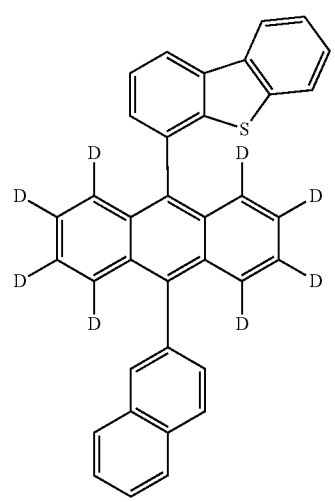
112
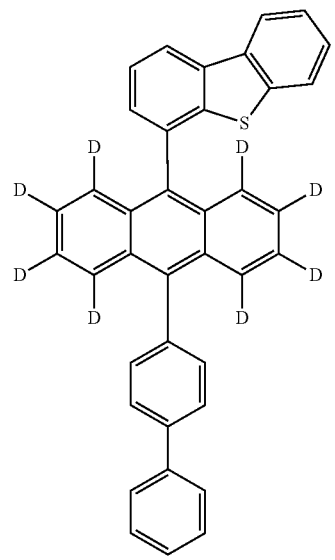

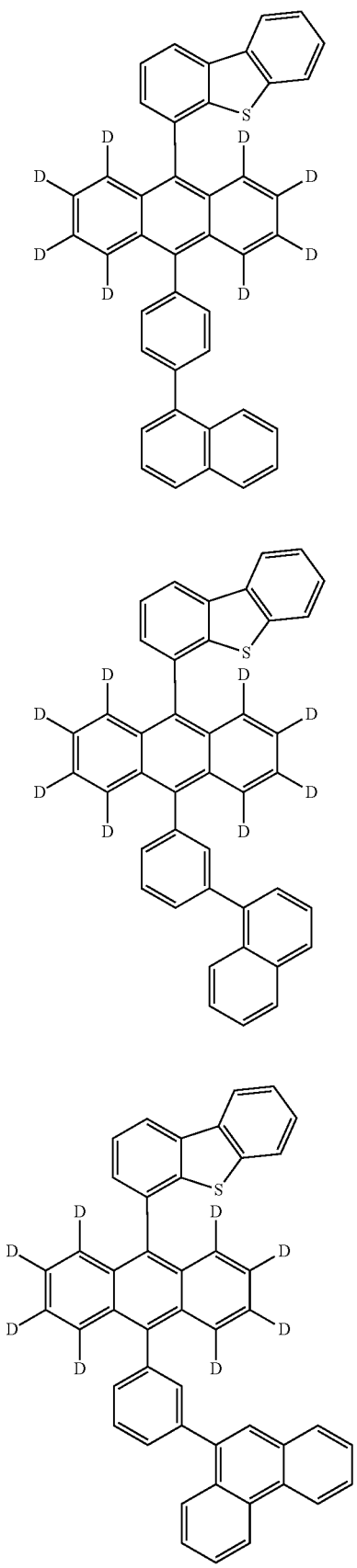
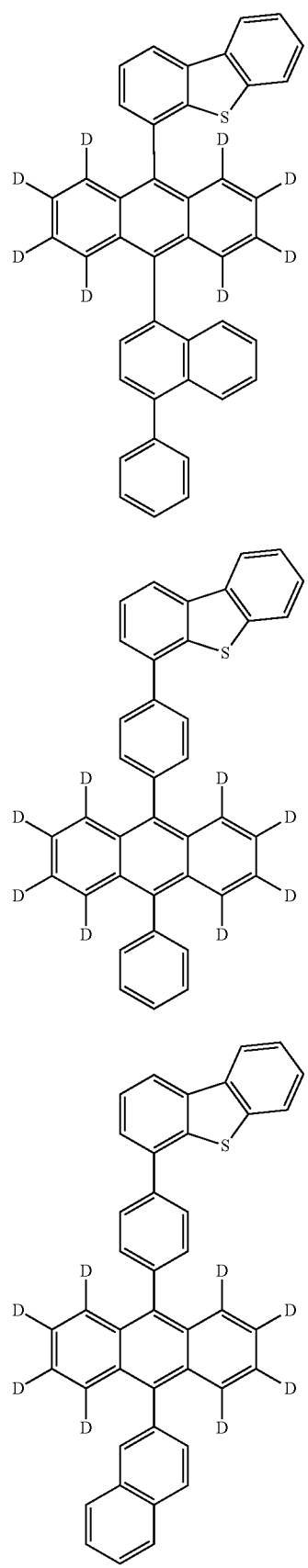

119
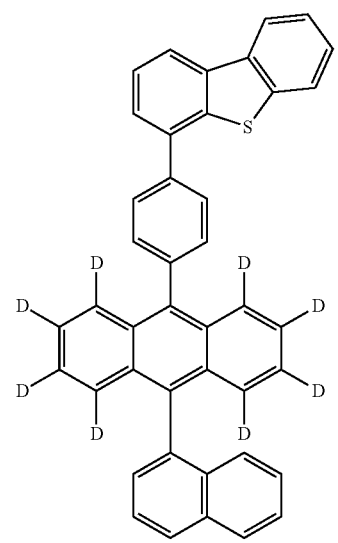
120
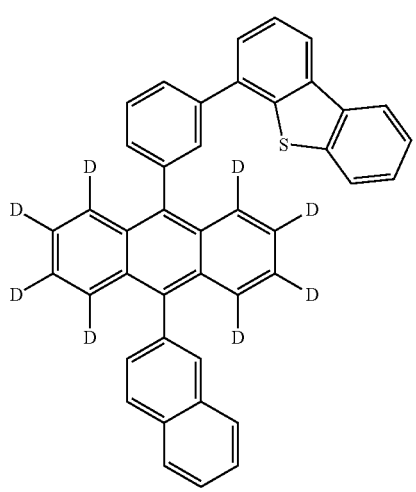
121
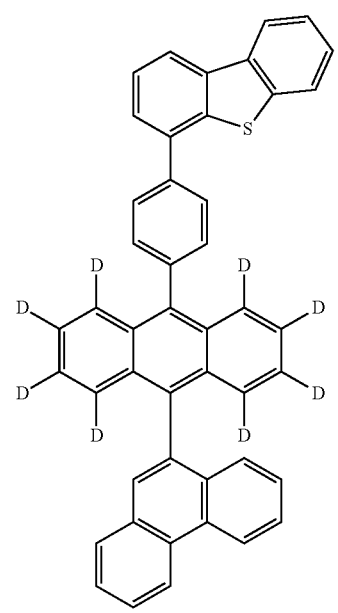
122
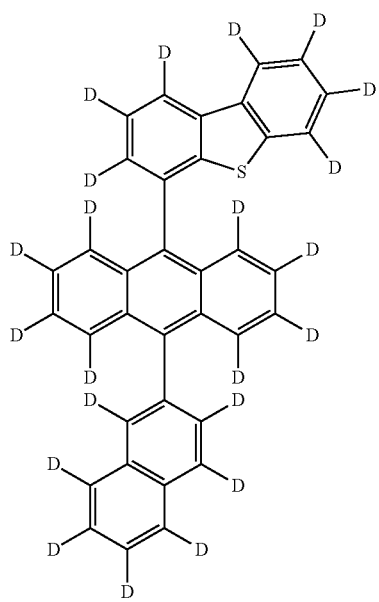
123
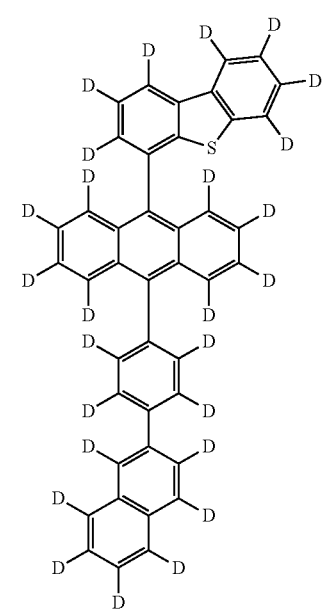

124
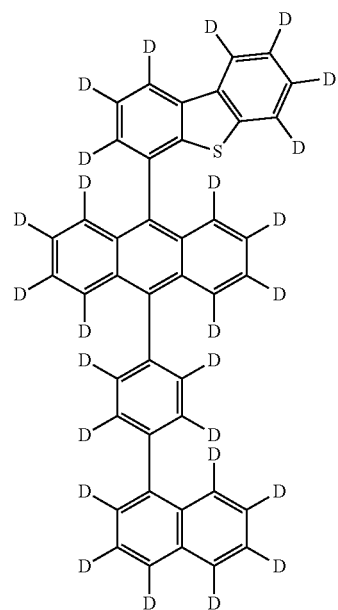
125
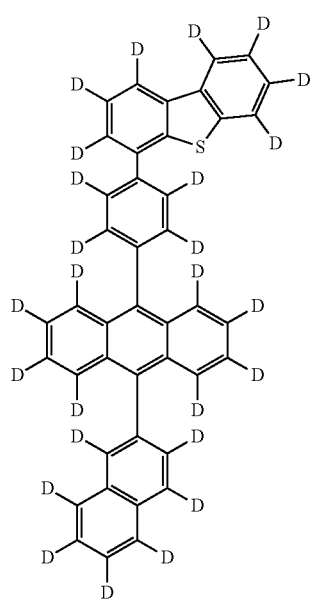
126
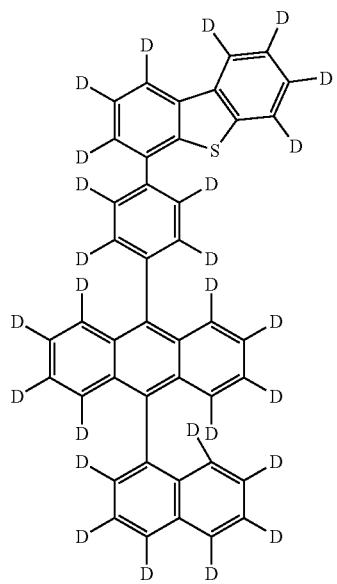
127
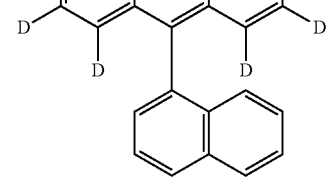

128
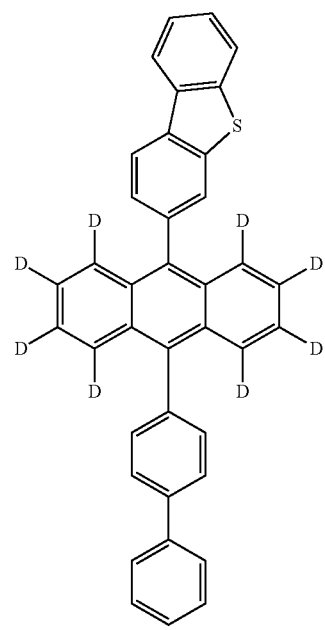
129
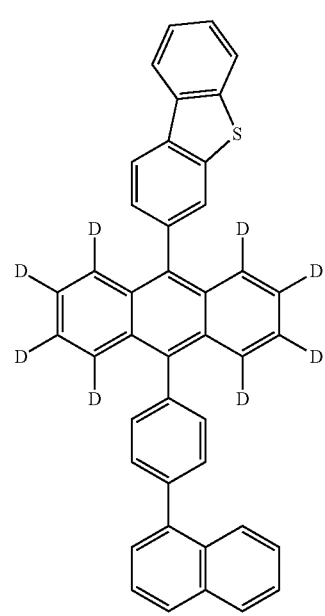
130
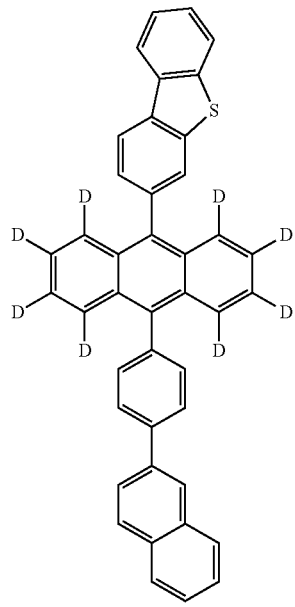
131
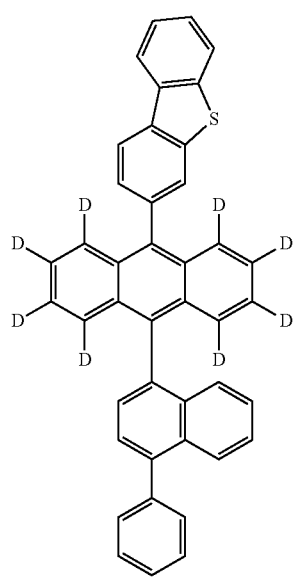

132
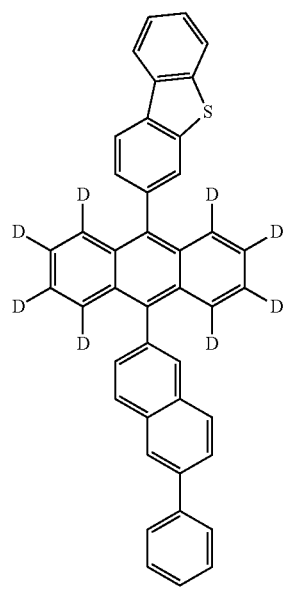
133
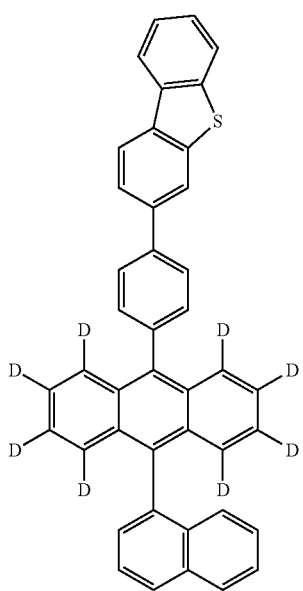
134
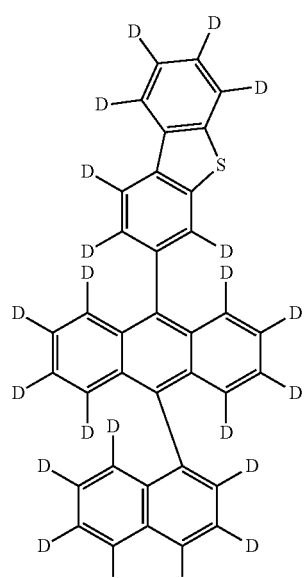
135
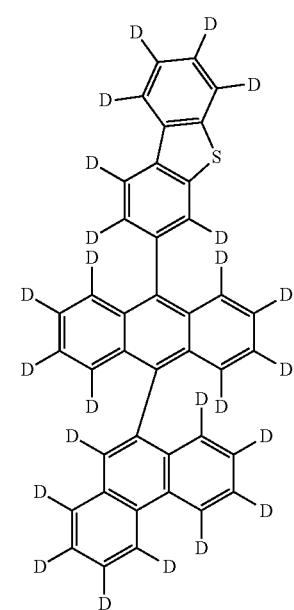

136
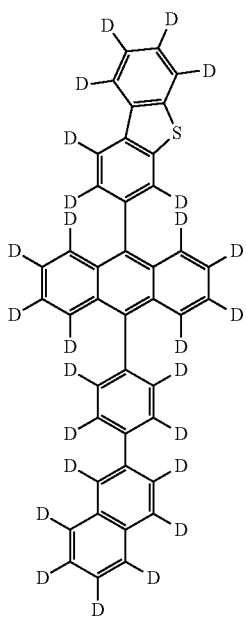
137
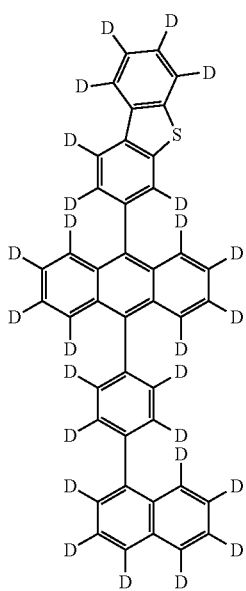
138
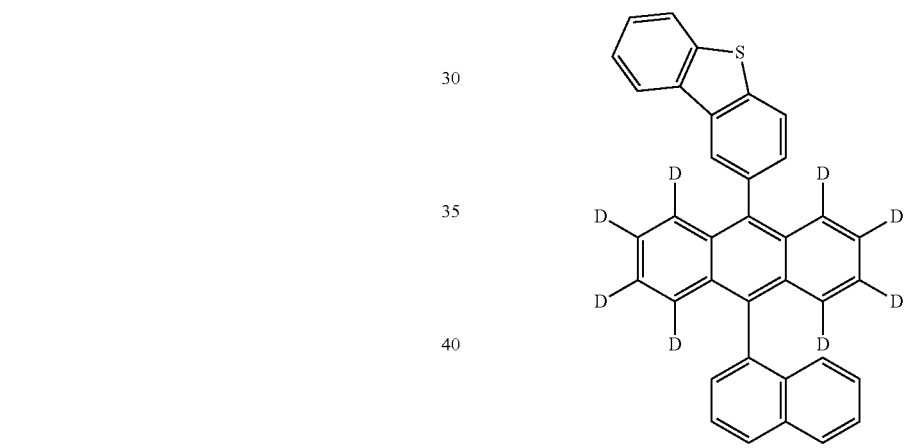
139
140
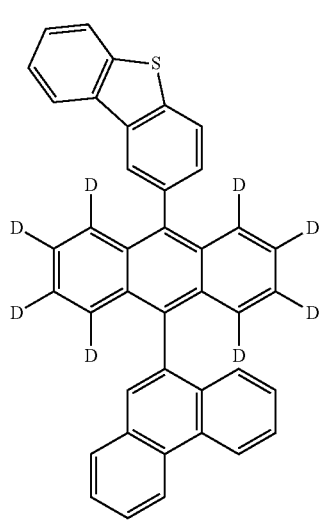

141
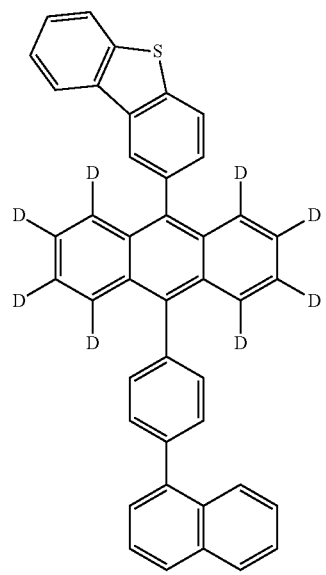
142
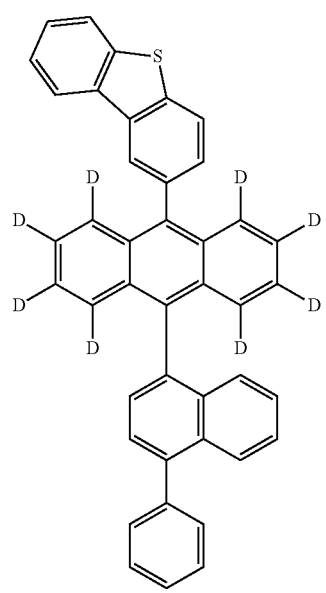
143
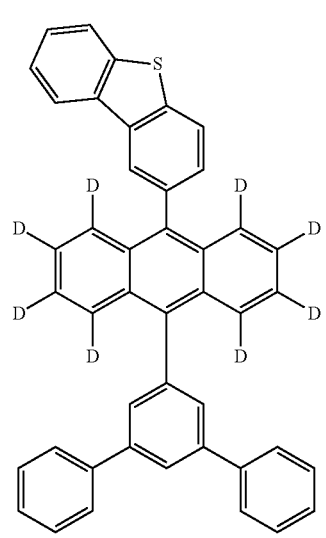
144
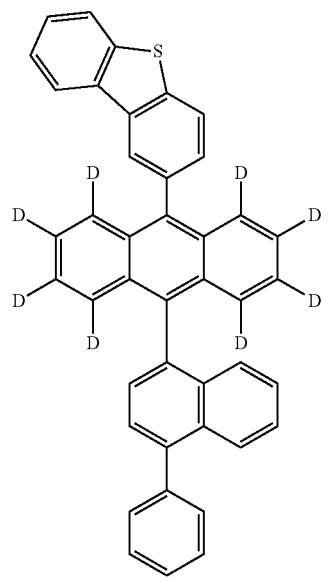
145
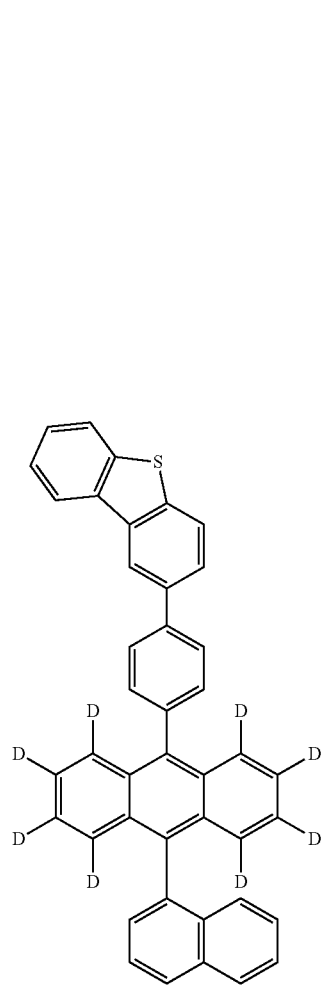

146
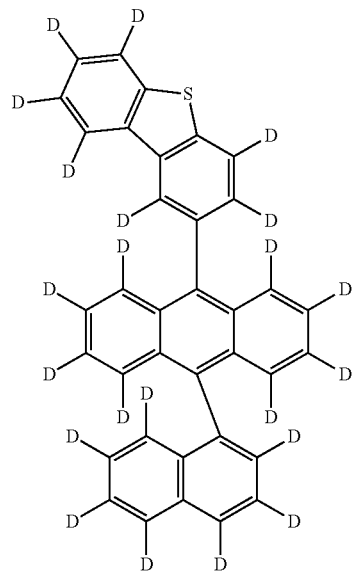
147
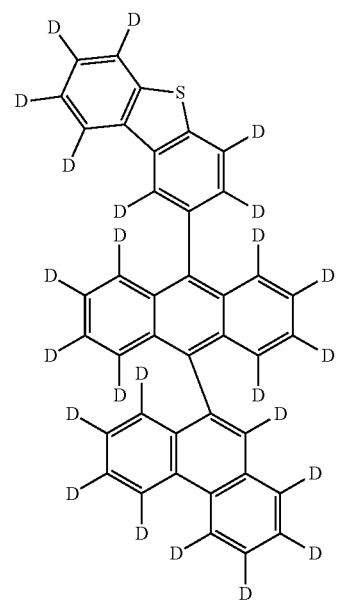
148
149

150
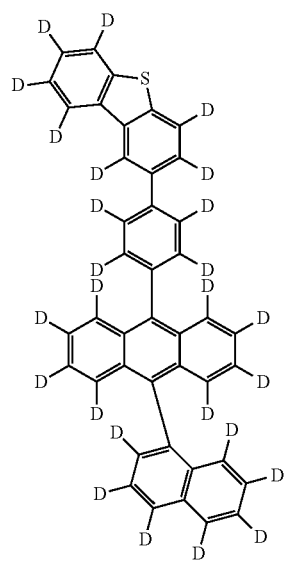
151
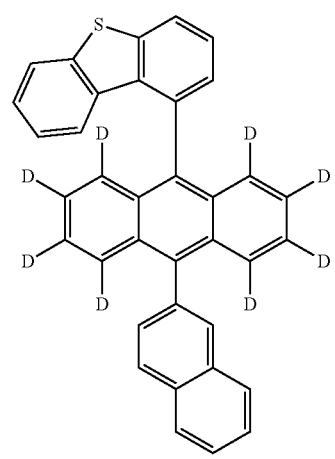
152
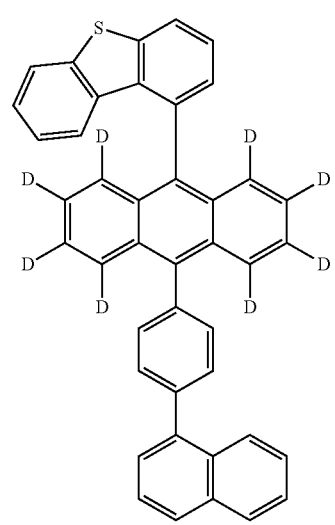
153
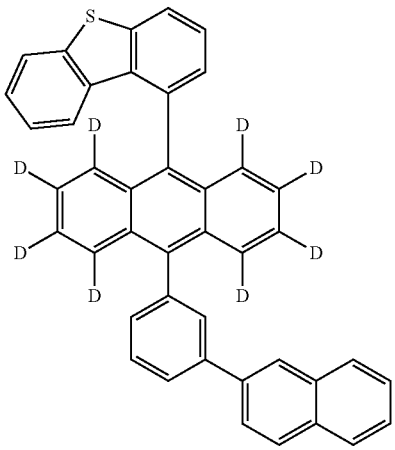
154
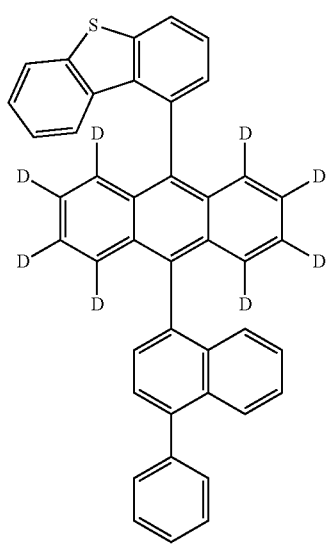
155
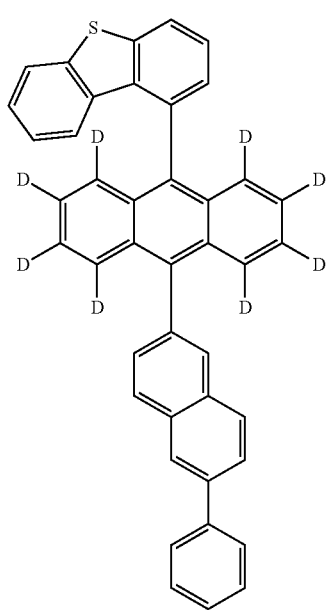

156
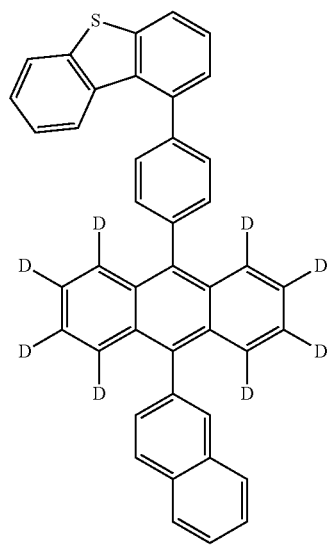
157
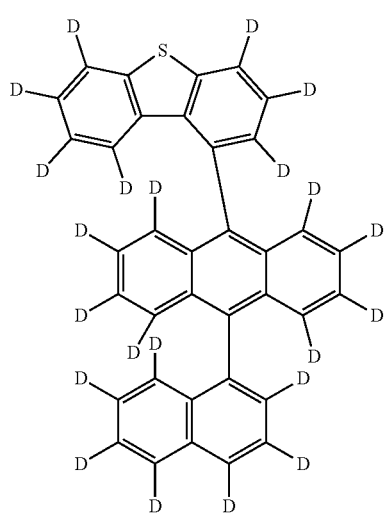
158
159
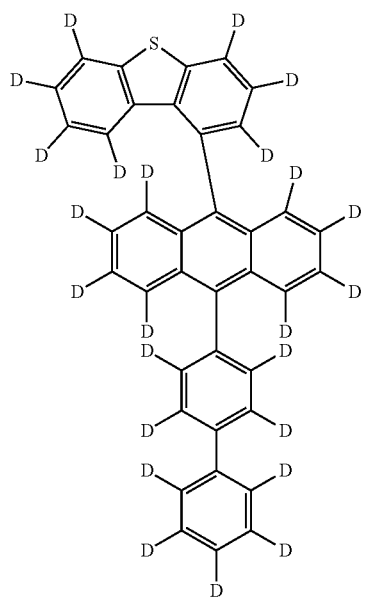
160
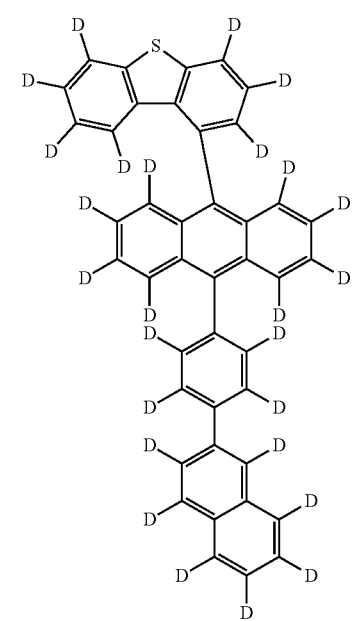

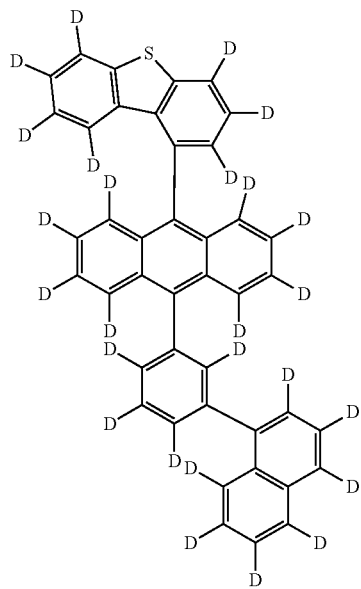
161
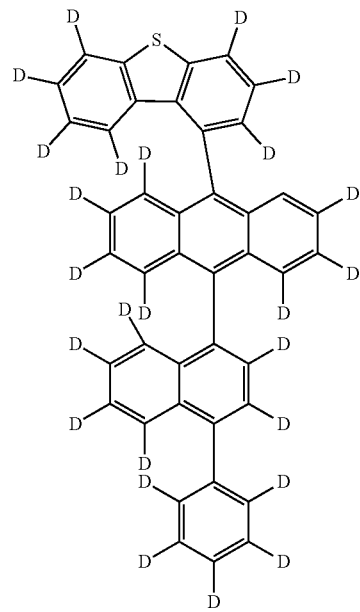
163
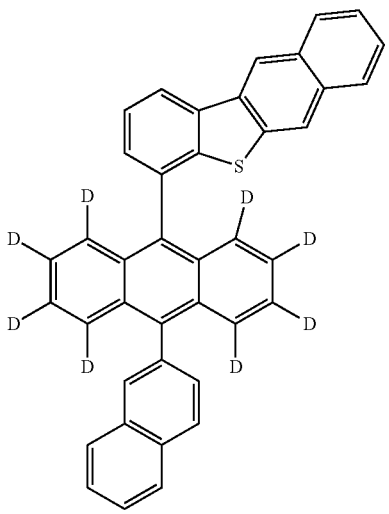
164

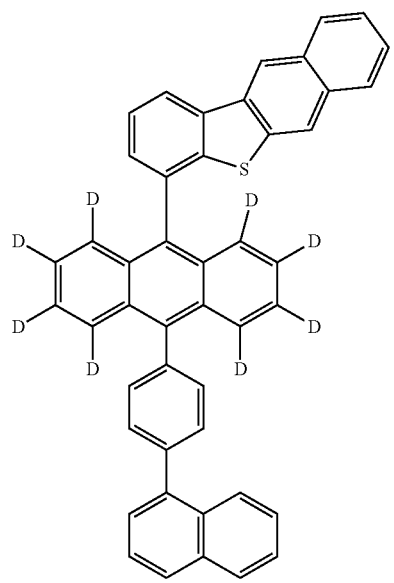
165
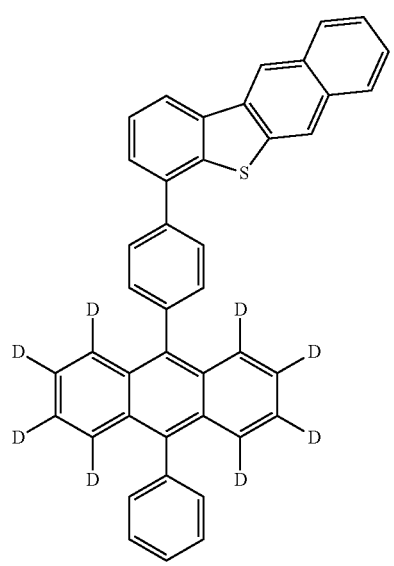
166
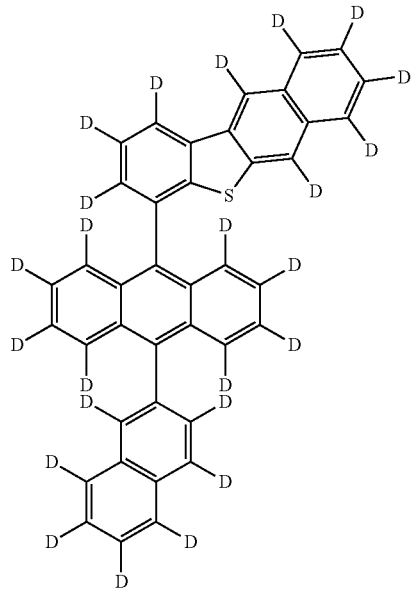
167
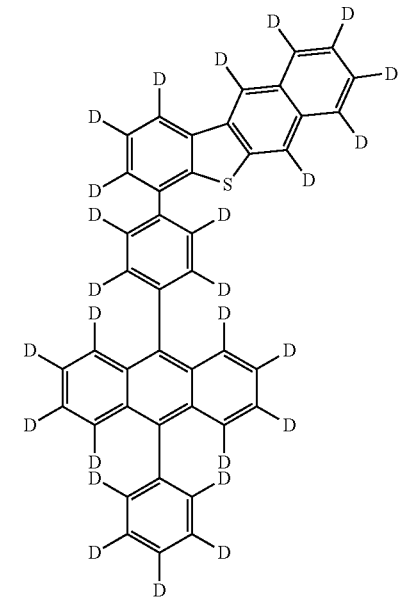
168

169
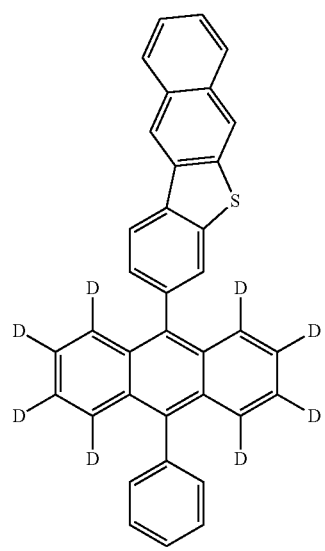
170
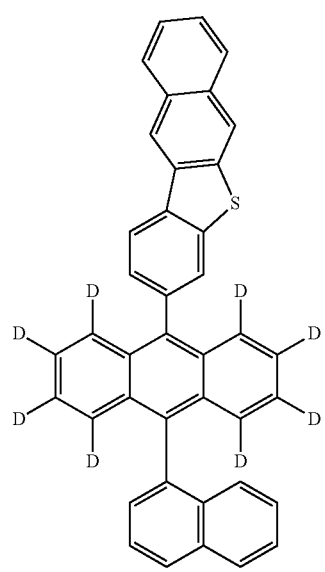
171
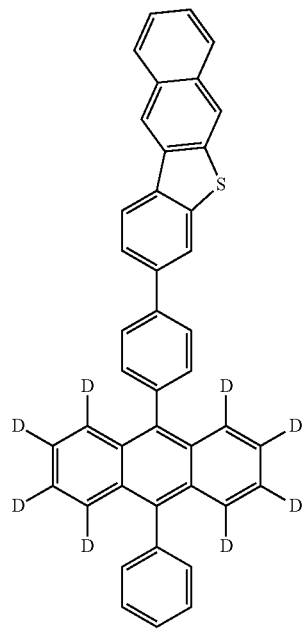
172
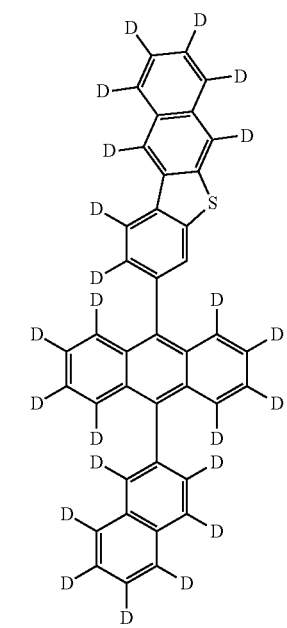

173
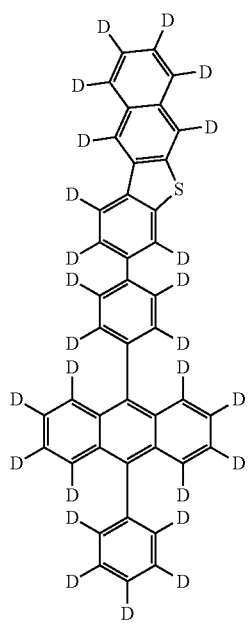
174
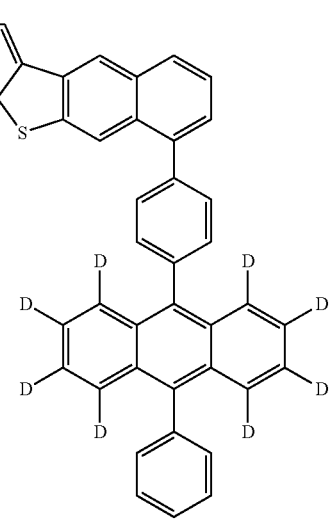
175
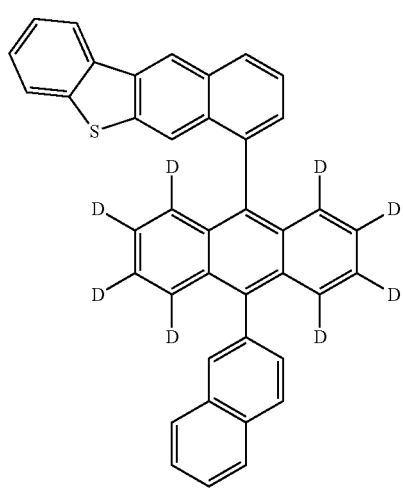
176
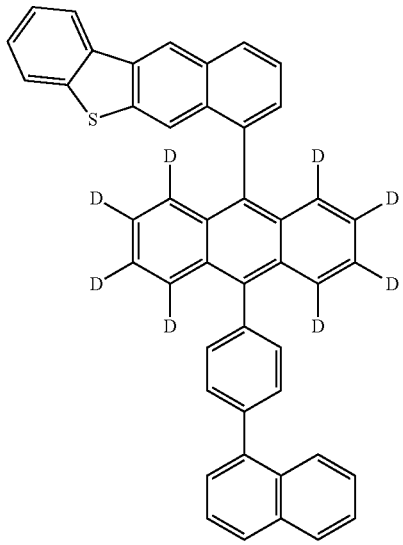
177
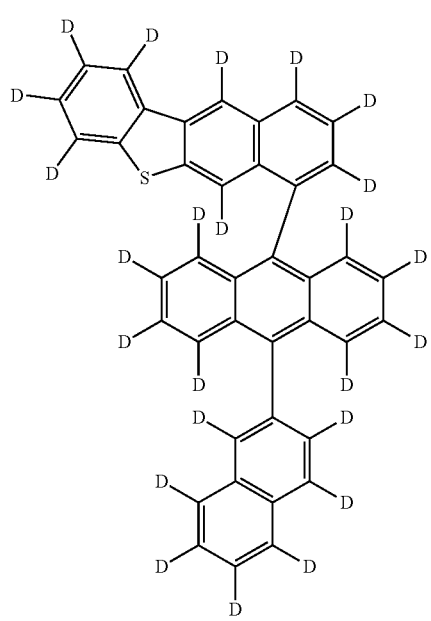

178
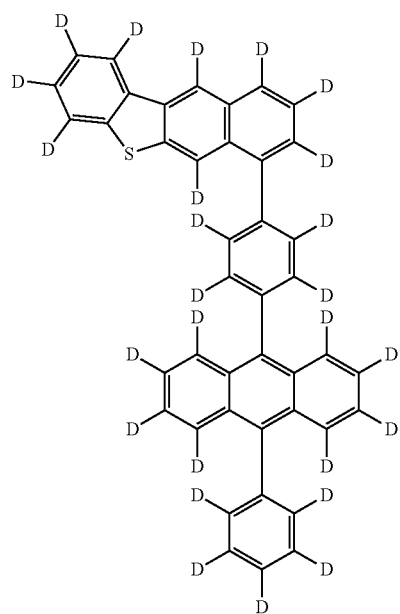
179
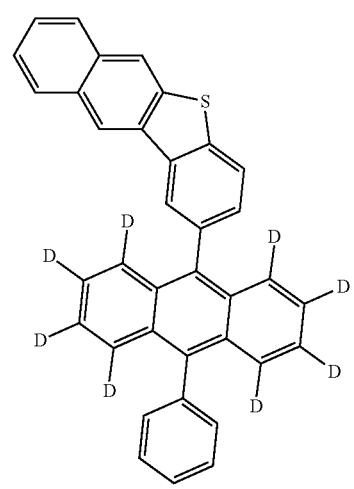
180
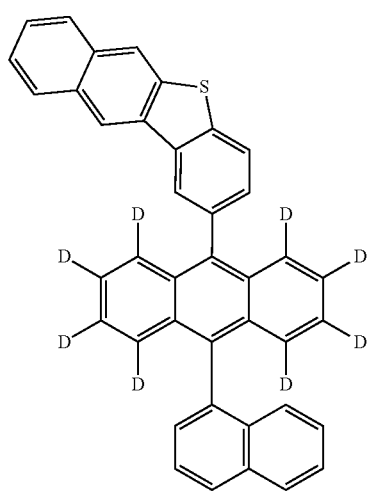
181
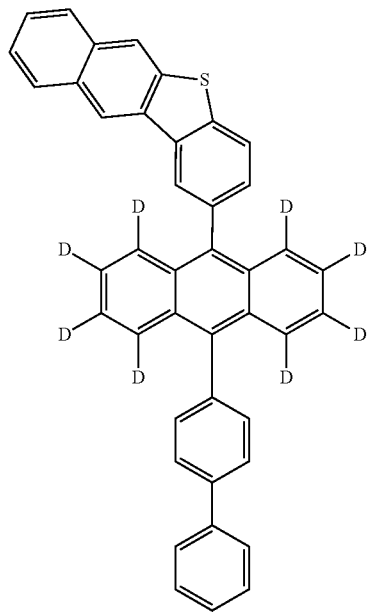
182
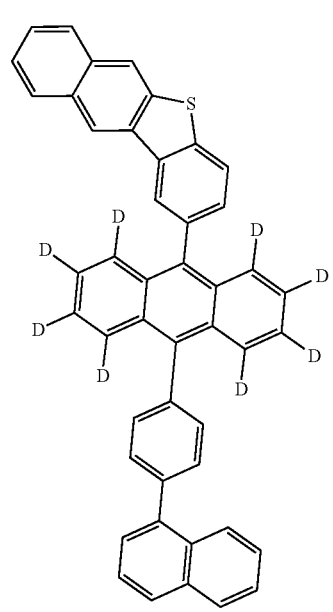

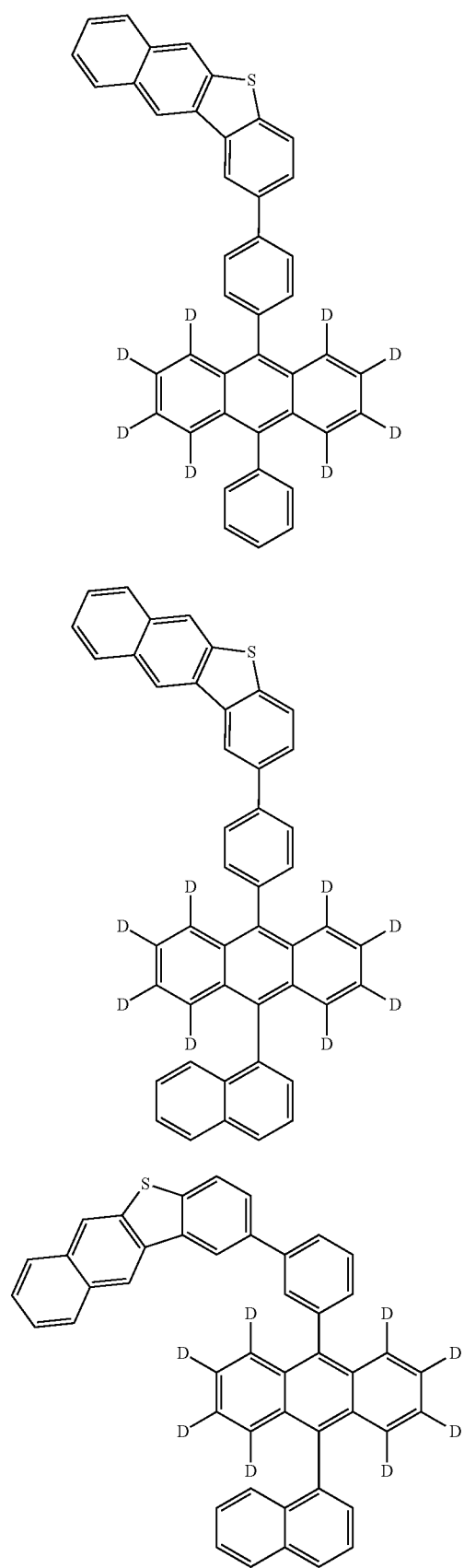
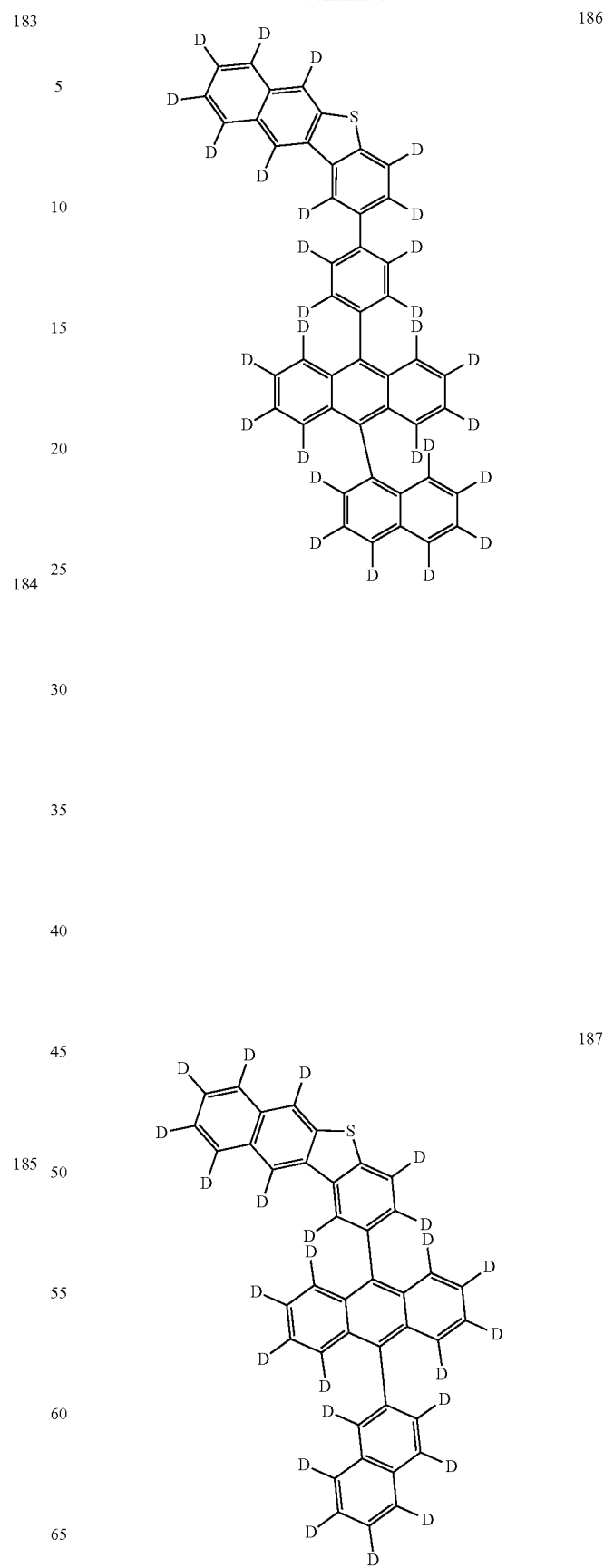

188
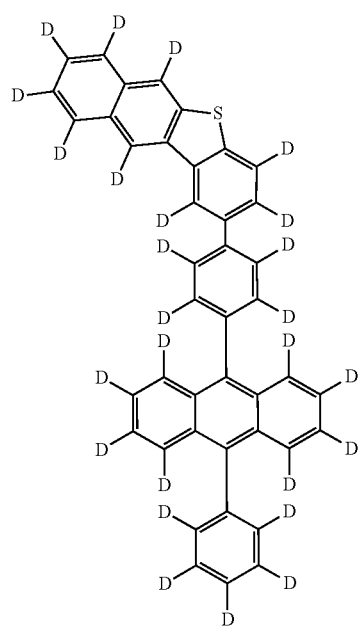
189
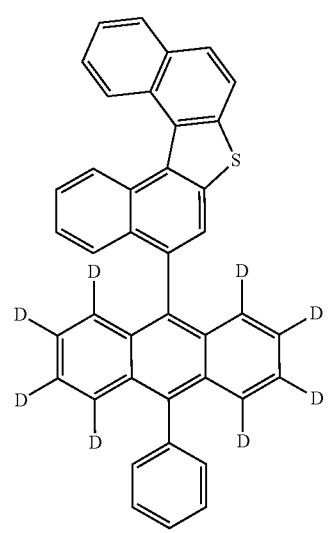
190
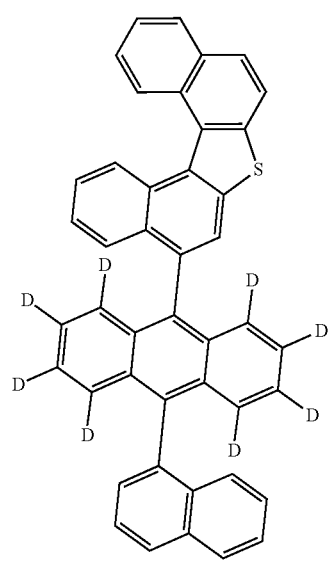
191
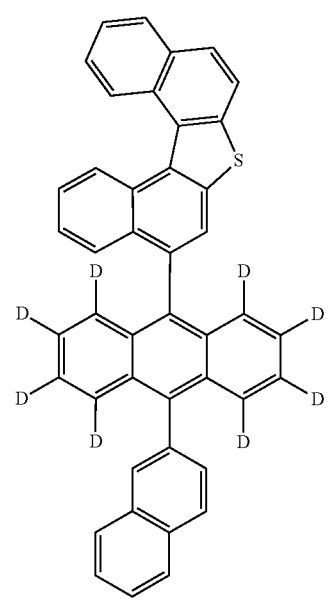

103
-continued
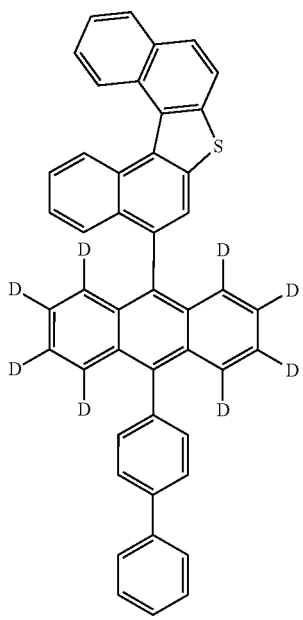
192
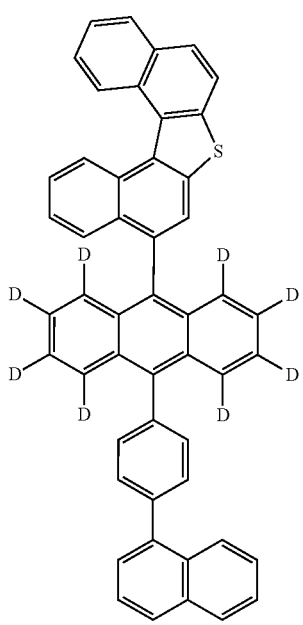
193
104
-continued
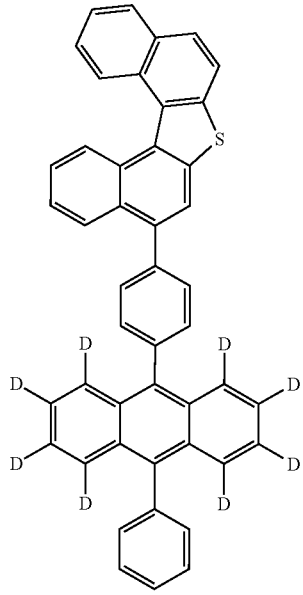
194
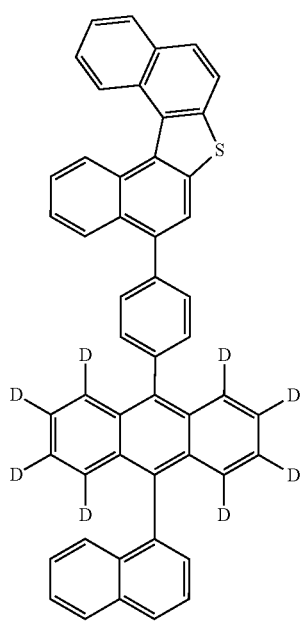
195

196
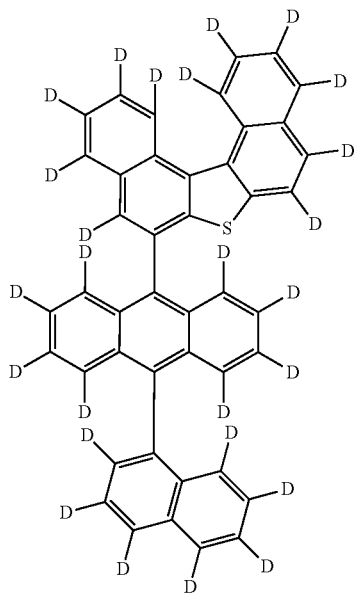
197
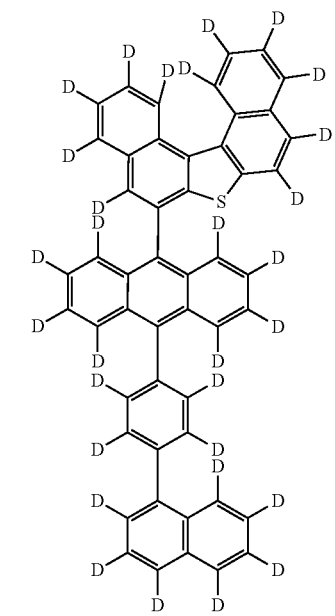
198
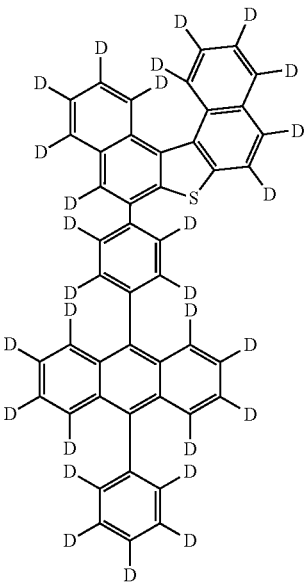
199
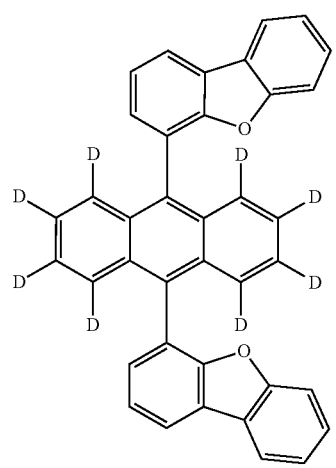
200
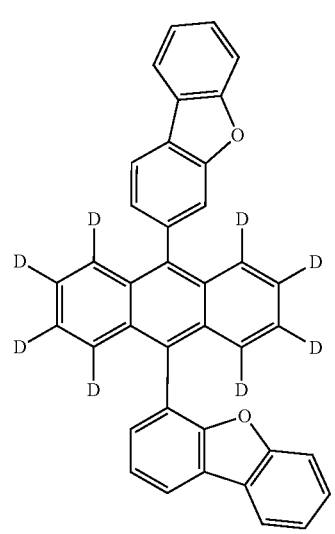

107
-continued
201
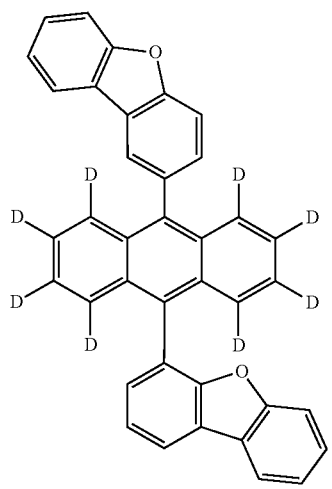
202
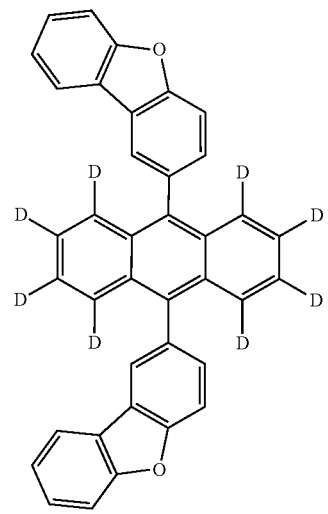
203
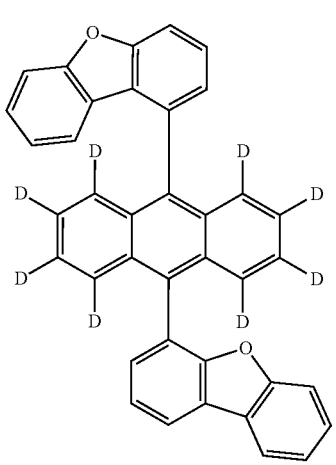
108
-continued
204
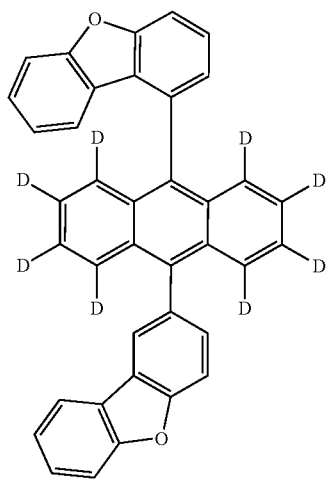
205
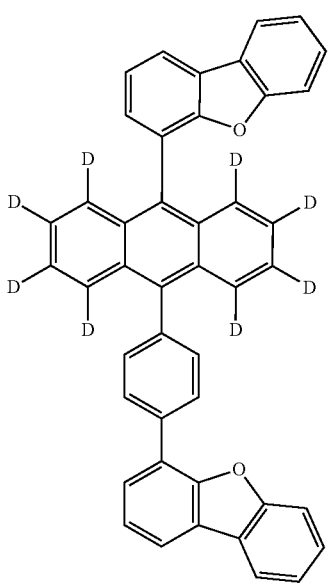
206
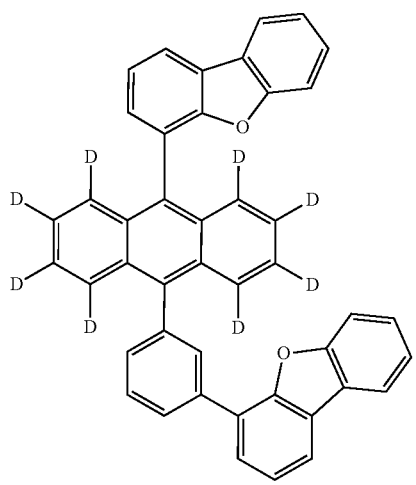

207
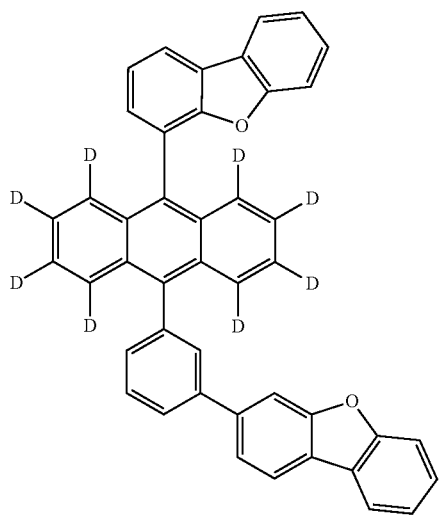
208
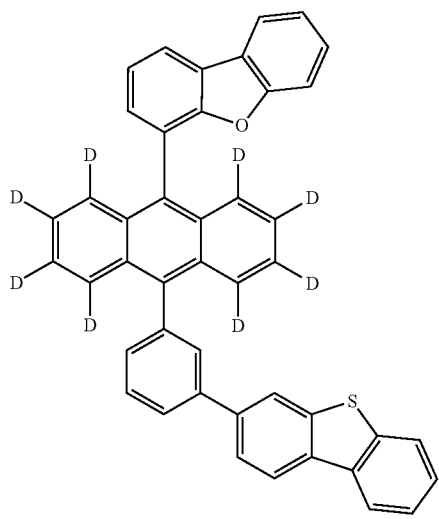
209
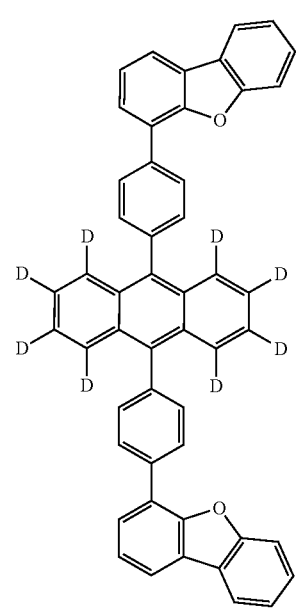
210
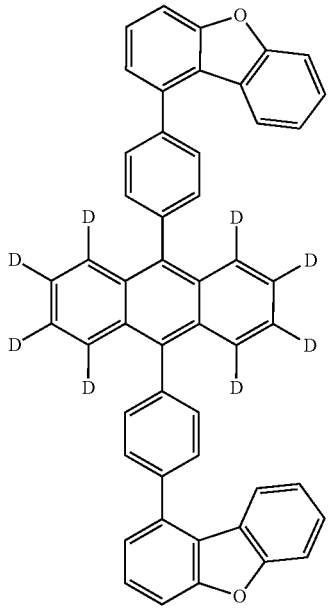
211
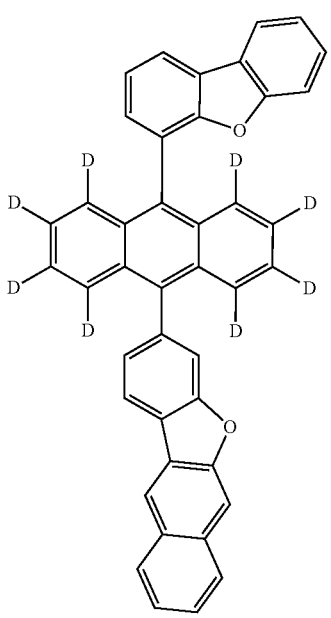

111
-continued
212
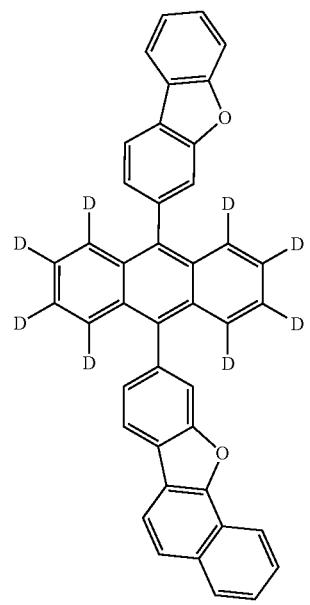
213
112
-continued
214
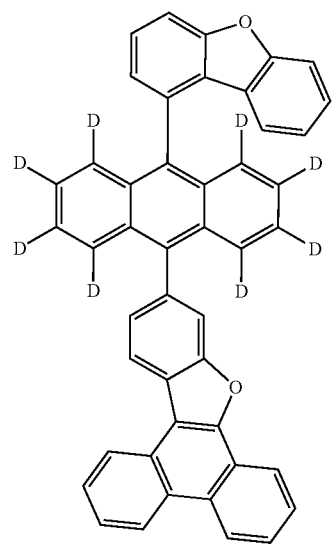
215
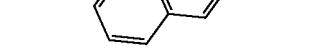

216
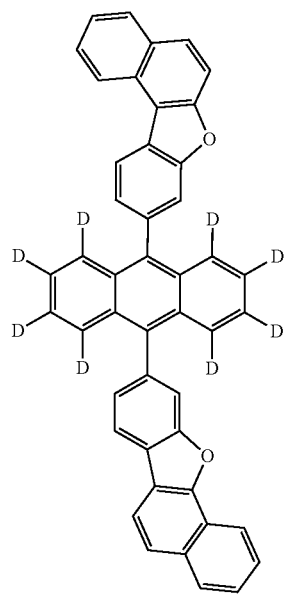
217
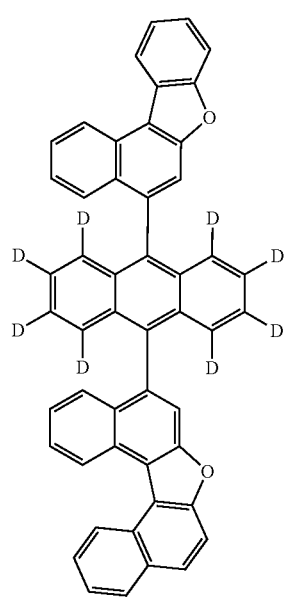
218
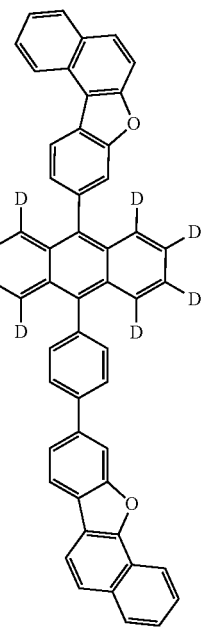
219
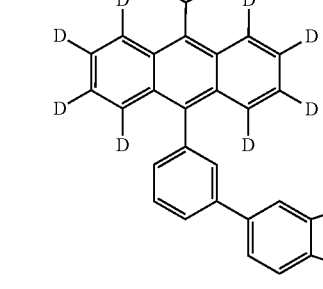

115
-continued
220
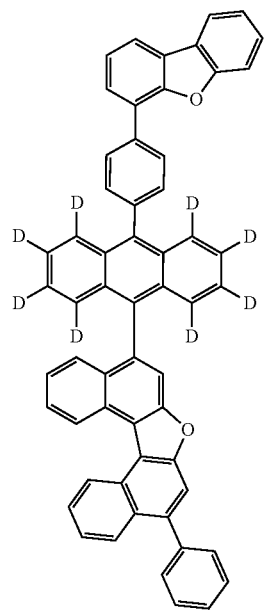
221
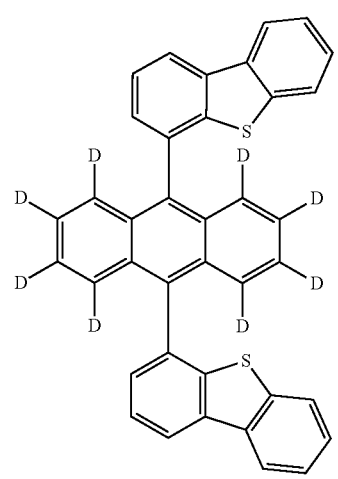
222
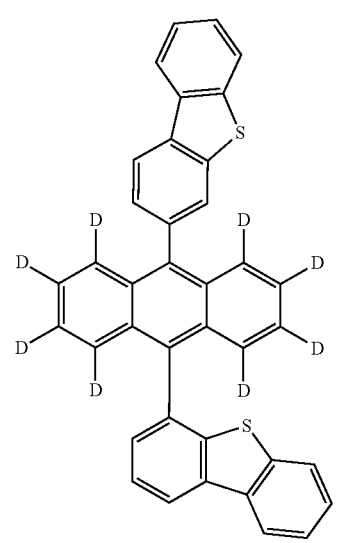
116
-continued
223
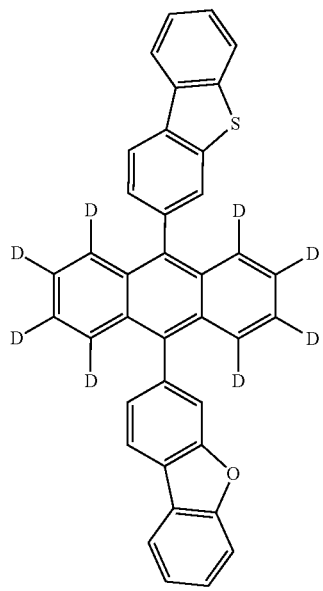
224
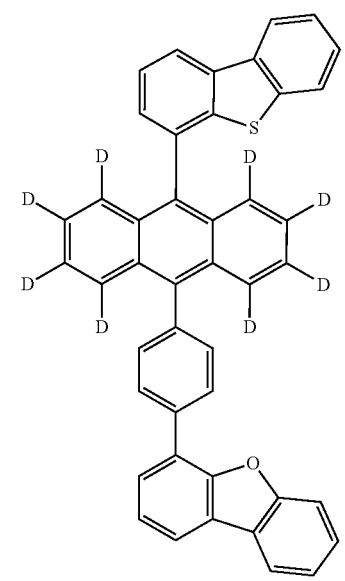

225
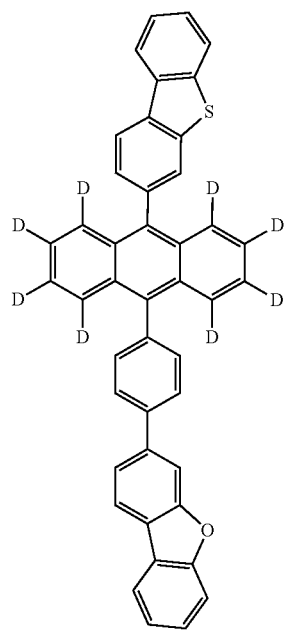
226
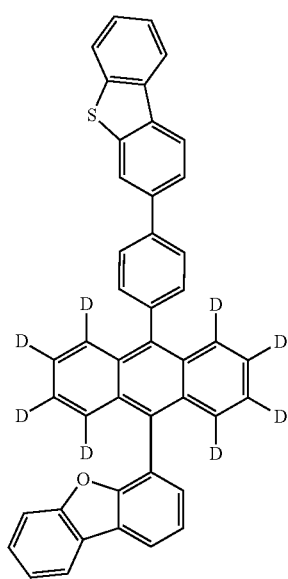
227
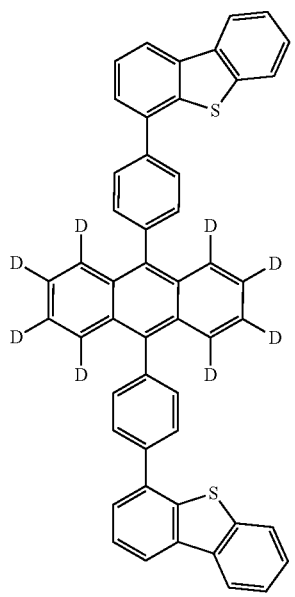
228
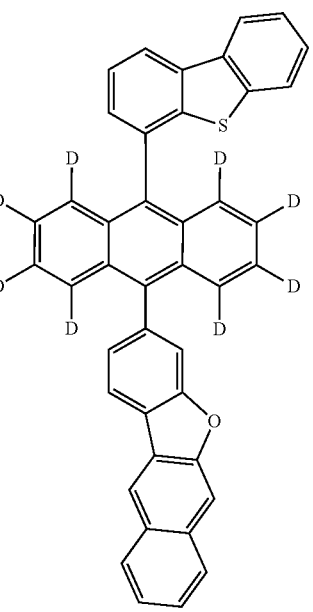

119 -continued
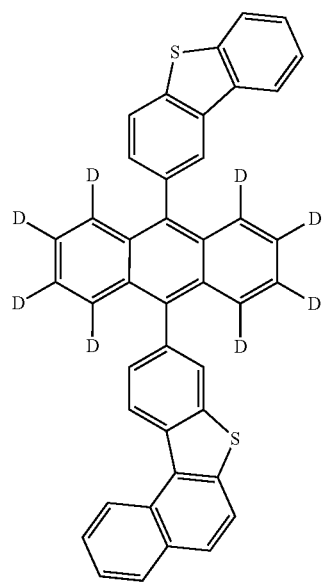
229
120 -continued
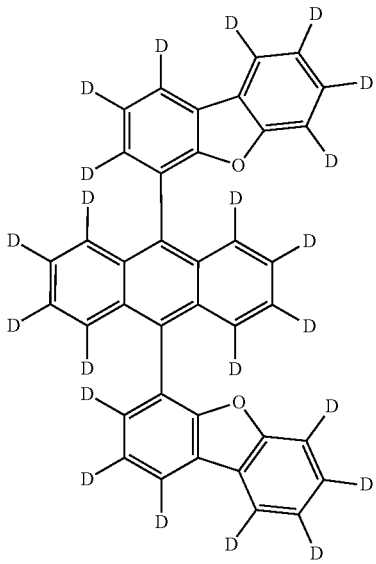
231
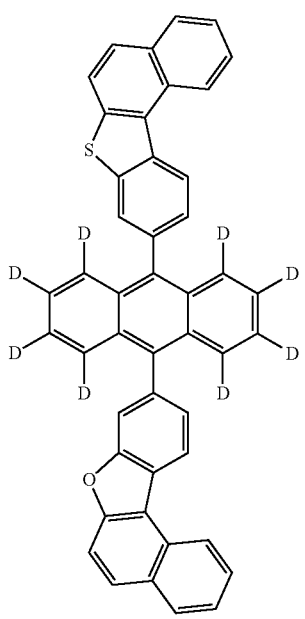
230
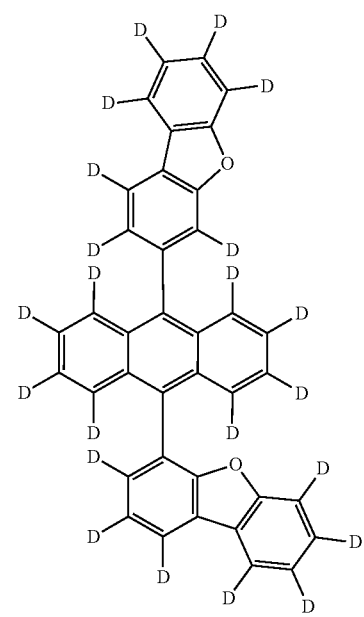
232

121
-continued
233
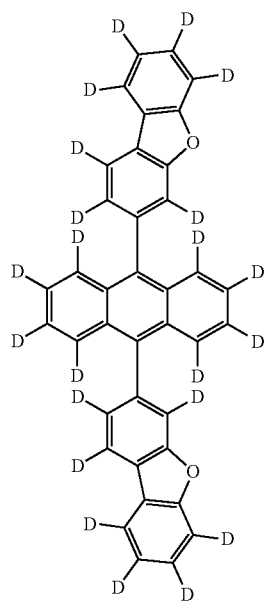
234
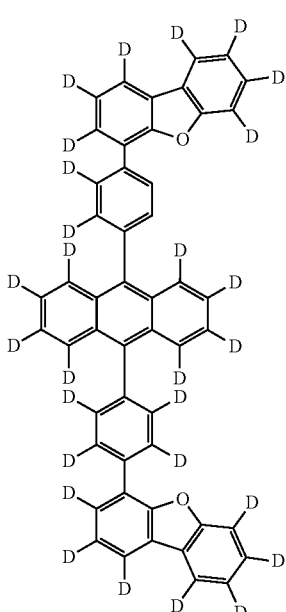
122
-continued
235
236
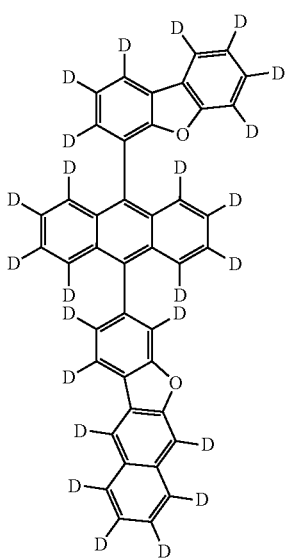

237
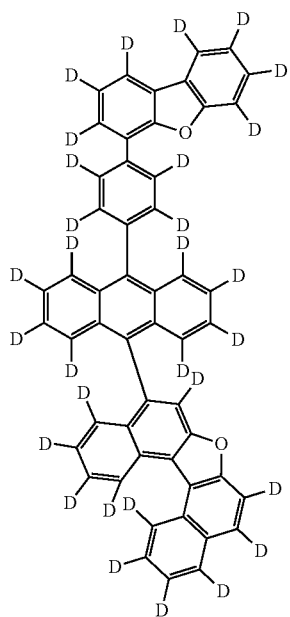
238
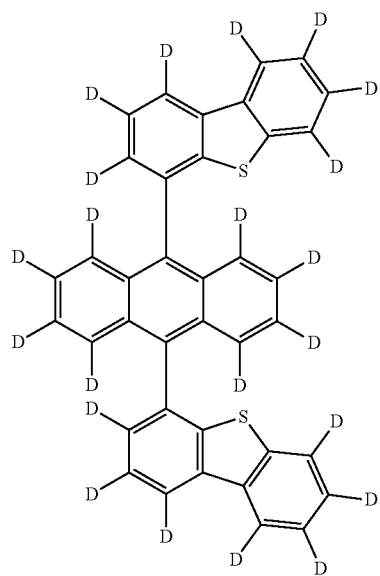
239
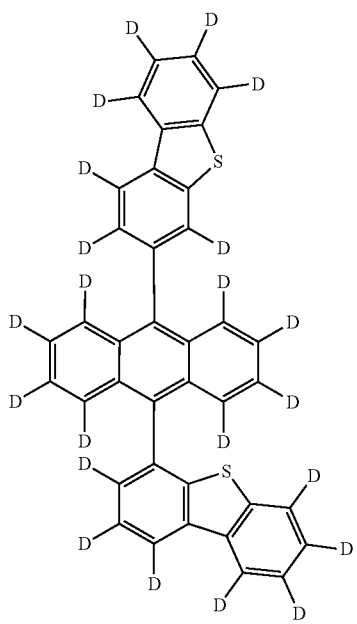
240
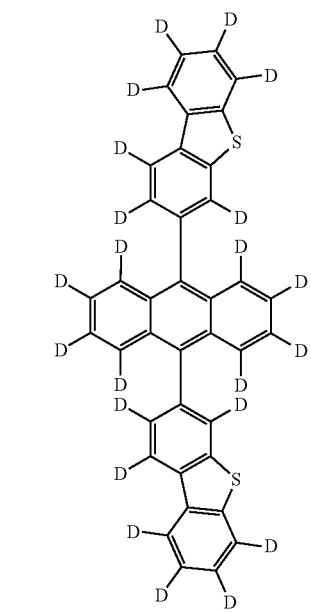

125
-continued

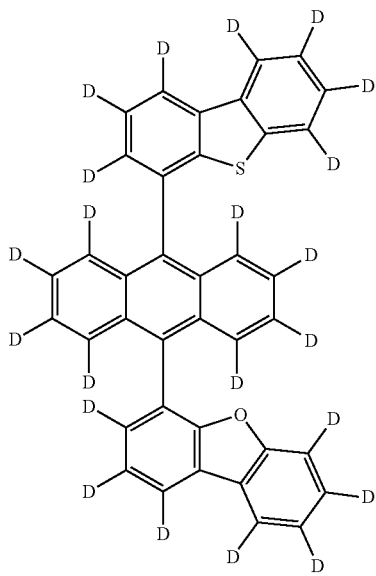
241

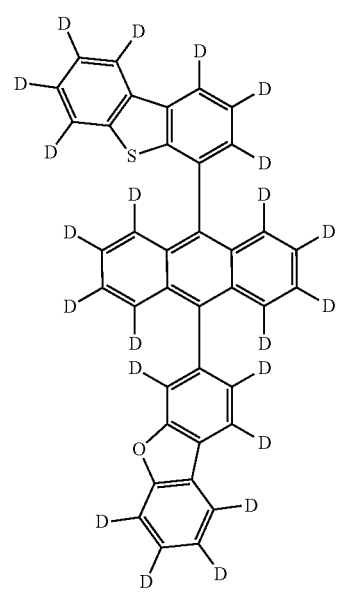
242

126
-continued

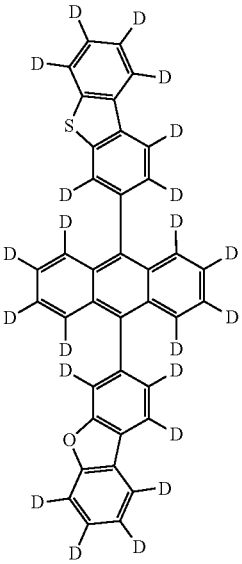
243

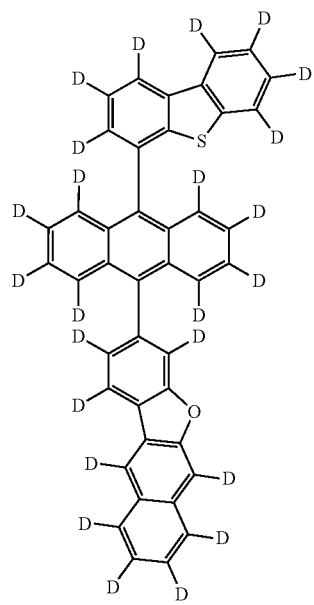
244

Hereinafter, methods for synthesizing the compounds represented by the Chemical Formulas 1 and 2 will be described below as a representative example.

However, the methods for synthesizing the compounds in accordance with the present disclosure is not limited to following exemplified methods. The compounds in accordance with the present disclosure may be prepared by methods illustrated below and

Synthesis Example 1: Synthesis of Compound 6

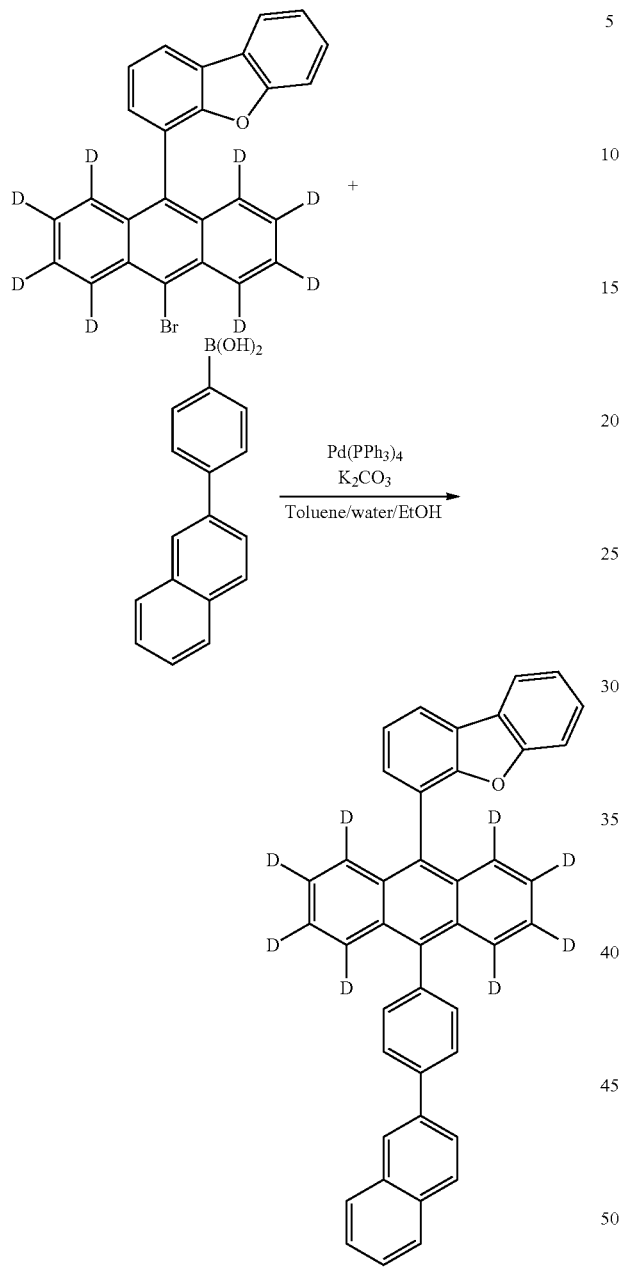

4-(10-bromoanthracene-9-yl)dibenzofuran-d8 (5.54 g, 10.0 mmol), (4-(naphthalen-1-yl)phenyl)boronic acid (2.73 g, 11.0 mmol), potassium carbonate (5.16 g, 20 mmol), 100 mL of toluene, 20 mL of water and 100 mL of ethanol were mixed with each other.

Then, tetrakis(triphenylphosphine)palladium (0.231 g, 0.20 mmol) was added to the mixture which in turn was refluxed for 10 hours. Thereafter, the resulting mixture was cooled to a room temperature, and then water was added thereto. A layer separation was performed to obtain an organic layer. The organic layer was treated with $MgSO_4$ to remove moisture therefrom.

After filtration of the organic layer, filtrate was concentrated under a reduced pressure. The concentrate was subjected to column chromatography using dichloromethane and n-hexane as a developing solvent to obtain 3.38 g (yield: 25%) of the present compound 6.

MS (MALDI-TOF) m/z: 554 [M]+

Synthesis Example 2: Synthesis of Compound 7

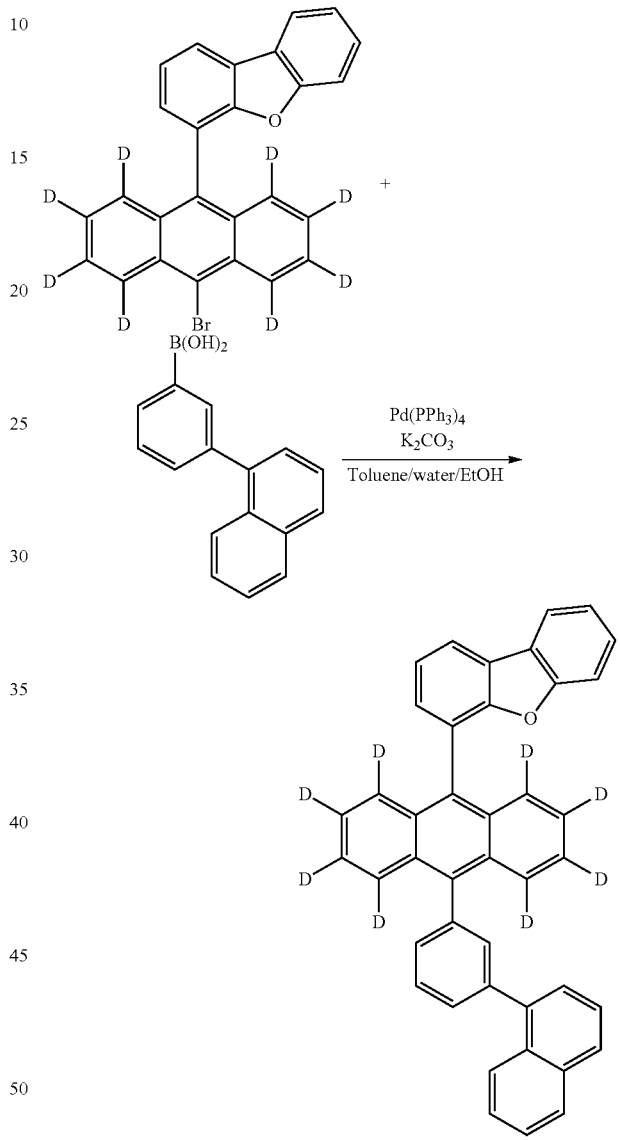

4-(10-bromoanthracene-9-yl)dibenzofuran-d8 (5.54 g, 10.0 mmol), (3-(naphthalen-1-yl)phenyl)boronic acid (2.73 g, 11.0 mmol), potassium carbonate (5.16 g, 20 mmol), 100 mL of toluene, 20 mL of water and 100 mL of ethanol were mixed with each other.

Then, tetrakis(triphenylphosphine)palladium (0.231 g, 0.20 mmol) was added to the mixture which in turn was refluxed for 10 hours. Thereafter, the resulting mixture was cooled to a room temperature, and then water was added thereto. A layer separation was performed to obtain an organic layer. The organic layer was treated with $MgSO_4$ to remove moisture therefrom.

After filtration of the organic layer, filtrate was concentrated under a reduced pressure. The concentrate was subjected to column chromatography using dichloromethane and n-hexane as a developing solvent to obtain 3.38 g (yield: 61%) of the present compound 7.

MS (MALDI-TOF) m/z: 554 [M]$^+$

Synthesis Example 3: Synthesis of Compound 1

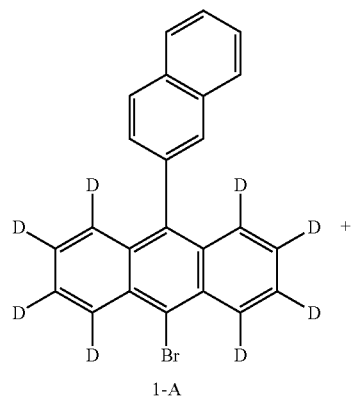

1-A

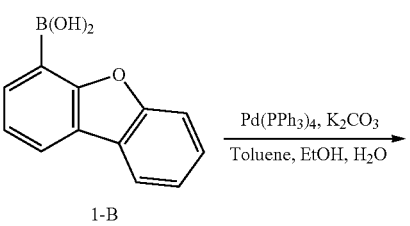

1-B

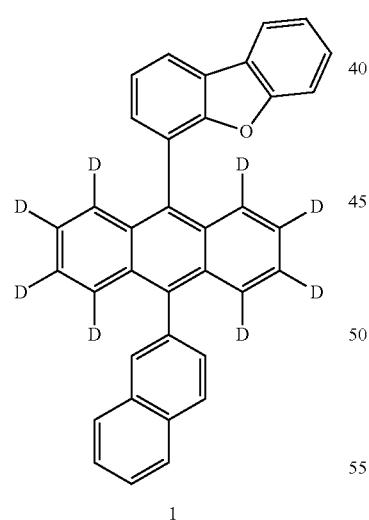

1

A starting material 1-A 3.92 g (10 mmol), a starting material 1-B 2.33 g (11 mmol), potassium carbonate (5.16 g, 20 mmol), 100 mL of toluene, 20 mL of water and 100 mL of ethanol were mixed with each other.

Then, tetrakis(triphenylphosphine)palladium (0.231 g, 0.20 mmol) was added to the mixture which in turn was refluxed for 10 hours. Thereafter, the resulting mixture was cooled to a room temperature, and then water was added thereto. A layer separation was performed to obtain an organic layer. The organic layer was treated with MgSO$_4$ to remove moisture therefrom.

After filtration of the organic layer, filtrate was concentrated under a reduced pressure. The concentrate was subjected to column chromatography using dichloromethane and n-hexane as a developing solvent to obtain 1 g (yield: 62%) of the present compound 1.

MS (MALDI-TOF) m/z: 478 [M]$^+$

Synthesis Example 4: Synthesis of Compound 3

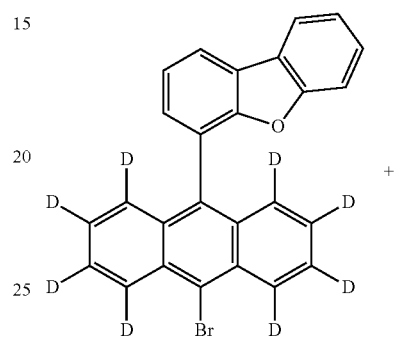

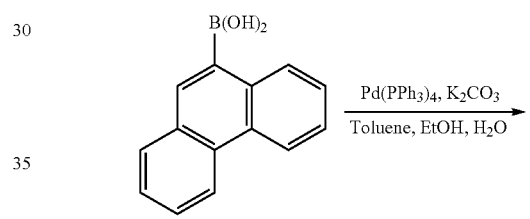

3-B

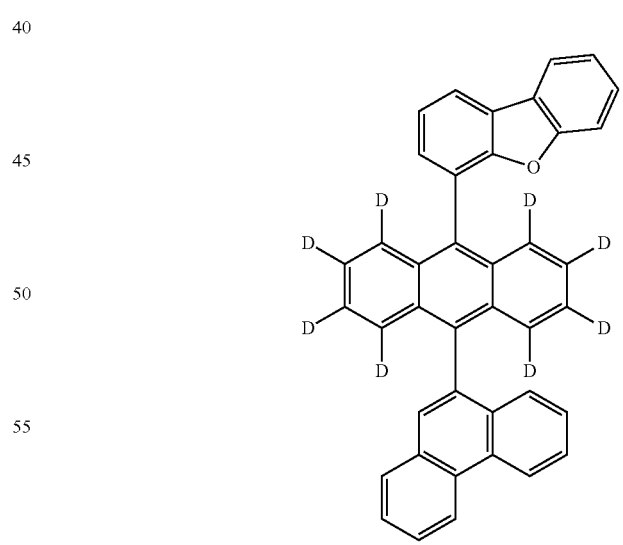

3

2.7 g (yield 51%) of the present compound 3 was obtained using the same manner as in Synthesis Example 1 except that 2.44 g (11 mmol) of a starting material 3-B was used instead of (4-(naphthalen-1-yl)phenyl)boronic acid.

MS (MALDI-TOF) m/z: 528 [M]$^+$

Synthesis Example 5: Synthesis of Compound 5

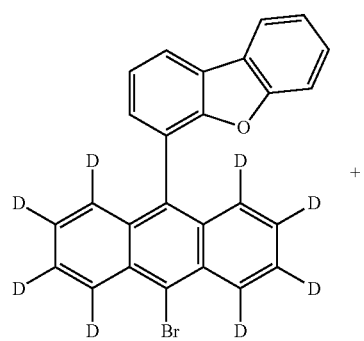

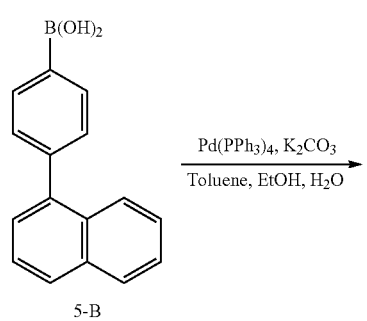

3.66 g (yield 66%) of the present compound 5 was obtained using the same manner as in Synthesis Example 1 except that 2.73 g (11 mmol) of a starting material 5-B was used instead of (4-(naphthalen-1-yl)phenyl)boronic acid.

MS (MALDI-TOF) m/z: 554 [M]⁺

Synthesis Example 6: Synthesis of Compound 9

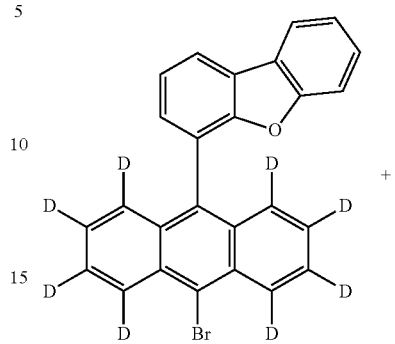

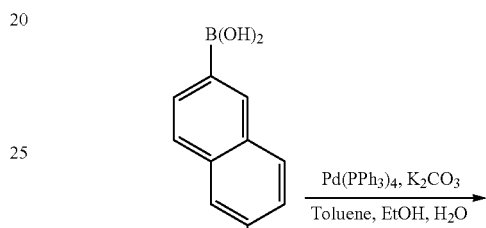

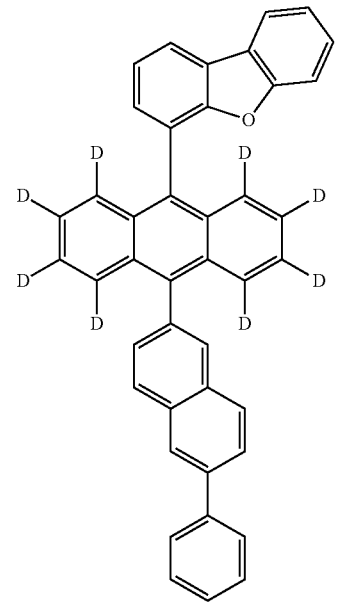

3.5 g (yield 63%) of the present compound 9 was obtained using the same manner as in Synthesis Example 1 except that 2.44 g (11 mmol) of a starting material 9-B was used instead of (4-(naphthalen-1-yl)phenyl)boronic acid.

Synthesis Example 7: Synthesis of Compound 10

Synthesis Example 8: Synthesis of Compound 13

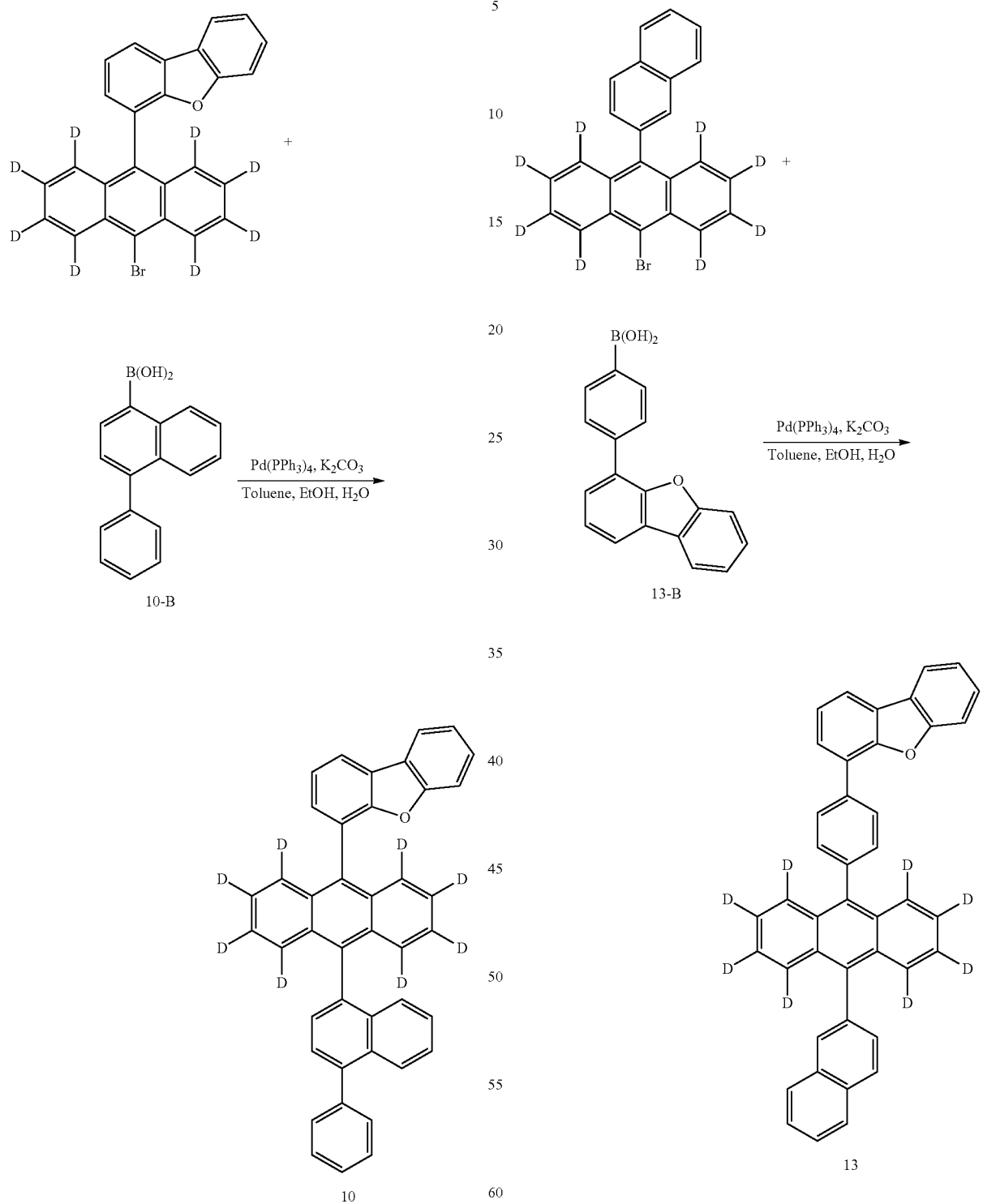

3.5 g (yield 63%) of the present compound 10 was obtained using the same manner as in Synthesis Example 1 except that 2.73 g (11 mmol) of a starting material 10-B was used instead of (4-(naphthalen-1-yl)phenyl)boronic acid.

3.32 g (yield 60%) of the present compound 13 was obtained using the same manner as in Synthesis Example 3 except that a starting material 13-B 3.17 g (11 mmol) was used instead of the starting material 1-B.

MS (MALDI-TOF) m/z: 554 [M]$^+$

Synthesis Example 9: Synthesis of Compound 14

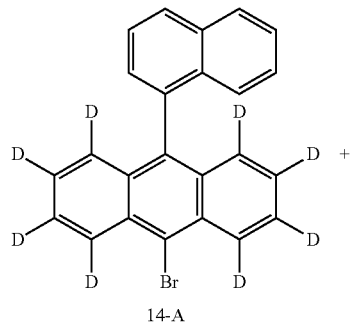

14-A

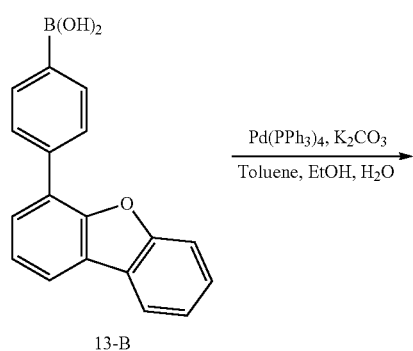

13-B

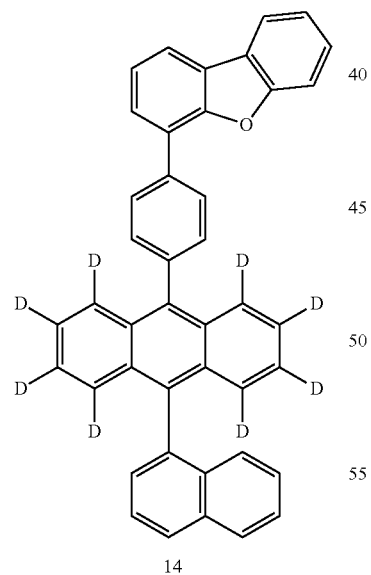

14

3.35 g (yield 64%) of the present compound 14 was obtained using the same manner as in Synthesis Example 3 except that a starting material 14-A 3.92 g (10 mmol) and a starting material 13-B 3.17 g (11 mmol) were used instead of the starting materials 1-A and 1-B.

MS (MALDI-TOF) m/z: 554 [M]$^+$

Synthesis Example 10: Synthesis of Compound 17

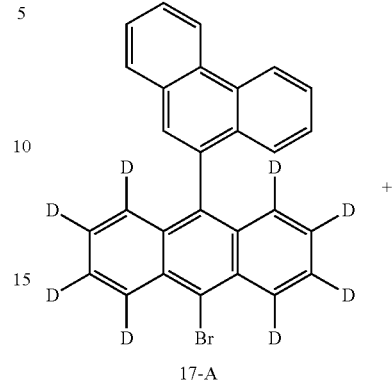

17-A

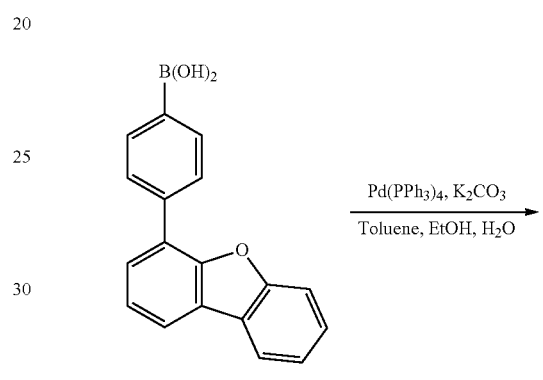

13-B

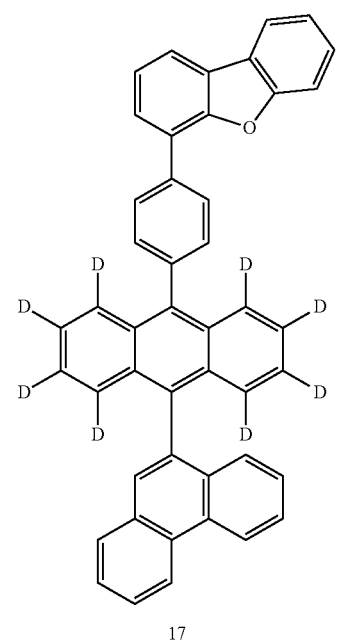

17

3.74 g (yield 62%) of the present compound 17 was obtained using the same manner as in Synthesis Example 3 except that a starting material 17-A 4.401 g (10 mmol) and a starting material 13-B 3.17 g (11 mmol) were used instead of the starting materials 1-A and 1-B.

MS (MALDI-TOF) m/z: 604 [M]$^+$

Synthesis Example 11: Synthesis of Compound 21

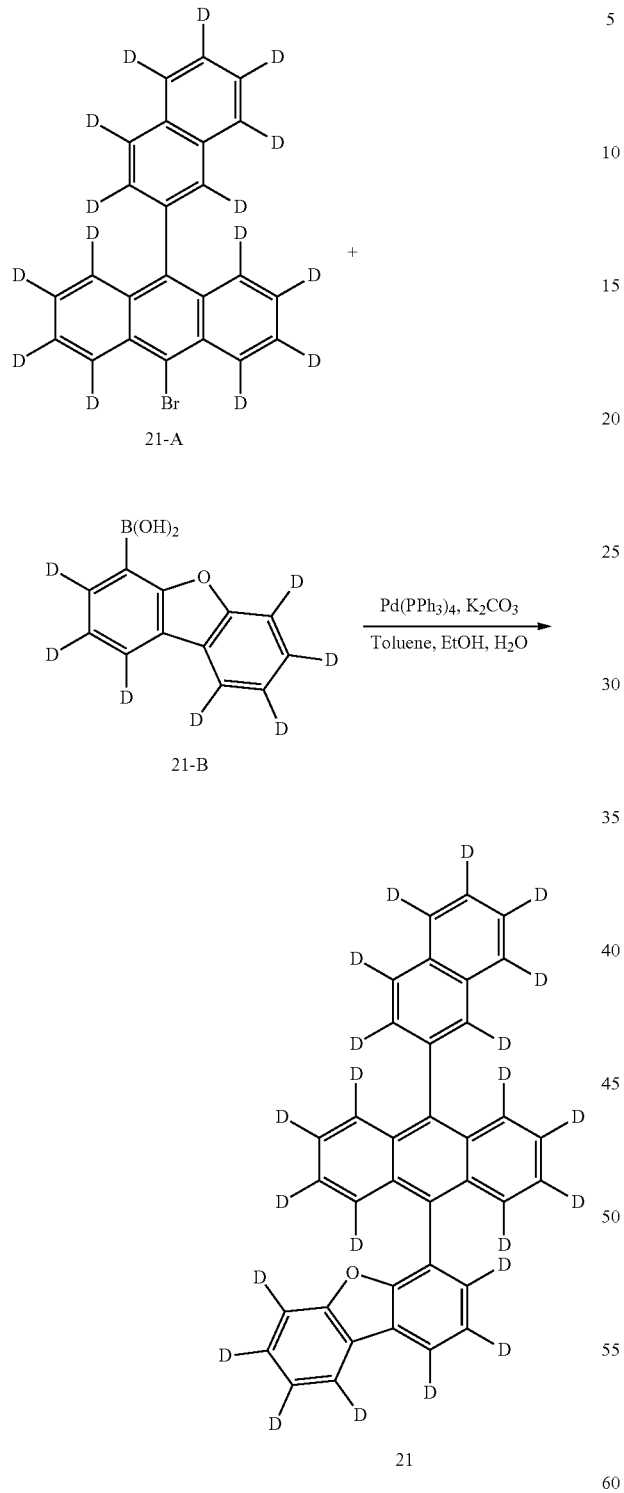

2.86 g (yield 58%) of the present compound 21 was obtained using the same manner as in Synthesis Example 3 except that a starting material 21-A 3.98 g (10 mmol) and a starting material 21-B 2.4 g (11 mmol) were used instead of the starting materials 1-A and 1-B.

MS (MALDI-TOF) m/z: 492 [M]+

Synthesis Example 12: Synthesis of Compound 22

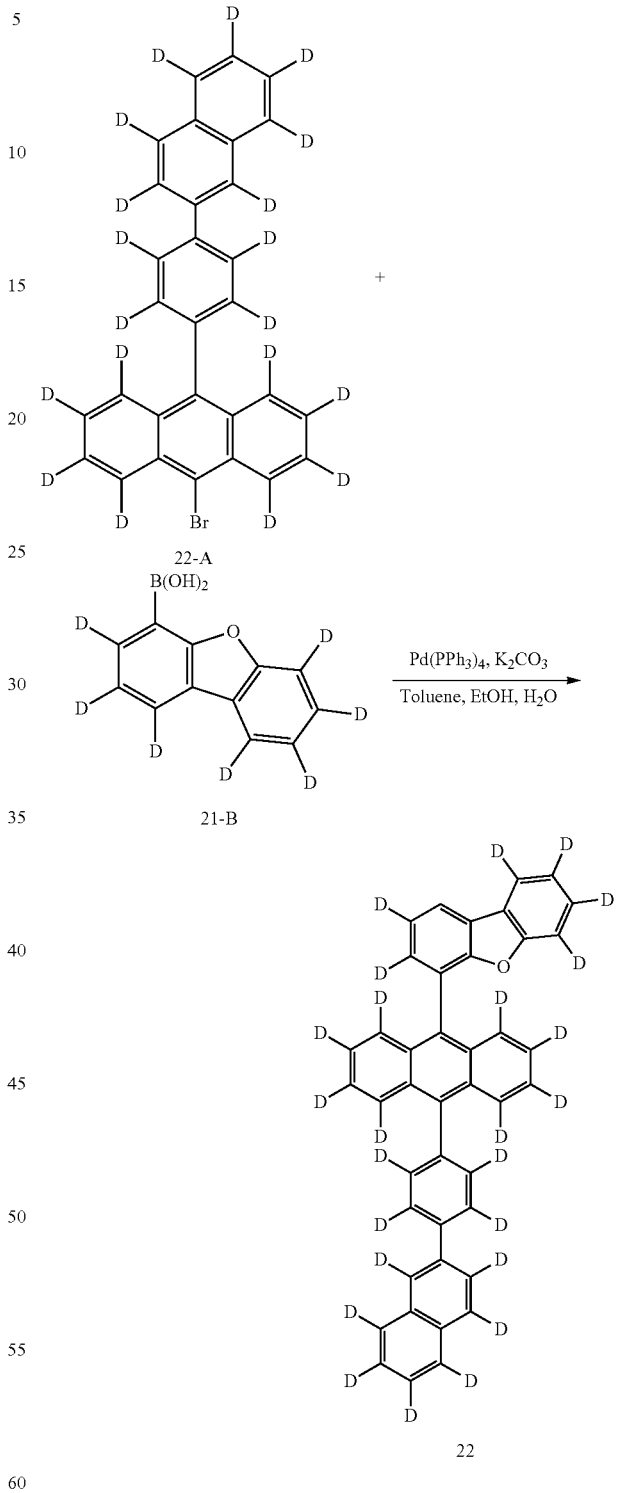

2.98 g (yield 52%) of the present compound 22 was obtained using the same manner as in Synthesis Example 3 except that a starting material 22-A 4.78 g (10 mmol) and a starting material 21-B 2.4 g (11 mmol) were used instead of the starting materials 1-A and 1-B.

MS (MALDI-TOF) m/z: 572 [M]+

Synthesis Example 13: Synthesis of Compound 36

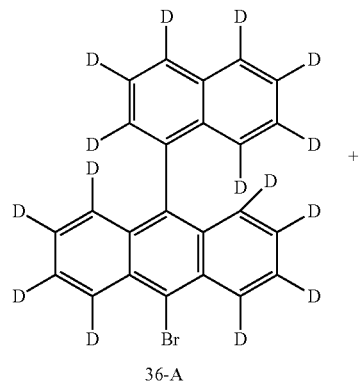

36-A

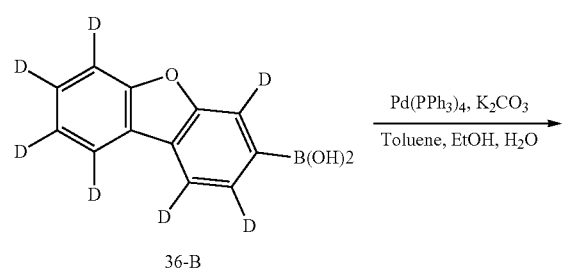

36-B

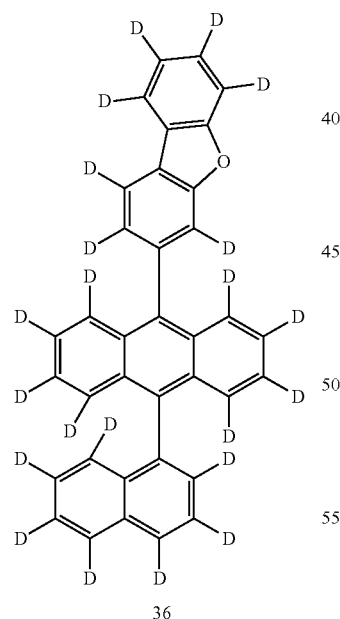

36

2.86 g (yield 58%) of the present compound 36 was obtained using the same manner as in Synthesis Example 3 except that a starting material 36-A 3.98 g (10 mmol) and a starting material 36-B 2.4 g (11 mmol) were used instead of the starting materials 1-A and 1-B.

MS (MALDI-TOF) m/z: 492 [M]$^+$

Synthesis Example 14: Synthesis of Compound 39

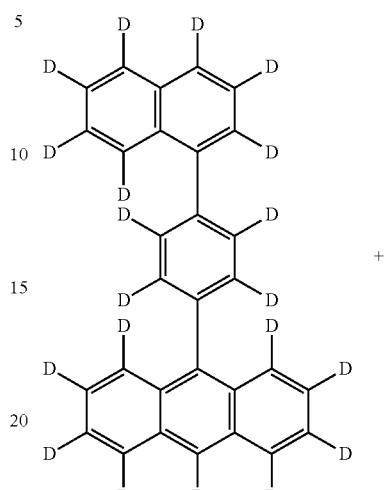

39-A

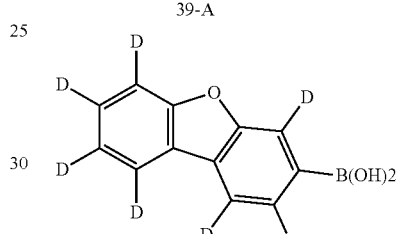

39-B

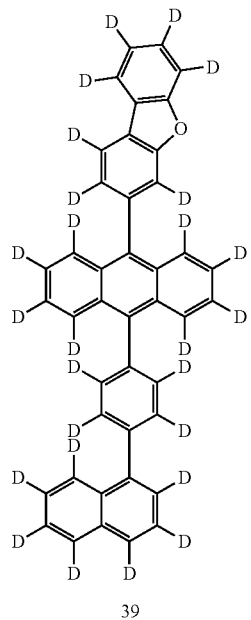

39

2.98 g (yield 52%) of the present compound 39 was obtained using the same manner as in Synthesis Example 3 except that a starting material 39-A 4.78 g (10 mmol) and a starting material 39-B 2.4 g (11 mmol) were used instead of the starting materials 1-A and 1-B.

MS (MALDI-TOF) m/z: 572 [M]$^+$

Synthesis Example 15: Synthesis of Compound 44

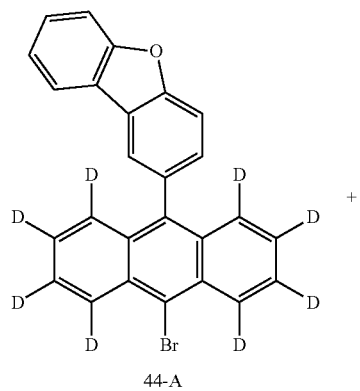

44-A

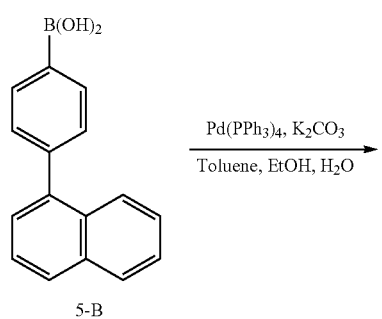

5-B

Pd(PPh₃)₄, K₂CO₃
Toluene, EtOH, H₂O

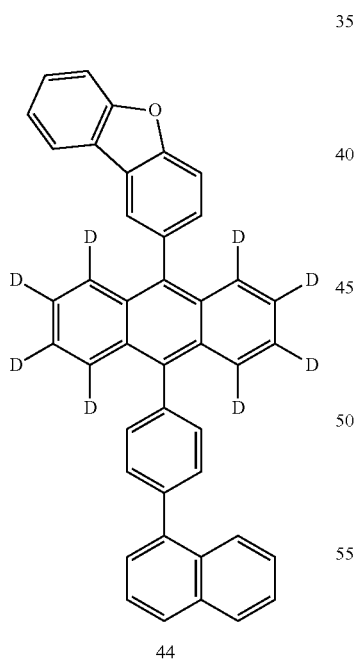

44

3.66 g (yield 66%) of the present compound 44 was obtained using the same manner as in Synthesis Example 3 except that a starting material 44-A 4.30 g (10 mmol) and a starting material 5-B 2.73 g (11 mmol) were used instead of the starting materials 1-A and 1-B.

MS (MALDI-TOF) m/z: 554 [M]⁺

Synthesis Example 16: Synthesis of Compound 72

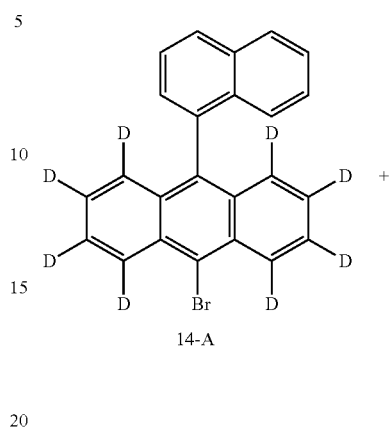

14-A

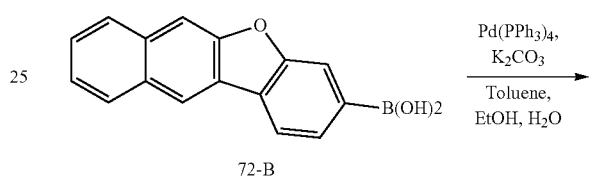

72-B

Pd(PPh₃)₄, K₂CO₃
Toluene, EtOH, H₂O

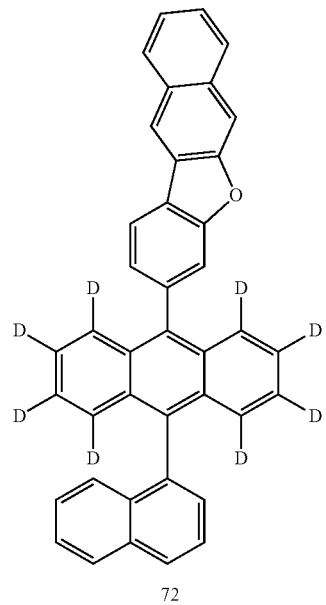

72

3.06 g (yield 58%) of the present compound 72 was obtained using the same manner as in Synthesis Example 3 except that a starting material 14-A 3.91 g (10 mmol) and a starting material 72-B 2.88 g (11 mmol) were used instead of the starting materials 1-A and 1-B.

MS (MALDI-TOF) m/z: 528 [M]⁺

Synthesis Example 17: Synthesis of Compound 73

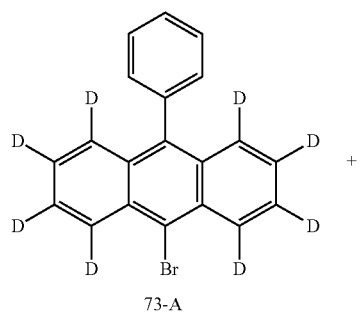

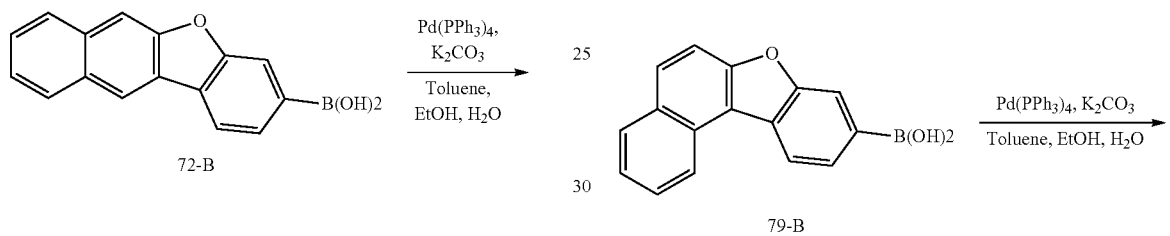

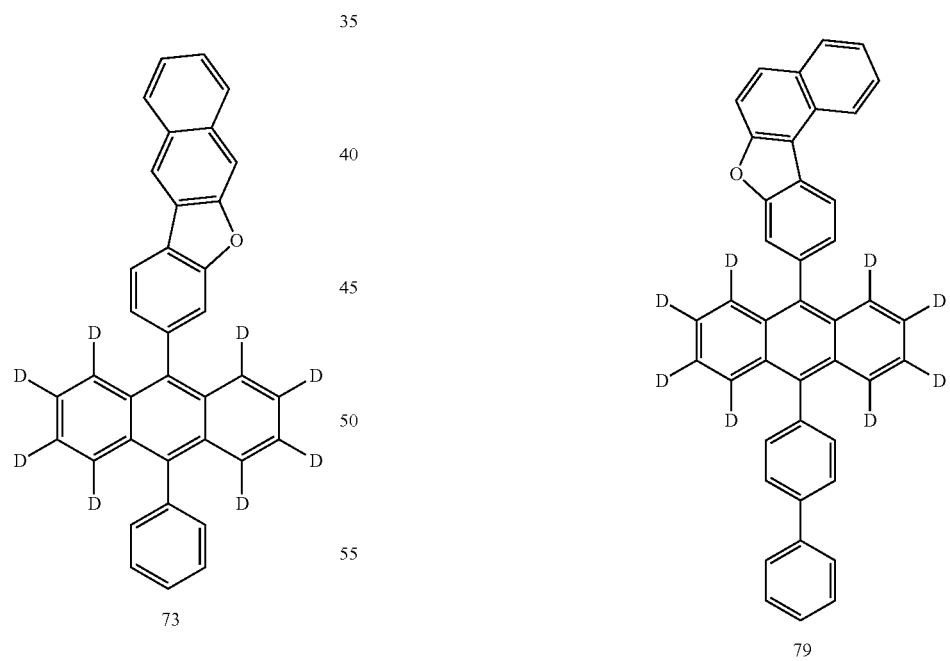

2.77 g (yield 58%) of the present compound 73 was obtained using the same manner as in Synthesis Example 3 except that a starting material 73-A 3.41 g (10 mmol) and a starting material 72-B 2.88 g (11 mmol) were used instead of the starting materials 1-A and 1-B.

MS (MALDI-TOF) m/z: 478 [M]$^+$

Synthesis Example 18: Synthesis of Compound 79

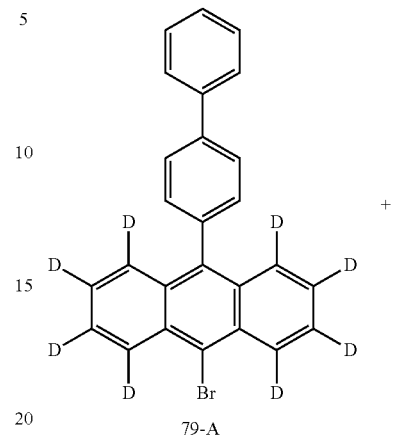

3.66 g (yield 66%) of the present compound 79 was obtained using the same manner as in Synthesis Example 3 except that a starting material 79-A 4.16 g (10 mmol) and a starting material 79-B 2.88 g (11 mmol) were used instead of the starting materials 1-A and 1-B.

MS (MALDI-TOF) m/z: 554 [M]$^+$

Synthesis Example 19: Synthesis of Compound 108

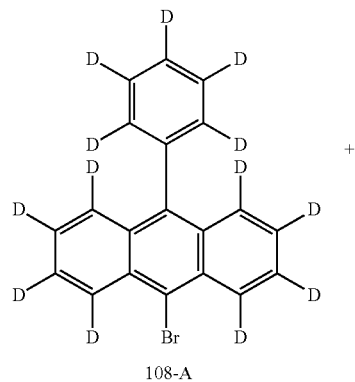

108-A

+

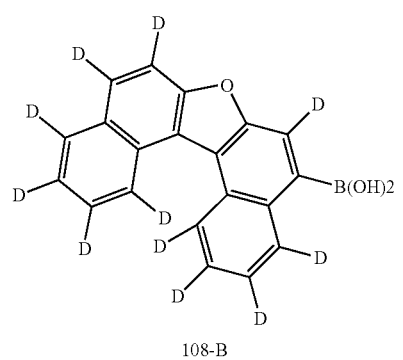

108-B

Pd(PPh₃)₄, K₂CO₃
Toluene, EtOH, H₂O
→

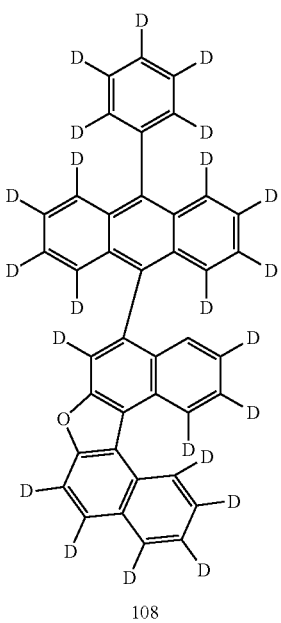

108

2.83 g (yield 52%) of the present compound 108 was obtained using the same manner as in Synthesis Example 3 except that a starting material 108-A 3.45 g (10 mmol) and a starting material 108-B 3.55 g (11 mmol) were used instead of the starting materials 1-A and 1-B.

MS (MALDI-TOF) m/z: 57 [M]⁺

Synthesis Example 20: Synthesis of Compound 111

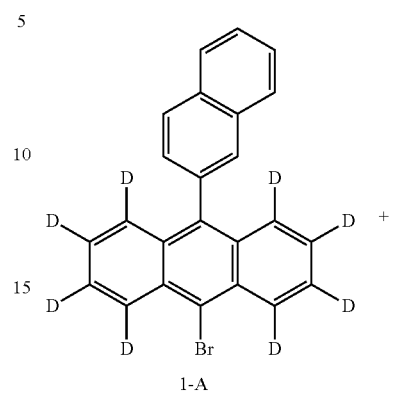

1-A

+

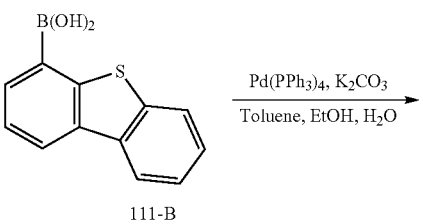

111-B

Pd(PPh₃)₄, K₂CO₃
Toluene, EtOH, H₂O
→

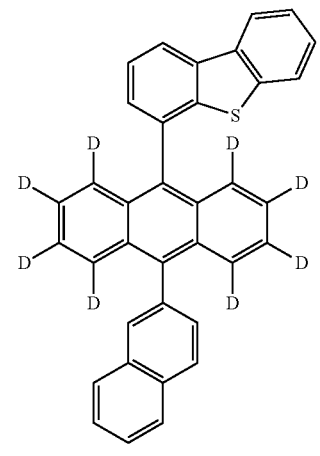

111

3.26 g (yield 66%) of the present compound 111 was obtained using the same manner as in Synthesis Example 3 except that a starting material 1-A 3.90 g (10 mmol) and a starting material 111-B 2.51 g (11 mmol) were used instead of the starting materials 1-A and 1-B.

MS (MALDI-TOF) m/z: 494 [M]⁺

Synthesis Example 21: Synthesis of Compound 113

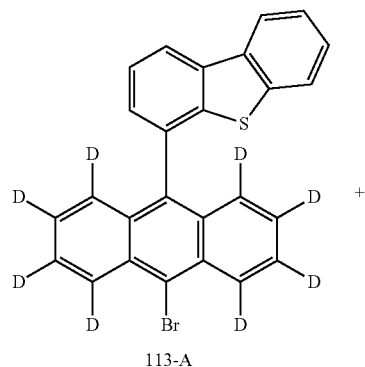

113-A

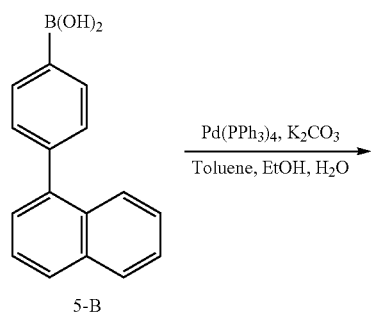

5-B

Pd(PPh$_3$)$_4$, K$_2$CO$_3$
Toluene, EtOH, H$_2$O

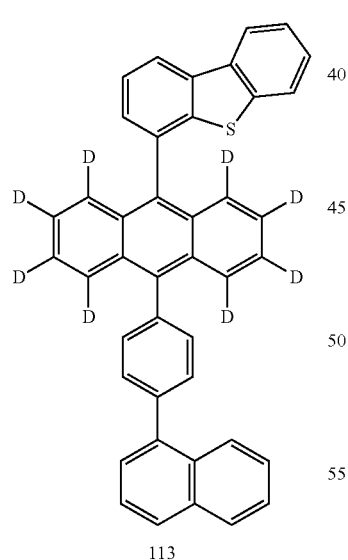

113

3.76 g (yield 66%) of the present compound 113 was obtained using the same manner as in Synthesis Example 3 except that a starting material 113-A 4.46 g (10 mmol) and a starting material 5-B 2.73 g (11 mmol) were used instead of the starting materials 1-A and 1-B.

MS (MALDI-TOF) m/z: 570 [M]$^+$

Synthesis Example 22: Synthesis of Compound 114

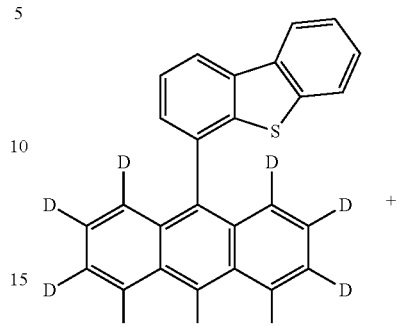

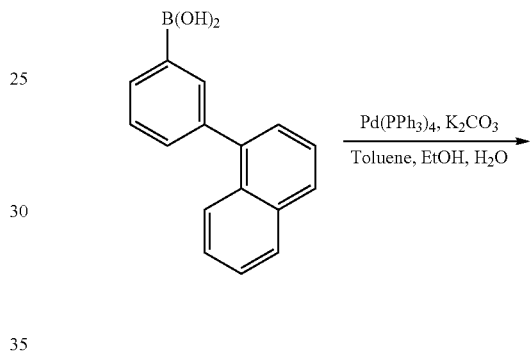

Pd(PPh$_3$)$_4$, K$_2$CO$_3$
Toluene, EtOH, H$_2$O

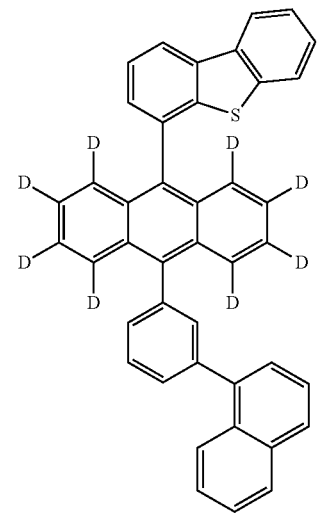

114

3.53 g (62% yield) of the present compound 114 was obtained in the same manner as in Synthesis Example 2 except that 4.46 g (10 mmol) of a starting material 113-A was used instead of 4-(10-bromoanthracene-9-yl)dibenzofuran-d8.

MS (MALDI-TOF) m/z: 570 [M]$^+$

Synthesis Example 23: Synthesis of Compound 199

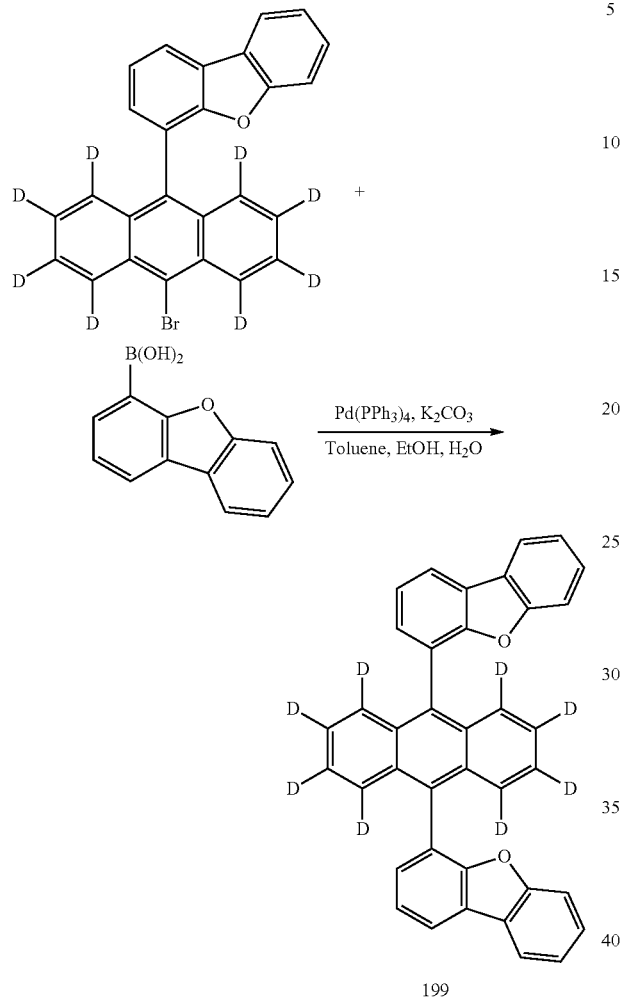

2.64 g (51% yield) of the present compound 199 was obtained using the same manner as in Synthesis Example 1 except that 2.33 g (11 mmol) of a starting material 1-B was used instead of (4-(naphthalen-1-yl) phenyl)boron acid.

Synthesis Example 24: Synthesis of Compound 224

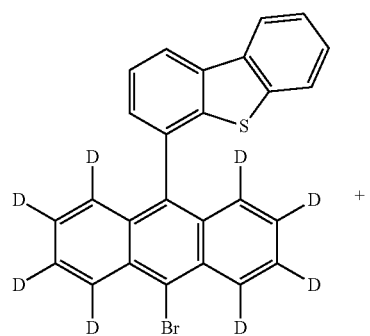

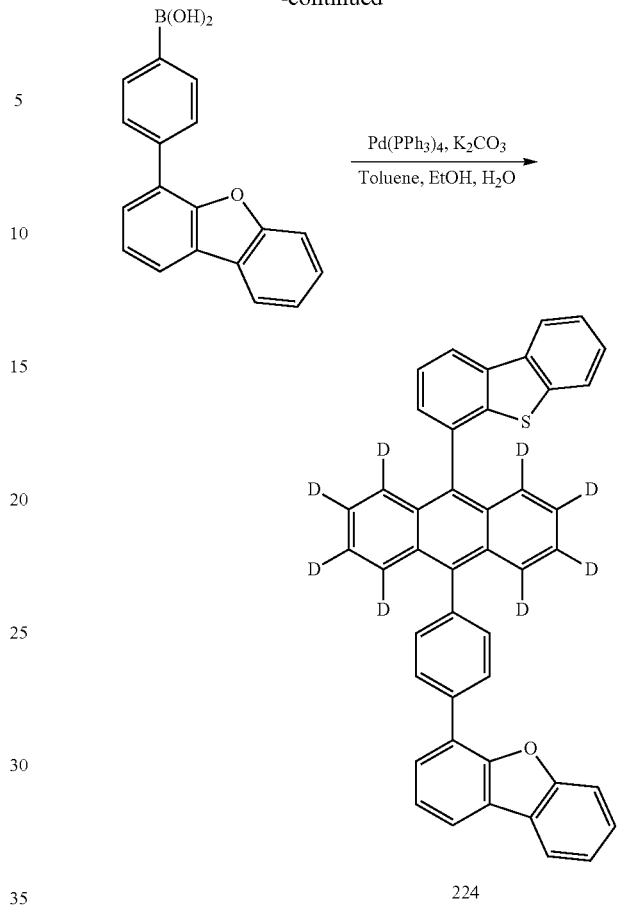

3.76 g (yield 66%) of the present compound 224 was obtained using the same manner as in Synthesis Example 3 except that a starting material 113-A 4.46 g (10 mmol) and a starting material 13-B 3.17 g (11 mmol) were used instead of the starting materials 1-A and 1-B.

MS (MALDI-TOF) m/z: 570 [M]$^+$

Present Example 1: Manufacturing of Organic Electroluminescent Device

An Ag alloy layer as a light-reflecting layer, and an ITO (10 nm) layer as an anode of an organic electroluminescent device were sequentially deposited on a substrate. Then, patterning was performed using a photo-lithograph process to divide the substrate region into cathode and anode regions and an insulating layer region. A UV ozone treatment and a surface-treatment using $O_2$:$N_2$ plasma were executed to enhance a work-function of the anode and to execute a descum process. Then, 1, 4, 5, 8, 9, 11-hexaazatriphenylene-hexacarbonitrile (HAT-CN) as a hole-injecting layer (HIL) at 100-Å thickness was deposited on the ITO layer.

Then, N4, N4, N4', N4'-tetra([1,1'-biphenyl]-4-yl)-[1,1'-biphenyl]-4,4'-diamine was vacuum deposited on the hole-injecting layer (HIL), to form a 1000-Å thick hole-transporting layer (HTL).

Then, on top of the hole-transporting layer (HTL), N-phenyl-N-(4-(spiro [benzo[de]anthracene-7,9-fluorene]-2-yl) phenyl)dibenzo[b,d]furan-4-amine as an electron-blocking layer (EBL) was deposited in a thickness of 150 angstroms. Then, on top of the electron-blocking layer (EBL), the present compound 6 as a host material of a light-emitting layer (EML) was deposited. At the same time, N1, N1, N6, N6-tetrakis(4-(1-silyl)phenyl)pyrene-1,6-diamine as dopants was doped into the host material, to from the light emitting layer (EML).

Then, a mixture of 2-(4-(9,10-di(naphthalene-2-yl)anthracene-2-yl)phenyl)-1-phenyl-1H-benzo[d]imidazole and LiQ in a weight ratio of 1:1 was deposited to a thickness of 360 Å as an electron-transporting layer (ETL) on the EML layer. Then, a mixture of magnesium (Mg) and silver (Ag) at a ratio of 9:1 was deposited as a cathode at a thickness of 160 Å on the ETL layer.

Next, N4, N4'-diphenyl-N4, N4'-bis(4-(9-phenyl-9H-carbazol-3-yl)phenyl-[1, 1'-biphenyl]-4, 4'-diamine was deposited as a capping layer (CPL) to a thickness of 63 to 65 nm on the cathode layer.

Then, we attached a seal cap to the capping layer (CPL) with a UV curing adhesive to protect the organic electroluminescent device from atmospheric $O_2$ or moisture. In this way, the organic electroluminescent device was fabricated.

Present Example 2 to 11: Manufacturing of Organic Electroluminescent Device

Organic electroluminescent devices were fabricated in the same manner as in Present Example 1 except that the present compounds 1, 3, 5, 9, 10, 13, 14, 17, 21 and 22 of a following Table 1 were used as the host material instead of the compound 6.

Present Example 12: Manufacturing of Organic Electroluminescent Device

An Ag alloy layer as a light-reflecting layer, and an ITO (10 nm) layer as an anode of an organic electroluminescent device were sequentially deposited on a substrate. Then, patterning was performed using a photo-lithograph process to divide the substrate region into cathode and anode regions and an insulating layer region. A UV ozone treatment and a surface-treatment using $O_2:N_2$ plasma were executed to enhance a work-function of the anode and to execute a descum process. Then, 1, 4, 5, 8, 9, 11-hexaazatriphenylene-hexacarbonitrile (HAT-CN) as a hole-injecting layer (HIL) at 100-Å thickness was deposited on the ITO layer.

Then, N4, N4, N4', N4'-tetra([1,1'-biphenyl]-4-yl)-[1,1'-biphenyl]-4,4'-diamine was vacuum deposited on the hole-injecting layer (HIL), to form a 1000-Å thick hole-transporting layer (HTL).

Then, on top of the hole-transporting layer (HTL), N-phenyl-N-(4-(spiro [benzo[de]anthracene-7,9-fluorene]-2-yl) phenyl)dibenzo[b,d]furan-4-amine as an electron-blocking layer (EBL) was deposited in a thickness of 150 angstroms. Then, on top of the electron-blocking layer (EBL), the present compound 36 as a host material of a light-emitting layer (EML) was deposited. At the same time, a following compound 1-B as dopants was doped into the host material, to from the light emitting layer (EML).

Compound 1-B

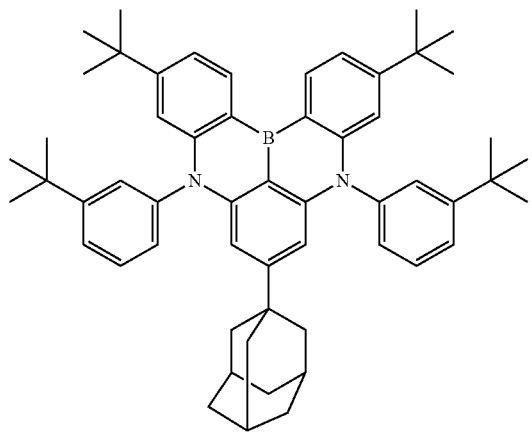 [SMILES: CC(C)(C)c1cccc(N2c3cc(C(C)(C)C)ccc3B3c4ccc(C(C)(C)C)cc4N(c4cccc(C(C)(C)C)c4)c4cc(C56CC7CC(CC(C7)C5)C6)cc2c43)c1]

Then, a mixture of 2-(4-(9,10-di(naphthalene-2-yl)anthracene-2-yl)phenyl)-1-phenyl-1H-benzo[d]imidazole and LiQ in a weight ratio of 1:1 was deposited to a thickness of 360 Å as an electron-transporting layer (ETL) on the EML layer. Then, a mixture of magnesium (Mg) and silver (Ag) at a ratio of 9:1 was deposited as a cathode at a thickness of 160 Å on the ETL layer.

Next, N4, N4'-diphenyl-N4, N4'-bis(4-(9-phenyl-9H-carbazol-3-yl)phenyl-[1,1'-biphenyl]-4, 4'-diamine was deposited as a capping layer (CPL) to a thickness of 63 to 65 nm on the cathode layer.

Then, we attached a seal cap to the capping layer (CPL) with a UV curing adhesive to protect the organic electroluminescent device from atmospheric $O_2$ or moisture. In this way, the organic electroluminescent device was fabricated.

Present Example 13 to 22: Organic Electroluminescent Device

Organic electroluminescent devices were fabricated using the same method as in the Present Example 12 except that the present compounds 39, 44, 79, 72, 73, 108, 111, 113, 199, 224 of the following Table 1 were used as the host material instead of the compound 36.

Comparative Examples 1 to 7: Manufacturing of Organic Electroluminescent Device

Comparative organic electroluminescent devices were fabricated using the same method as in the Present Example 1 except that following Comparative Compounds A to J were employed as the host material instead of the compound 6.

Comparative Compound A
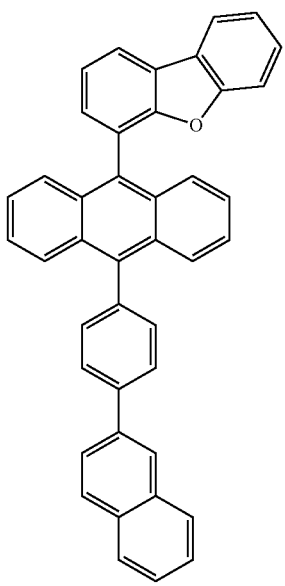
Comparative Compound B
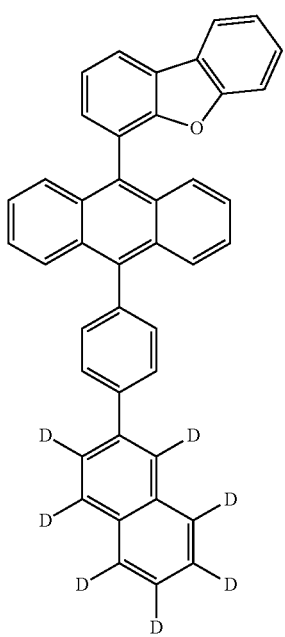
Comparative Compound C
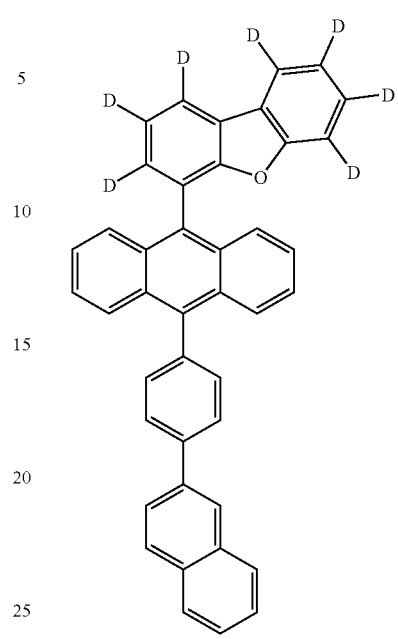
Comparative Compound D
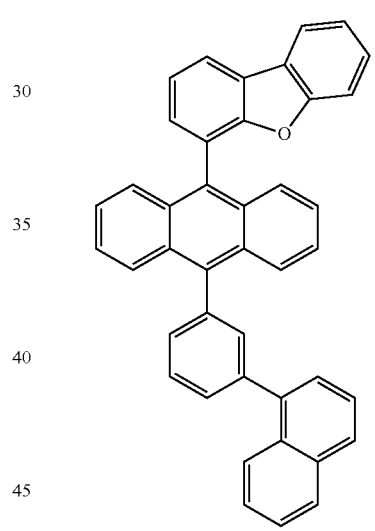
Comparative Compound E
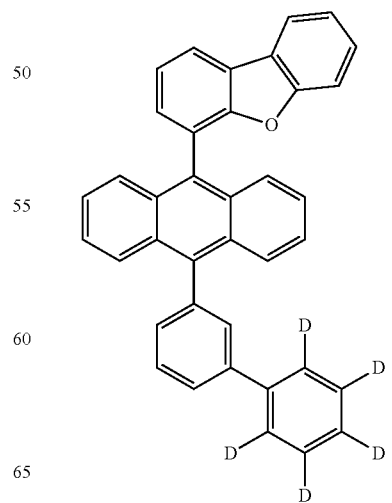

Comparative Compound F

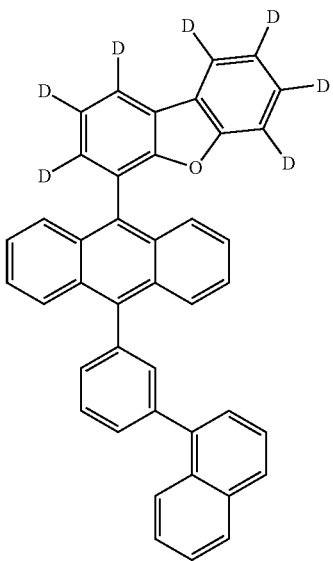

Comparative Compound G

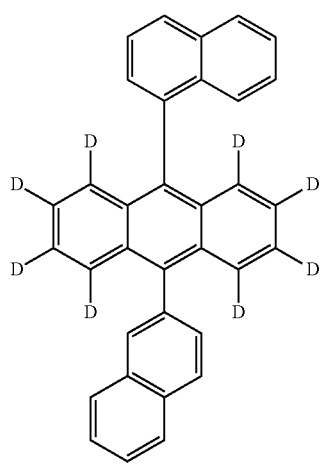

Comparative Compound H

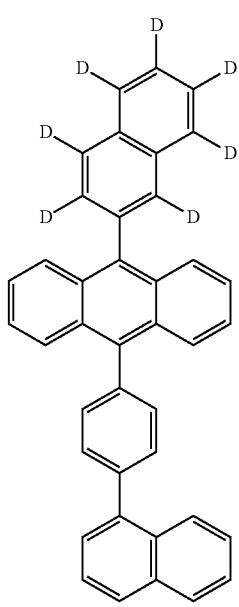

Comparative Compound I

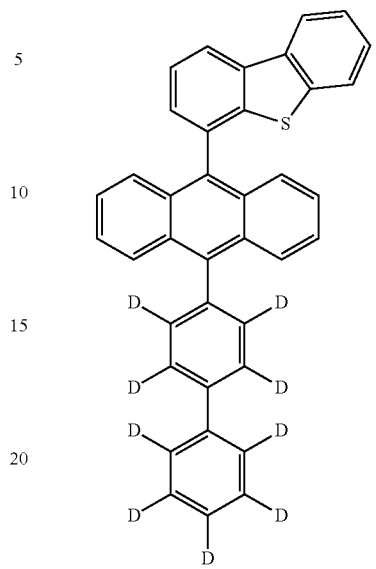

Comparative Compound J

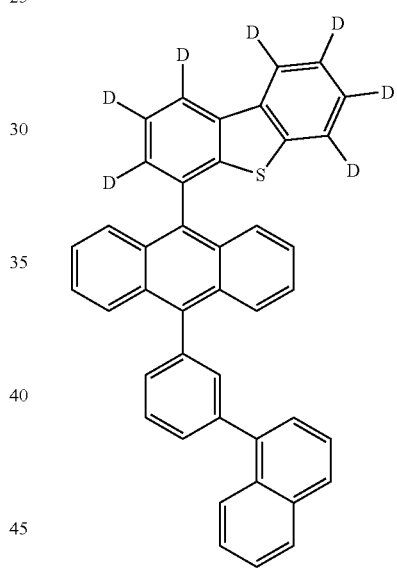

Experimental Example 1: Property Analysis of Organic Electroluminescent Device

For the organic electroluminescent devices as prepared according to Present Examples 1 to 22 and Comparative Examples 1 to 9, driving voltages and luminous efficiencies characteristics in driving the devices at 10 mA/cm² current and lifespan characteristics at acceleration of the devices at 20 mA/cm² were analyzed. Results are shown in the following Table 1.

"T95 lifespan" in Table 1 below refers to a time duration which it takes for a display device to lose 5% of its initial brightness. The T95 lifespan is a customer requirement that is the most difficult to meet. Thus, the T95 lifespan determines whether a image burn in occurs in the display device.

TABLE 1

| Examples | Host | Voltage (v) | Current efficiency (Cd/A) | Power efficiency (lm/w) | External quantum efficiency EQE(%) | Color coordinate CIEx | Color coordinate CIEy | Lifespan T95 (hrs) |
|---|---|---|---|---|---|---|---|---|
| Comparative Example 1 | Comparative Compound A | 3.78 | 5.3 | 4.7 | 11.4 | 0.142 | 0.048 | 92 |
| Comparative Example 2 | Comparative Compound B | 3.81 | 5.7 | 4.7 | 11.3 | 0.141 | 0.050 | 100 |
| Comparative Example 3 | Comparative Compound C | 3.82 | 5.8 | 4.8 | 11.6 | 0.141 | 0.049 | 105 |
| Comparative Example 7 | Comparative Compound G | 4.2 | 5.6 | 4.2 | 10.9 | 0.139 | 0.052 | 120 |
| Comparative Example 8 | Comparative Compound H | 4.15 | 5.4 | 4.1 | 10 | 0.138 | 0.054 | 100 |
| Comparative Example 9 | Comparative Compound I | 3.79 | 5.1 | 4.2 | 9.9 | 0.139 | 0.051 | 75 |
| Present Example 1 | Compound 6 | 3.88 | 6.0 | 4.9 | 11.3 | 0.139 | 0.052 | 130 |
| Present Example 2 | Compound 1 | 3.93 | 4.8 | 3.9 | 9.1 | 0.140 | 0.052 | 112 |
| Present Example 3 | Compound 3 | 3.97 | 5.4 | 4.3 | 10.4 | 0.140 | 0.052 | 110 |
| Present Example 4 | Compound 5 | 4.09 | 5.2 | 4.0 | 10.2 | 0.141 | 0.05 | 125 |
| Present Example 5 | Compound 9 | 3.87 | 4.7 | 3.8 | 8.8 | 0.139 | 0.053 | 120 |
| Present Example 6 | Compound 10 | 3.81 | 5.1 | 4.2 | 10.0 | 0.140 | 0.049 | 130 |
| Present Example 7 | Compound 13 | 3.91 | 5.0 | 4.0 | 9.4 | 0.140 | 0.051 | 130 |
| Present Example 8 | Compound 14 | 4.0 | 4.8 | 3.8 | 9.3 | 0.141 | 0.048 | 135 |
| Present Example 9 | Compound 17 | 4.1 | 5.2 | 4.2 | 10 | 0.139 | 0.052 | 110 |
| Present Example 10 | Compound 21 | 3.95 | 4.8 | 3.8 | 9.1 | 0.140 | 0.052 | 120 |
| Present Example 11 | Compound 22 | 4.05 | 4.0 | 5.2 | 10.2 | 0.141 | 0.050 | 122 |
| Present Example 12 (Boron D) | Compound 36 | 3.94 | 5.1 | 4.1 | 9.9 | 0.14 | 0.05 | 120 |
| Present Example 13 (Boron D) | Compound 39 | 3.94 | 4.9 | 3.9 | 10.5 | 0.144 | 0.044 | 120 |
| Present Example 14 (Boron D) | Compound 44 | 3.94 | 4.9 | 3.9 | 10.5 | 0.144 | 0.044 | 120 |
| Present Example 15 (Boron D) | Compound 79 | 3.68 | 5.2 | 4.4 | 9.7 | 0.138 | 0.053 | 115 |
| Present Example 16 (Boron D) | Compound 72 | 3.83 | 5.6 | 4.6 | 10.0 | 0.14 | 0.051 | 110 |
| Present Example 17 (Boron D) | Compound 73 | 3.79 | 5.1 | 4.2 | 10.2 | 0.141 | 0.05 | 110 |
| Present Example 18 (Boron D) | Compound 108 | 3.66 | 4.8 | 4.1 | 9.2 | 0.140 | 0.051 | 113 |
| Present Example 19 (Boron D) | Compound 111 | 3.98 | 5.1 | 4.1 | 9.8 | 0.140 | 0.050 | 119 |
| Present Example 20 (Boron D) | Compound 113 | 3.95 | 5.2 | 4.1 | 8.8 | 0.139 | 0.051 | 120 |
| Present Example 21 (Boron D) | Compound 199 | 3.69 | 5.1 | 4.3 | 9.2 | 0.138 | 0.052 | 120 |
| Present Example 22 (Boron D) | Compound 224 | 3.75 | 5.1 | 4.1 | 10 | 0.140 | 0.050 | 125 |

As Table 1 shows, Present Example 1 which employs the compound according to the present disclosure as a host material exhibited excellent current efficiency and lifespan increase up to about 47% compared to Comparative Examples 1 to 3 which has a similar compound structure thereto. Further, Present Examples 1 to 22 in accordance with the present disclosure in which polar molecules are bonded to anthracene were found to have lower drive voltage than Comparative Examples 7 to 8 in which polar molecules were not bonded thereto.

From those findings, it may be concluded that the anthracene compound in accordance with the present disclosure achieves lower drive voltage than that achieved by a host material with no polarity, and the deuteration leads to the longer lifespan.

Thus, it may be confirmed that the compounds represented by the Chemical Formula 1 of the present disclosure contain polar molecules such as dibenzo furan or dibenzo thiophene, and the anthracene deuteration leads to excellent properties such as the low drive voltage implementation and long lifespan.

Present Examples 23 to 24: Manufacturing of Organic Electroluminescent Device

Organic electroluminescent devices were fabricated in the same manner as in Present Example 1, except that the compounds 7 or 114 of a following Table 2 were used as the host material instead of the compound 6.

Experimental Example 2: Property Analysis of Organic Electroluminescent Device

For the organic electroluminescent devices as prepared according to Present Examples 23 to 24 and Comparative Examples 4 to 8 and 10, driving voltages and luminous efficiencies characteristics in driving the devices at 10 $mA/cm^2$ current and lifespan characteristics at acceleration of the devices at 20 $mA/cm^2$ were analyzed. Results are shown in the following Table 2.

"T95 lifespan" in Table 2 below refers to a time duration which it takes for a display device to lose 5% of its initial brightness. The T95 lifespan is a customer requirement that is the most difficult to meet. Thus, the T95 lifespan determines whether a image burn in occurs in the display device.

As Table 2 shows, Present Example 23 which employs the compound according to the present disclosure as a host material exhibited excellent current efficiency and lifespan increase up to about 78% compared to Comparative Examples 4 to 6 which has a similar compound structure thereto.

As Table 2 shows, Present Example 24 which employs the compound according to the present disclosure as a host material exhibited excellent current efficiency and lifespan increase up to about 23% compared to Comparative Example 10 which has a similar compound structure thereto.

Further, Present Examples 23 and 24 in accordance with the present disclosure in which polar molecules are bonded to anthracene were found to have lower drive voltage than Comparative Examples 7 to 8 in which polar molecules were not bonded thereto.

Thus, it may be confirmed that the compounds represented by the Chemical Formula 1 of the present disclosure contain polar molecules such as dibenzo furan or dibenzo thiophene, and the anthracene deuteration leads to excellent properties such as the low drive voltage implementation and long lifespan.

The description of the disclosed embodiments is provided to enable any person skilled in the art to make or use the present disclosure. Various modifications to these embodiments will be readily apparent to those skilled in the art of the present disclosure. The generic principles defined herein may be applied to other embodiments without departing from the scope of the present disclosure. Thus, the present disclosure is not to be construed as limited to the embodiments set forth herein, but is to be accorded the widest scope consistent with the principles and novel features set forth herein.

The various embodiments described above can be combined to provide further embodiments. All of the U.S. patents, U.S. patent application publications, U.S. patent applications, foreign patents, foreign patent applications and

TABLE 2

| Examples | Host | Voltage (v) | Current efficiency (Cd/A) | Power efficiency (lm/w) | External quantum efficiency EQE(%) | Color coordinate CIEx | Color coordinate CIEy | Lifespan T95 (hrs) |
|---|---|---|---|---|---|---|---|---|
| Comparative Example 4 | Comparative Compound D | 4.13 | 5.9 | 4.5 | 11.0 | 0.139 | 0.053 | 90 |
| Comparative Example 5 | Comparative Compound E | 4.12 | 6.1 | 4.6 | 11.3 | 0.139 | 0.053 | 125 |
| Comparative Example 6 | Comparative Compound F | 4.10 | 5.6 | 4.3 | 10.9 | 0.141 | 0.050 | 130 |
| Comparative Example 7 | Comparative Compound G | 4.24 | 5.6 | 4.1 | 10.9 | 0.139 | 0.052 | 120 |
| Comparative Example 8 | Comparative Compound H | 4.19 | 5.4 | 4.1 | 10 | 0.138 | 0.054 | 100 |
| Present Example 23 | Compound 7 | 4.12 | 6.1 | 4.6 | 11.3 | 0.139 | 0.053 | 160 |
| Comparative Example 10 | Comparative Compound J | 4.05 | 5.7 | 4.4 | 11.6 | 0.142 | 0.046 | 95 |
| Present Example 24 | Compound 114 | 3.97 | 5.9 | 4.7 | 8.8 | 0.139 | 0.053 | 120 | non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic electroluminescent device, comprising:
   a first electrode;
   a second electrode facing away the first electrode; and
   at least one organic layer interposed between the first electrode and the second electrode, wherein the at least one organic layer contains at least one compound selected from the following structures:

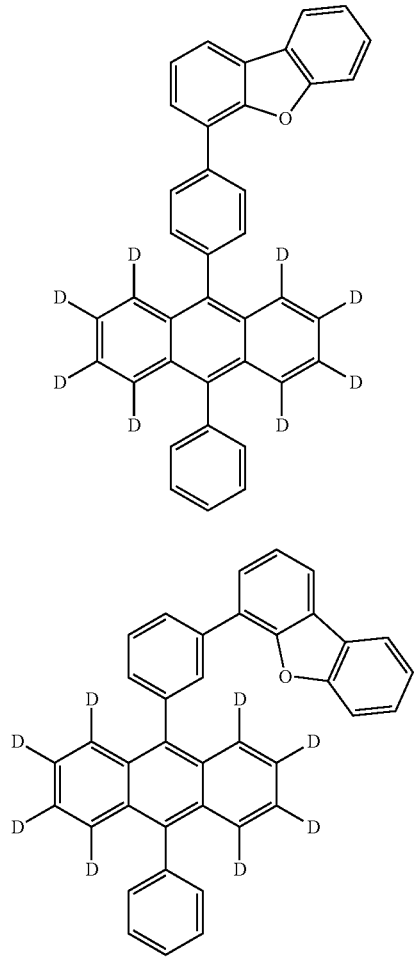

11

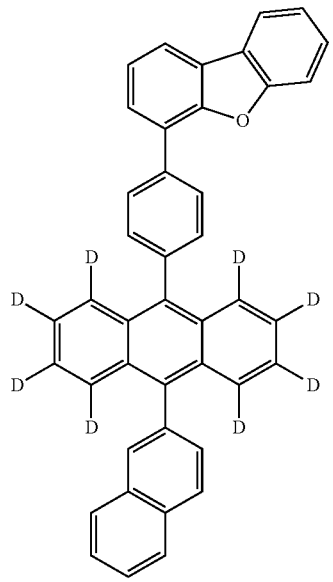

13

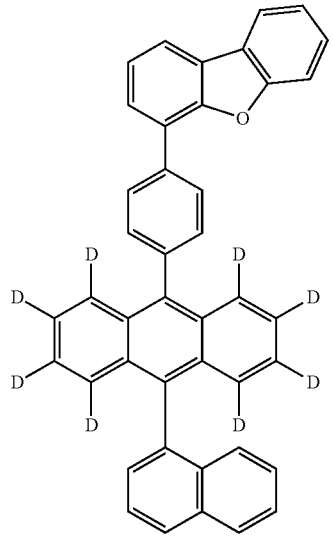

14

15
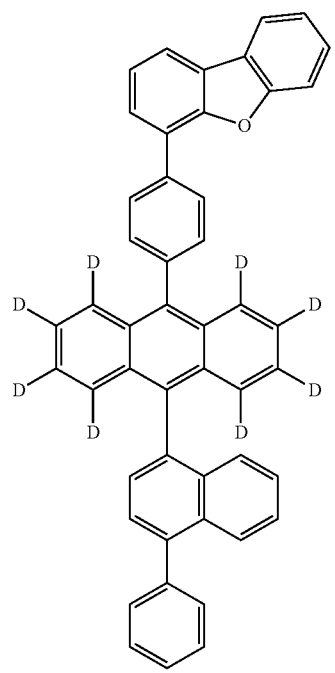
16
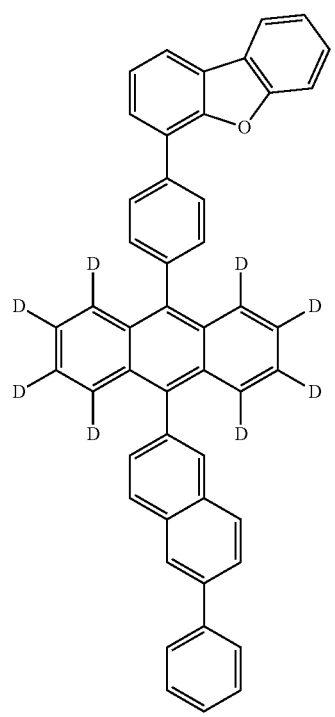
17
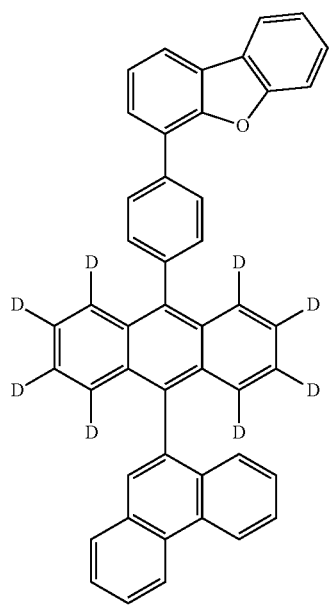
18
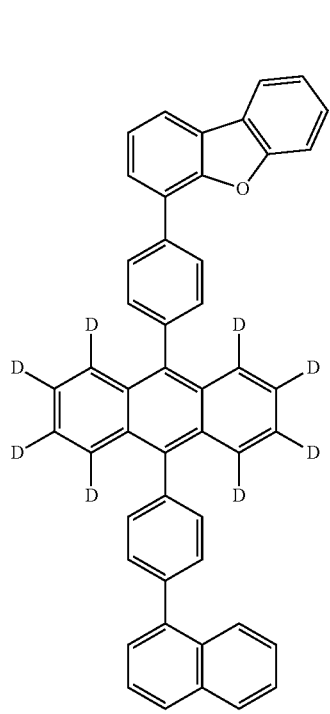

165
-continued
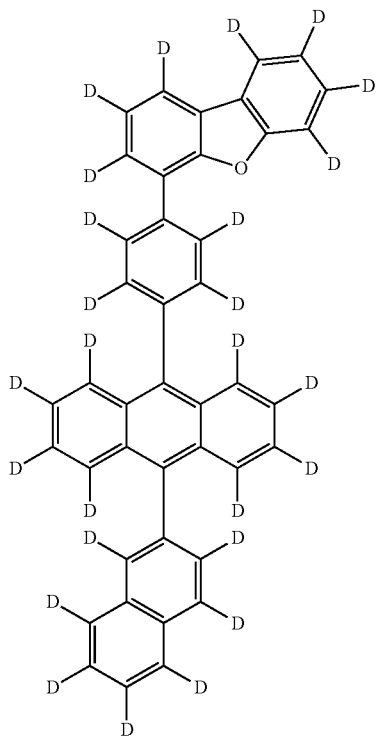
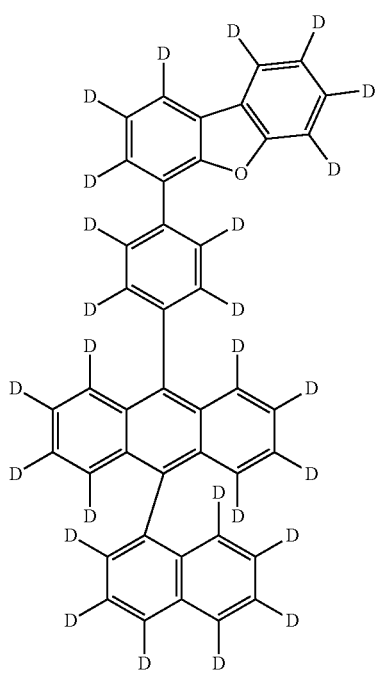
166
-continued
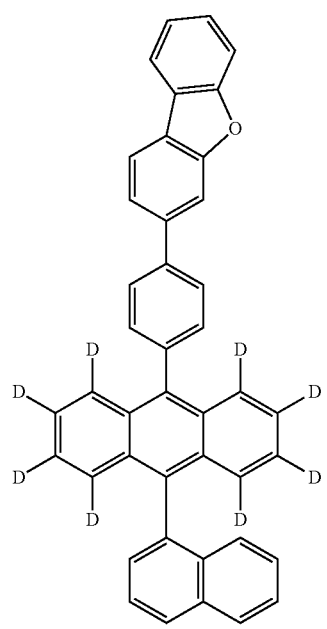
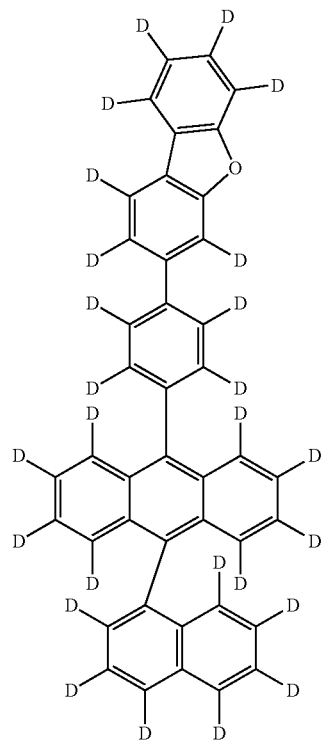

49
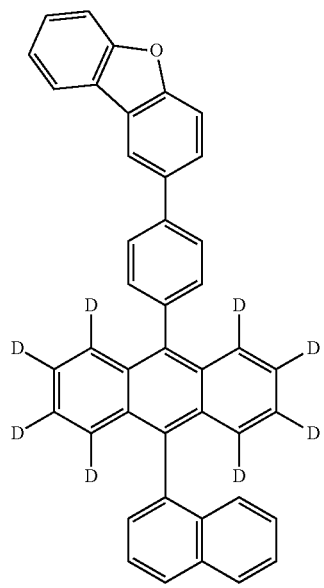
56
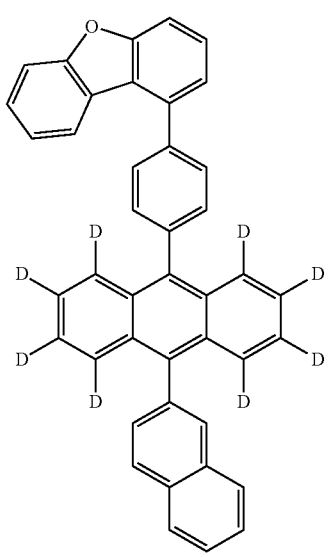
57
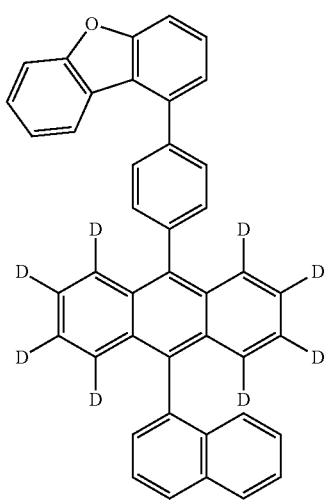
64
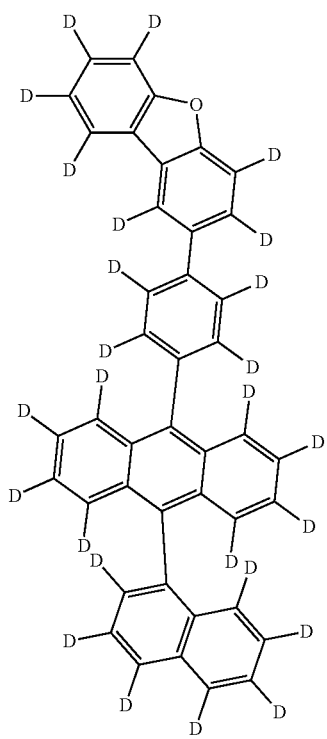
82
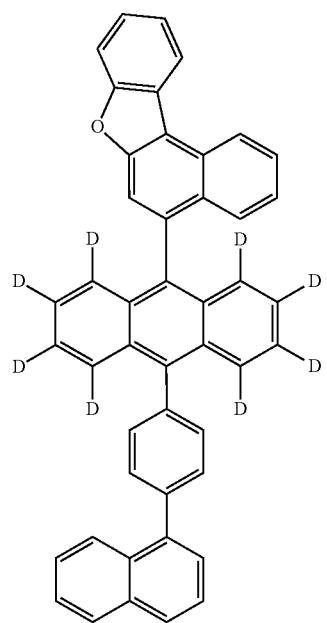

86
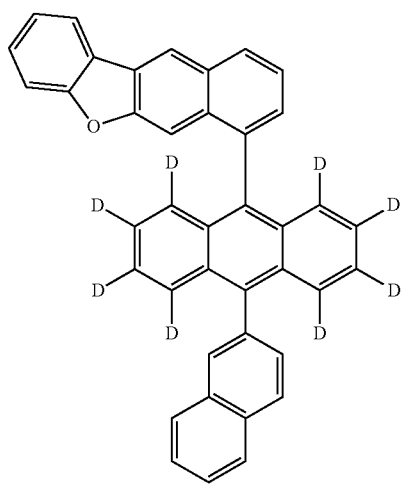
87
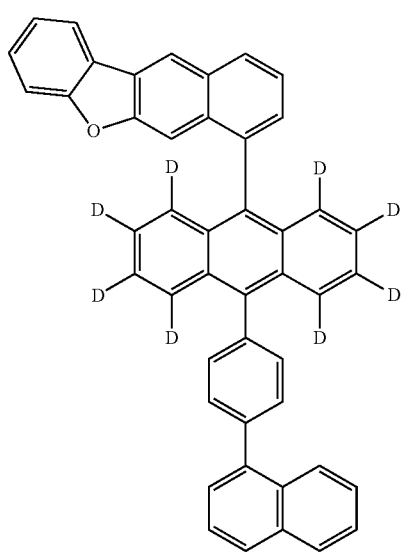
88
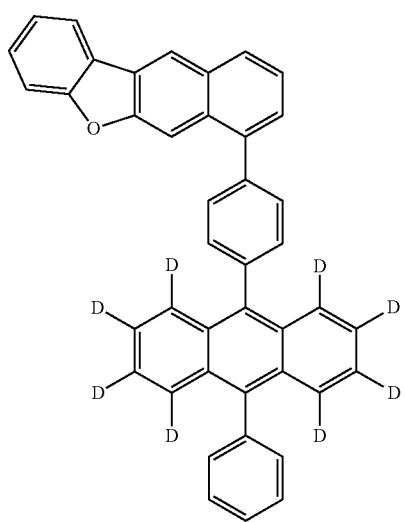
89
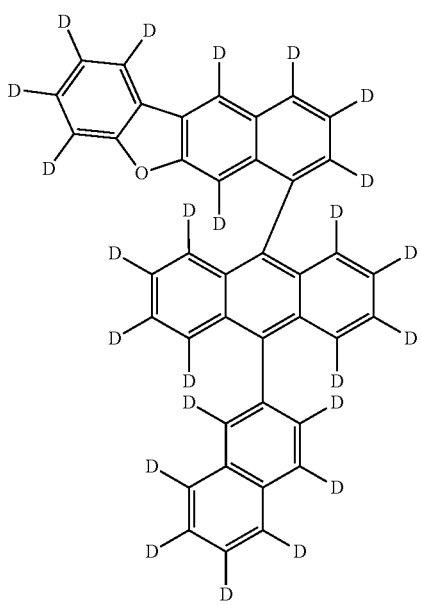
90
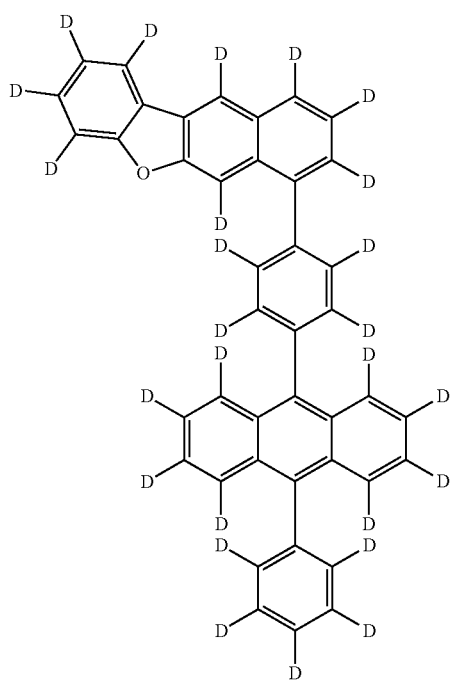

117
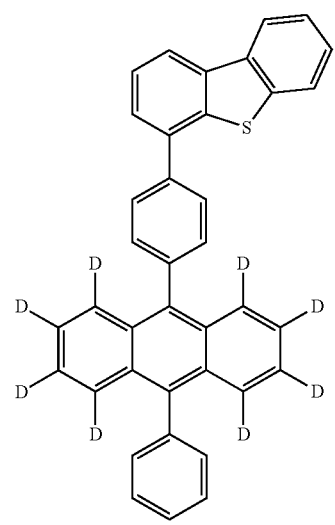
118
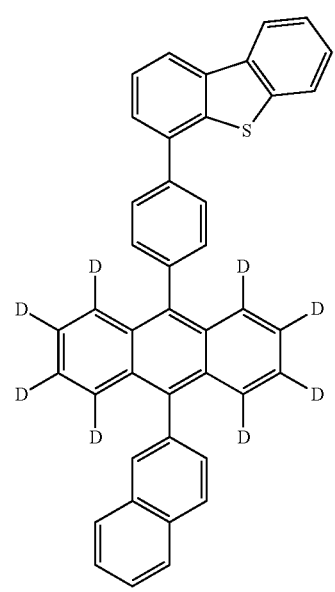
119
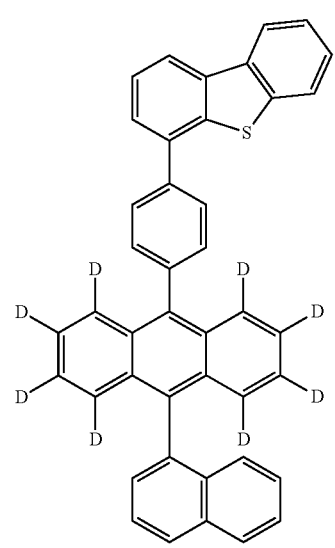
120
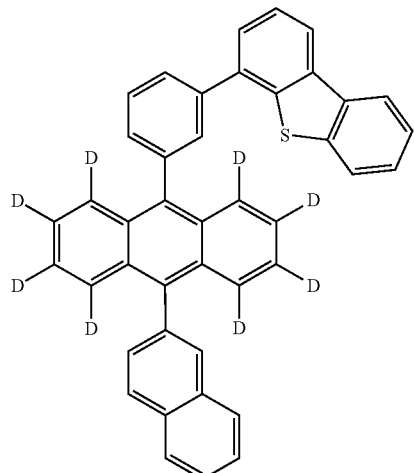
121
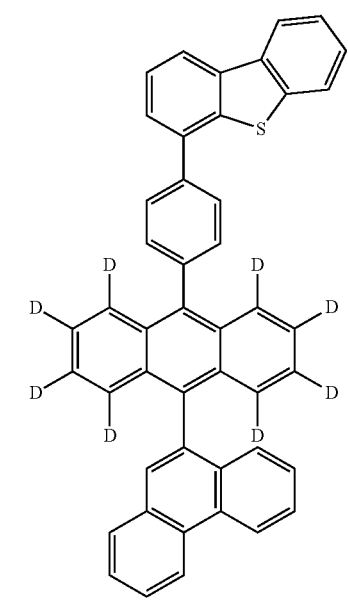

125
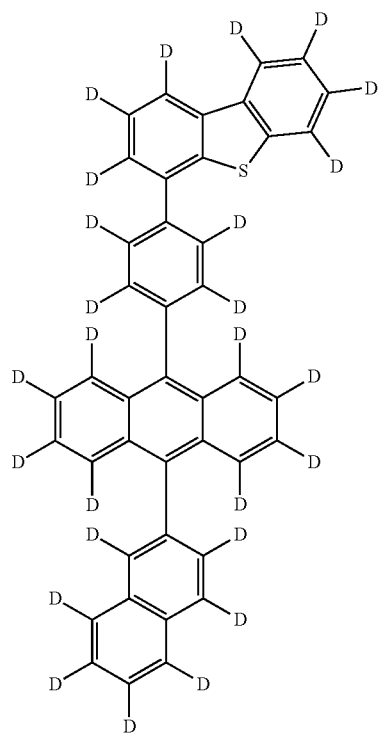
126
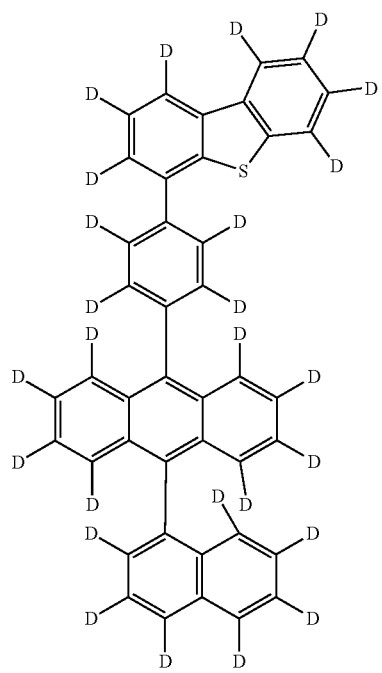
133
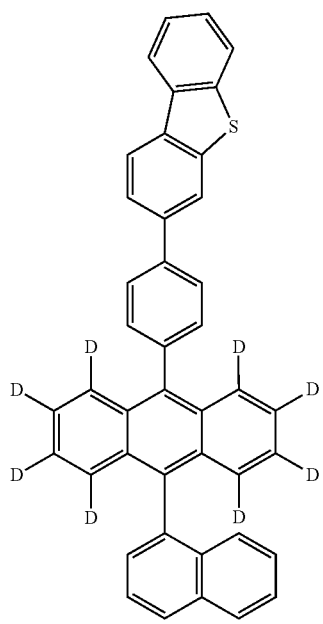
138
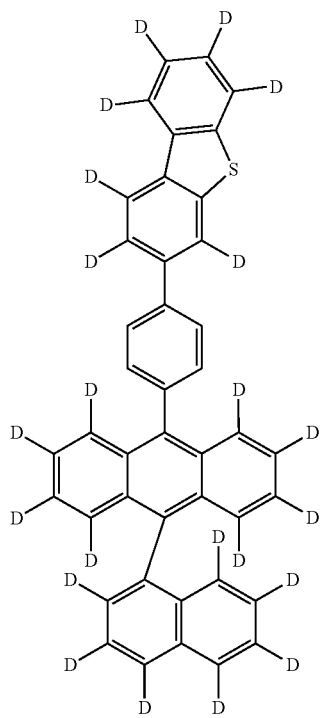

145
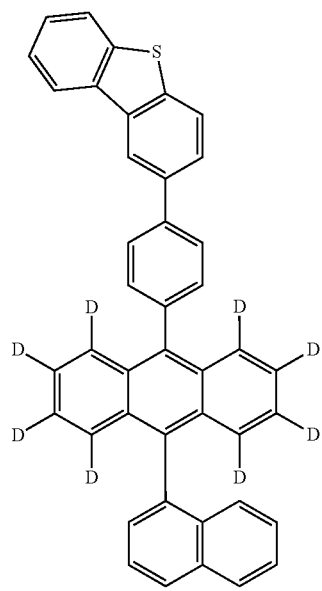
156
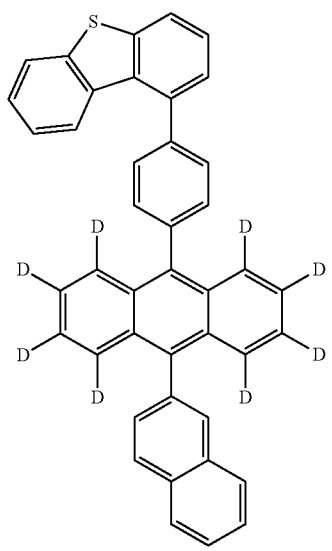
150
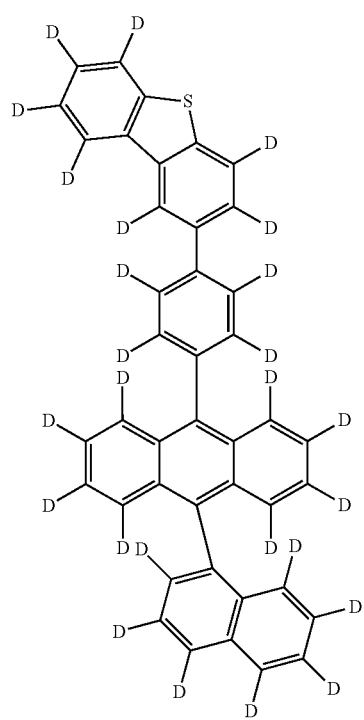
157
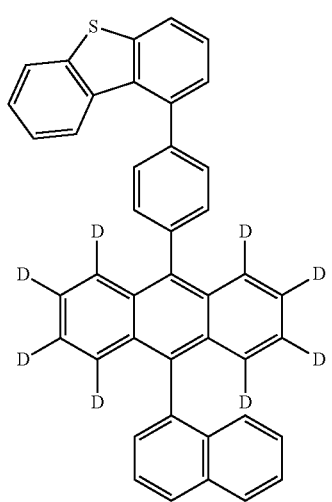

162
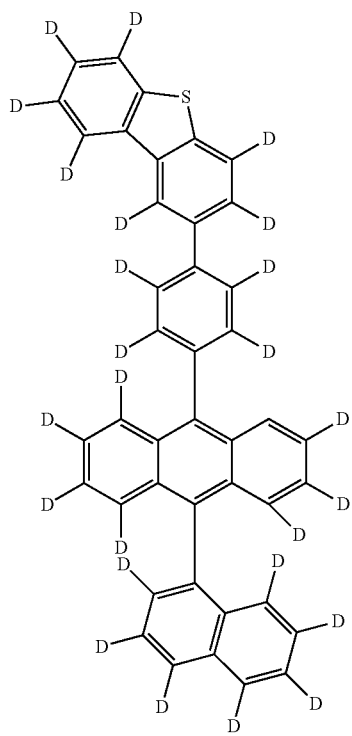
174
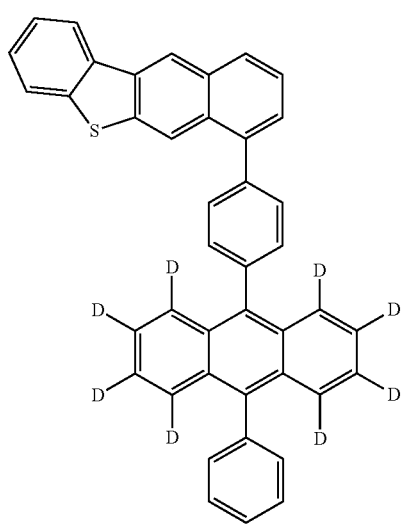
175
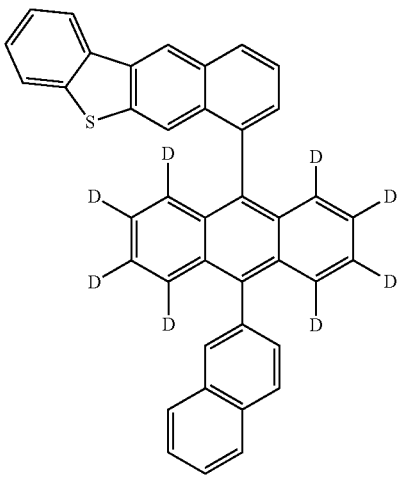
176
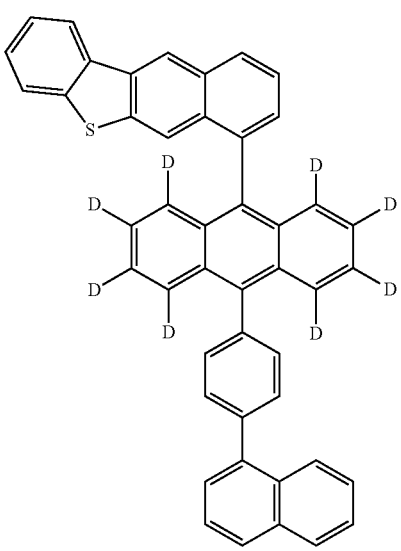
177
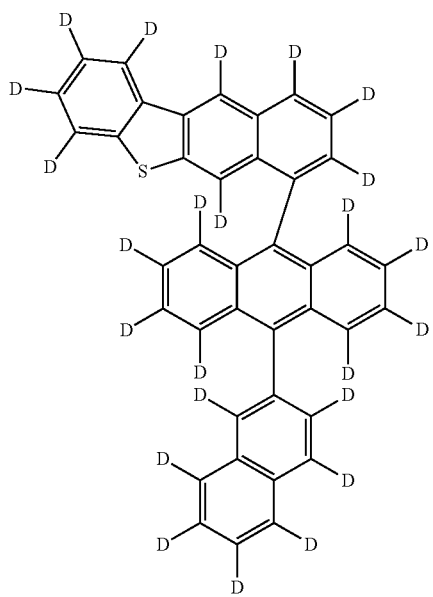

178
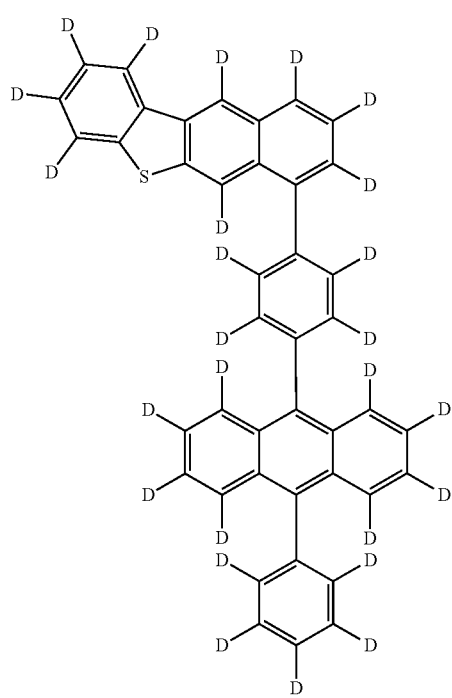
199
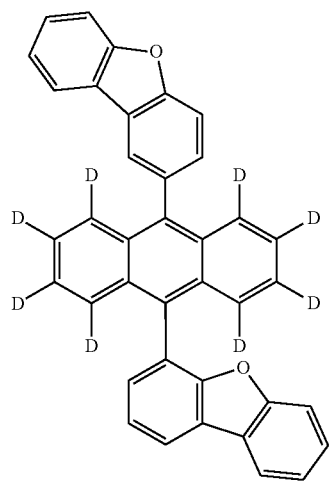
200
201
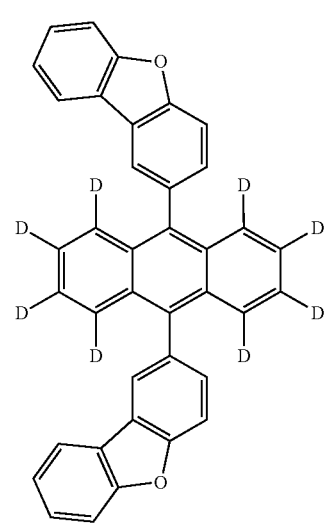
202
203
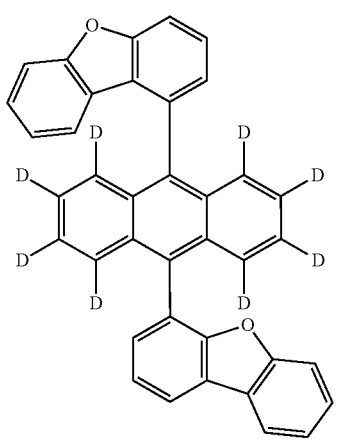

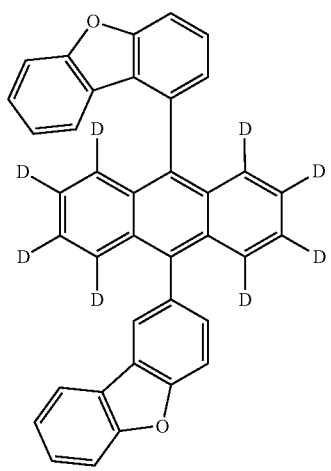

183
-continued
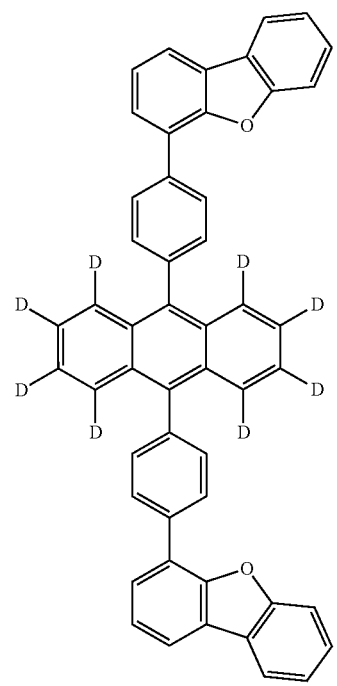
209
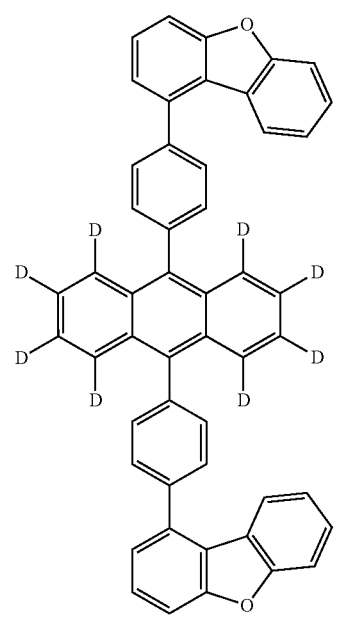
210
184
-continued
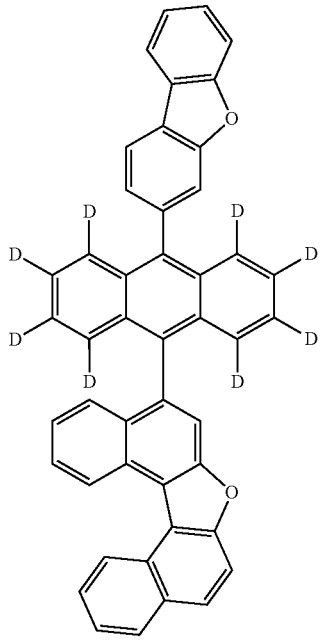
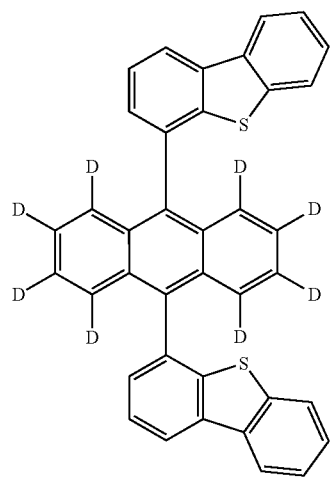
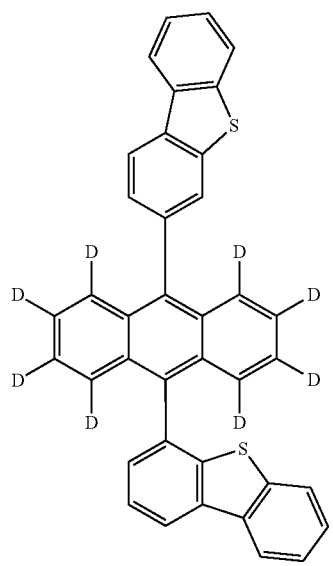
222

224
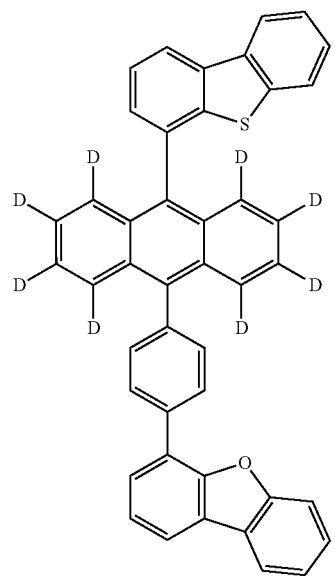
225
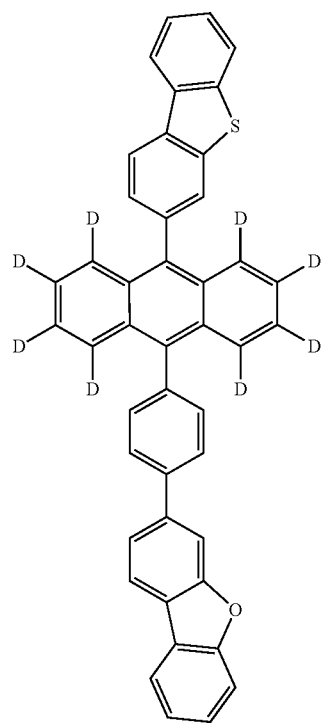
226
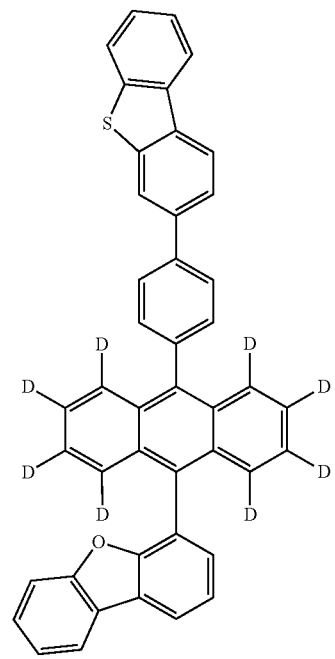
227
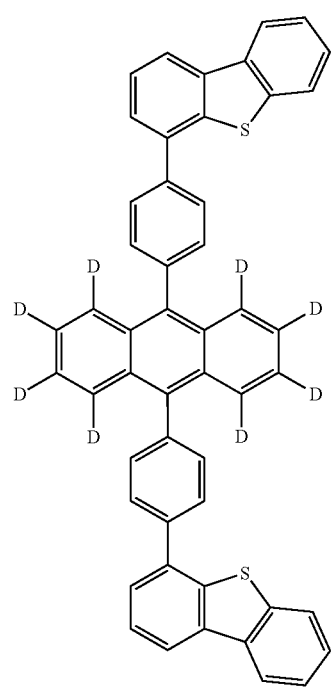

231
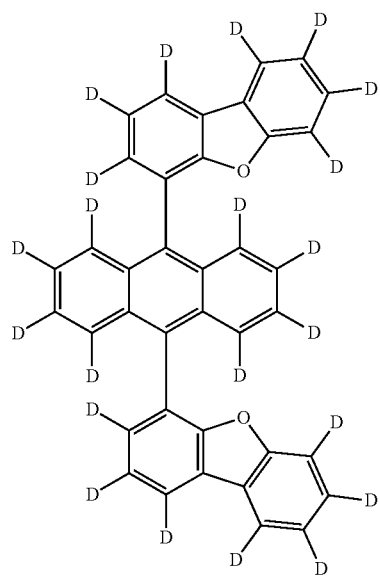
232
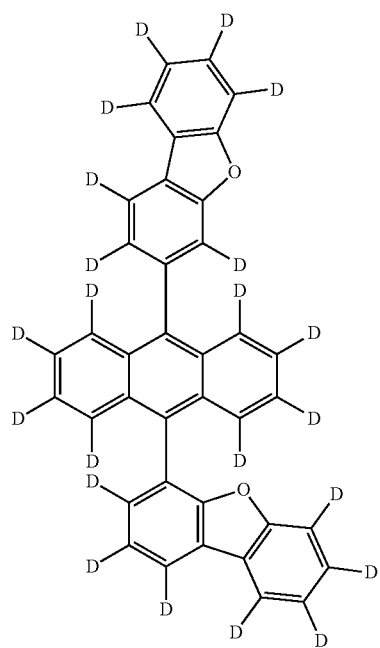
233
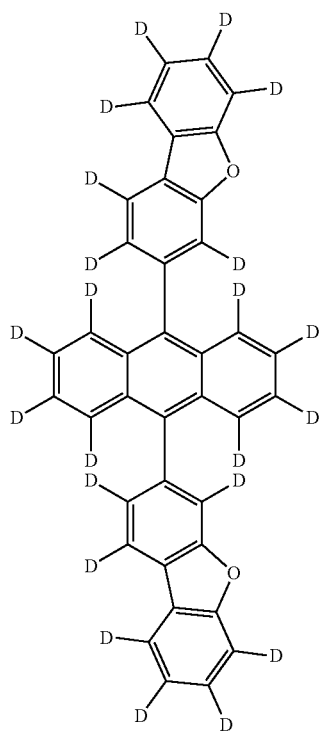
234
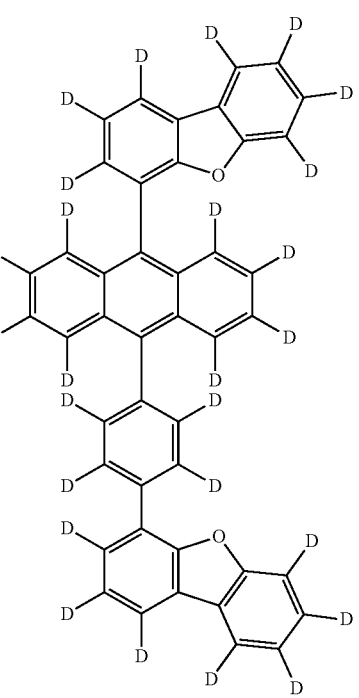

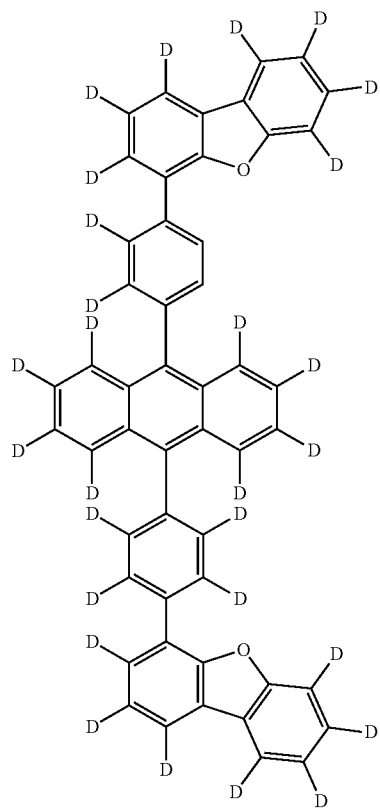
235
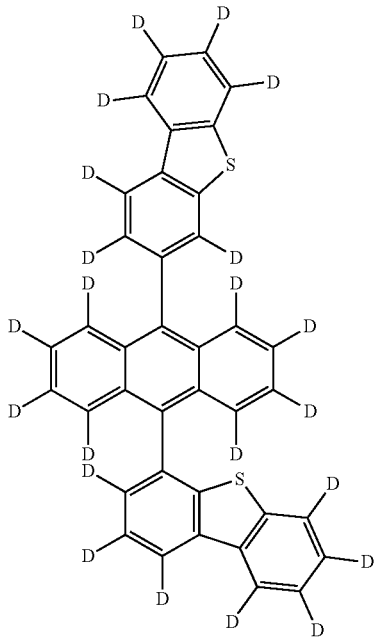
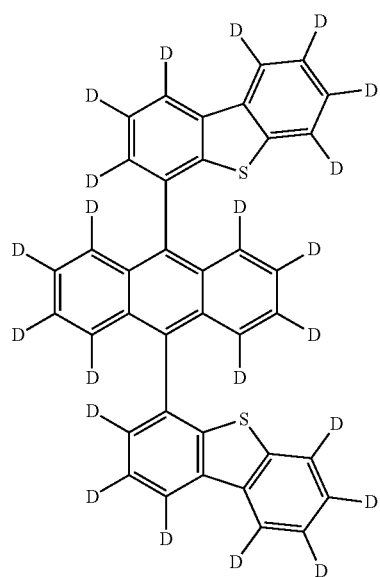
238
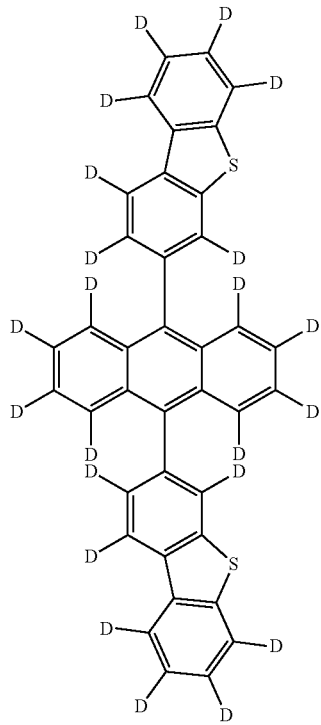

191
-continued

241

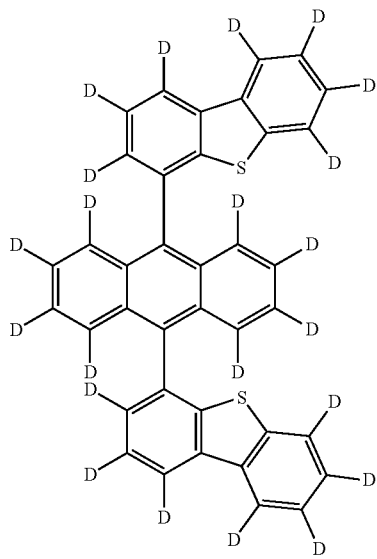

242

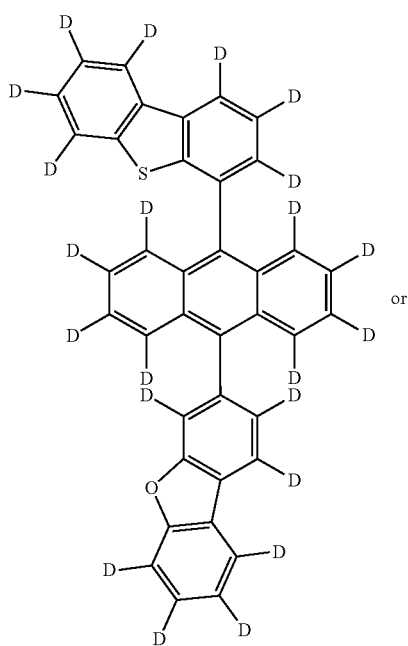

or

192
-continued

243

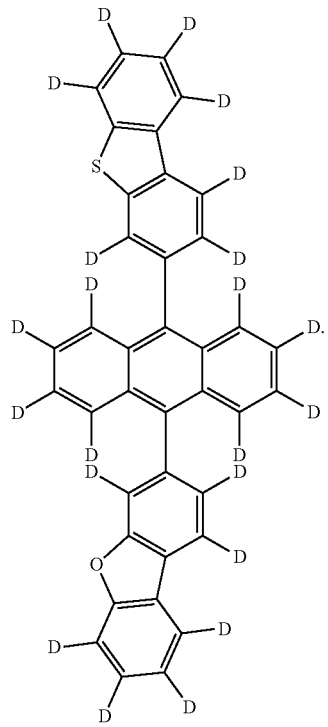

2. The organic electroluminescent device of claim 1, wherein the organic layer defines one selected from the group consisting of a hole-injecting layer, a hole-transporting layer, a light-emitting layer, a hole-blocking layer, an electron-transporting layer and an electron-injecting layer.

3. The organic electroluminescent device of claim 1, wherein the organic layer defines a light-emitting layer, wherein the light-emitting layer contains the compound selected from the structures of claim 1 as a host material.

4. An organic electroluminescent device, comprising:

a first light emission sub-stack for rendering first color light; and a second light emission sub-stack stacked on the first light emission sub-stack, wherein the second light emission sub-stack renders second color light, wherein at least one of the first light emission sub-stack and the second light emission sub-stack contains a host material, wherein the host material includes a compound selected from one of the following structures:

11
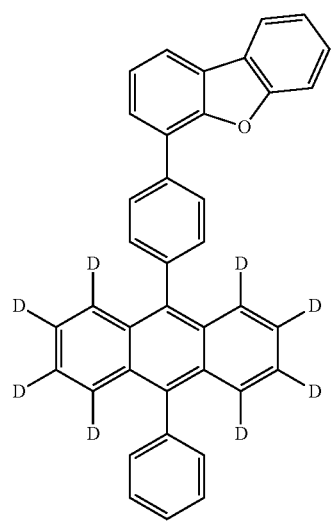
12
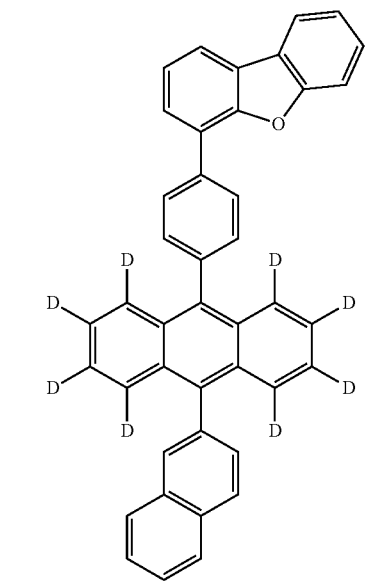
13
14
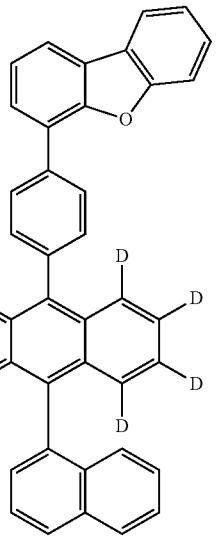
15
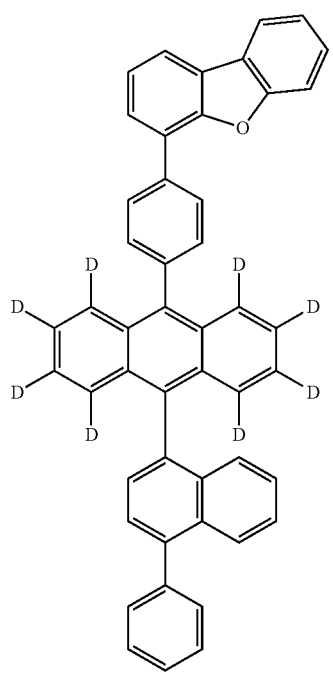

16
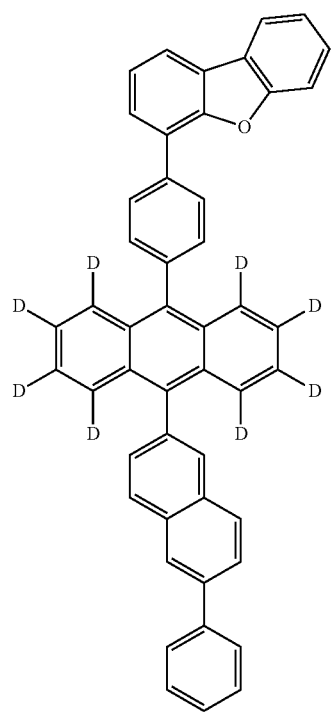
17
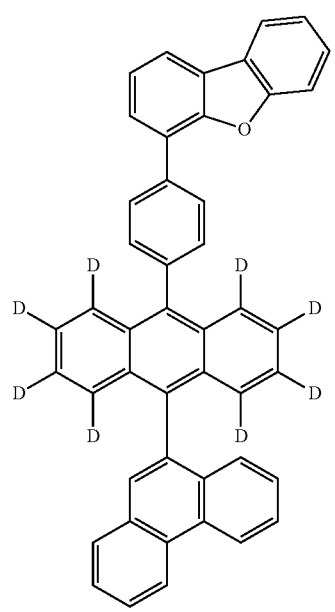
18
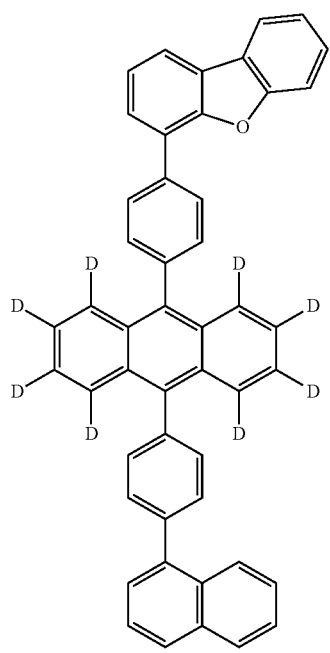
24
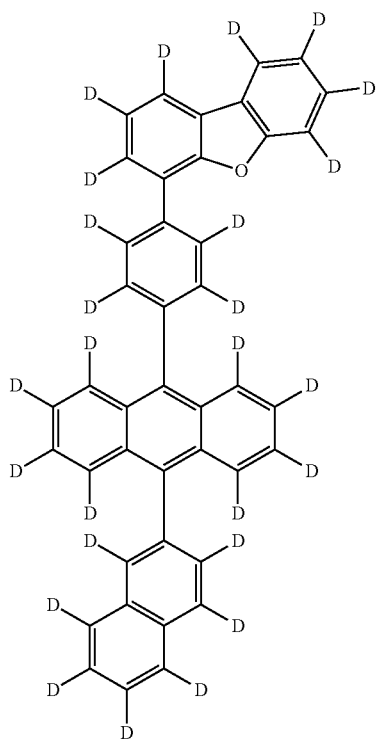

197
-continued
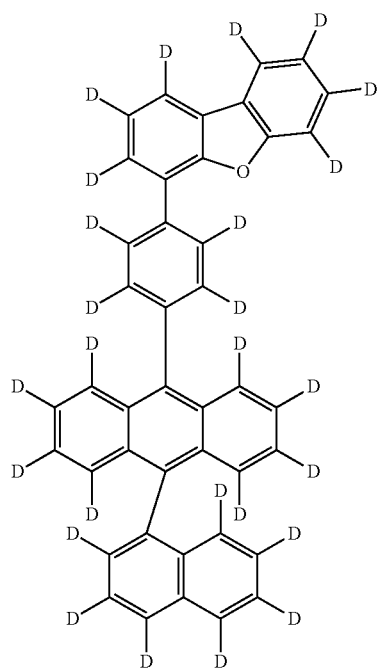
198
-continued
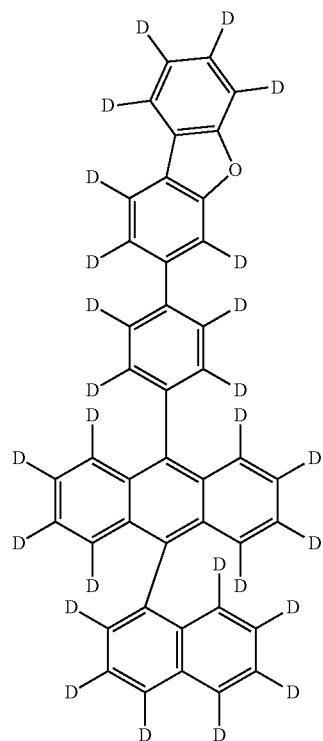
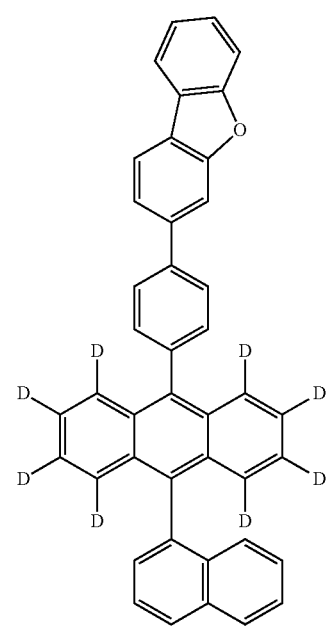
49
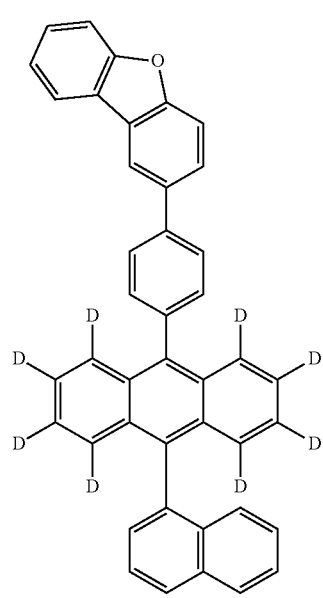

56
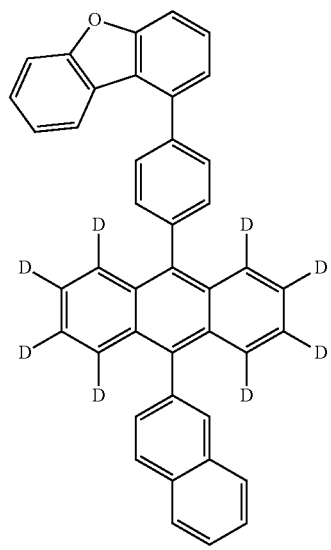
57
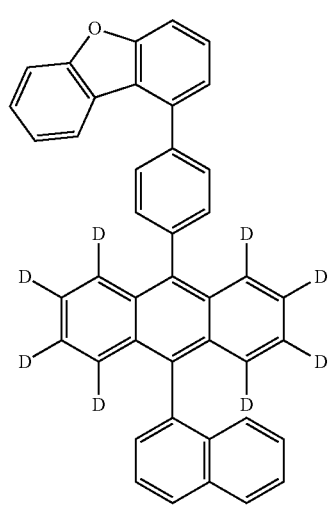
64
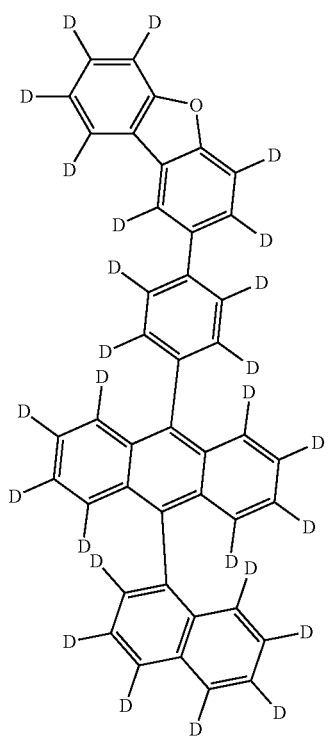
82
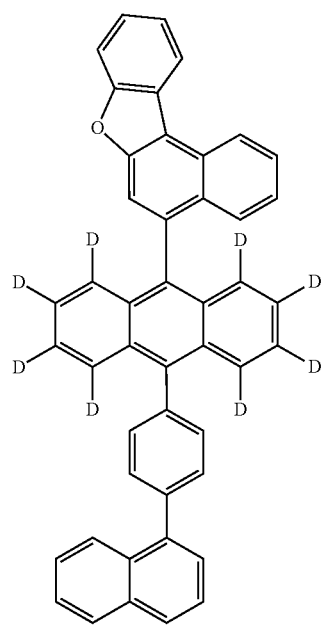

86
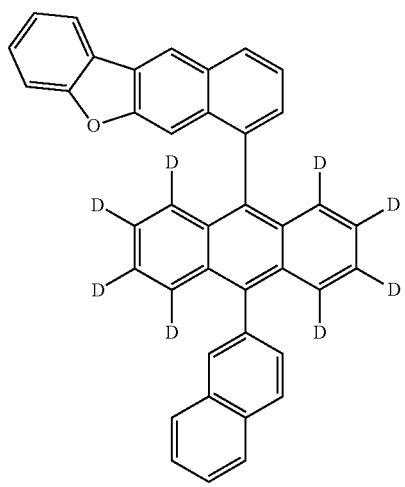
87
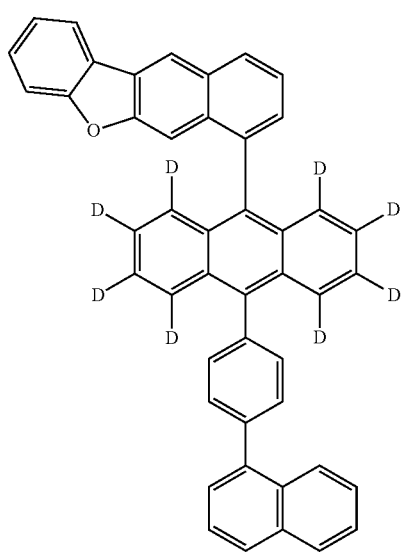
88
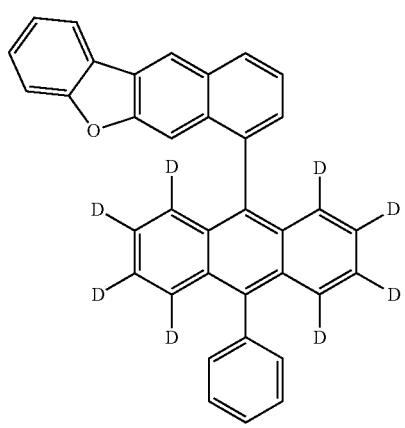
89
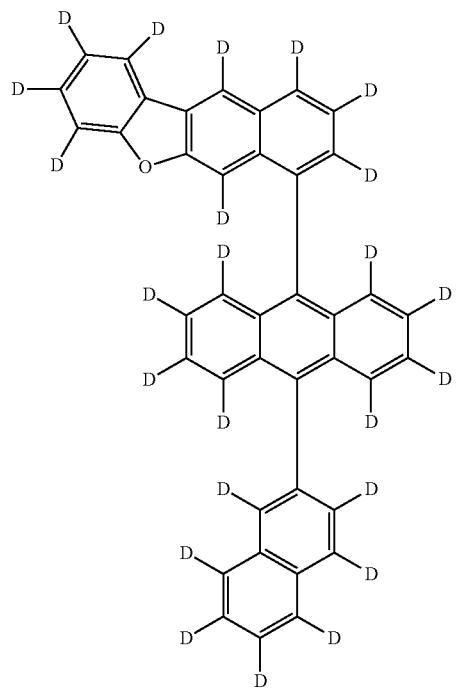
90
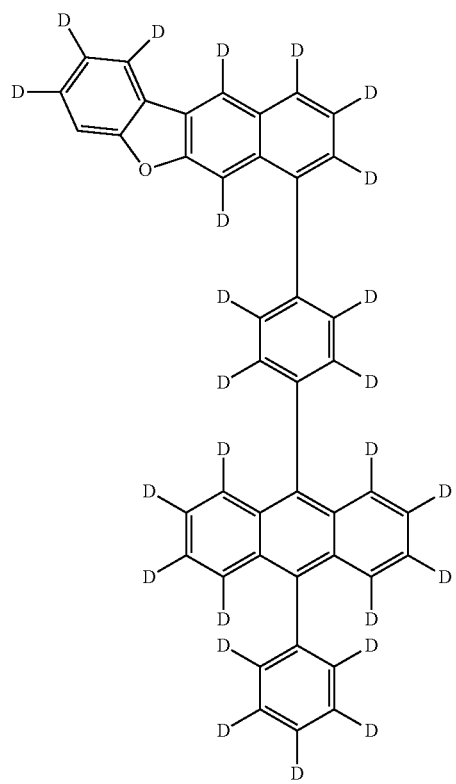

117
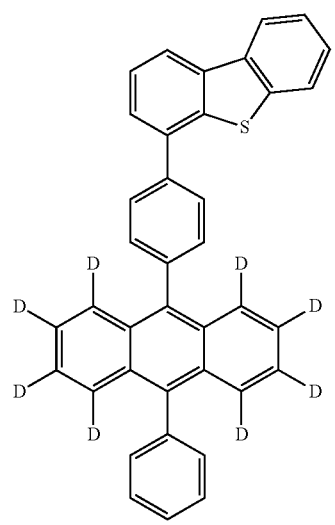
118
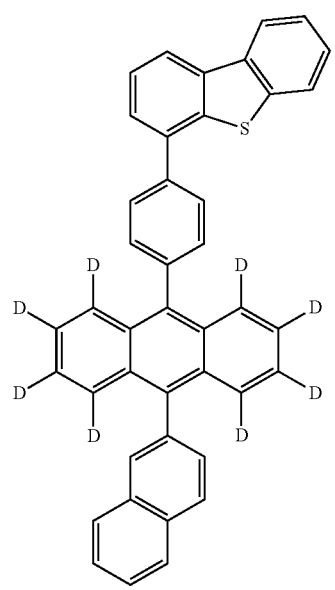
119
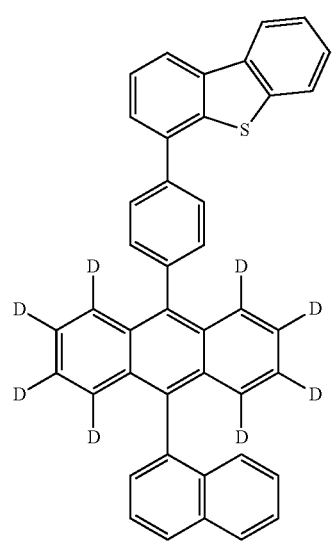
120
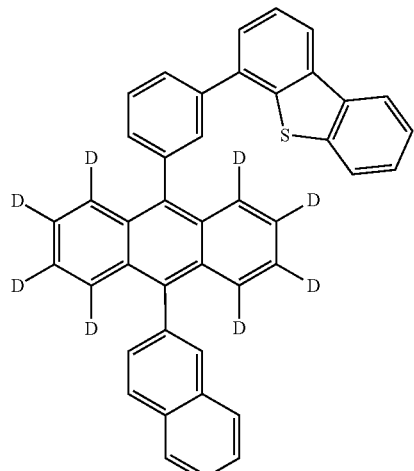
121
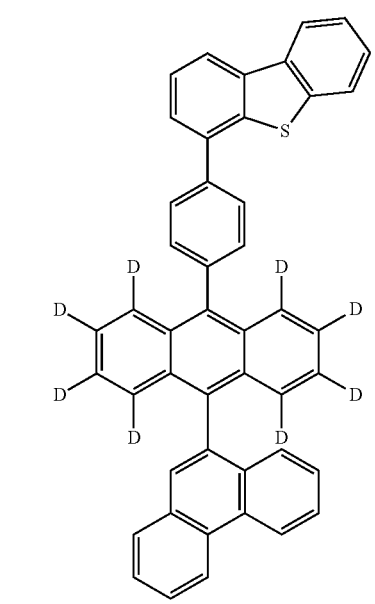

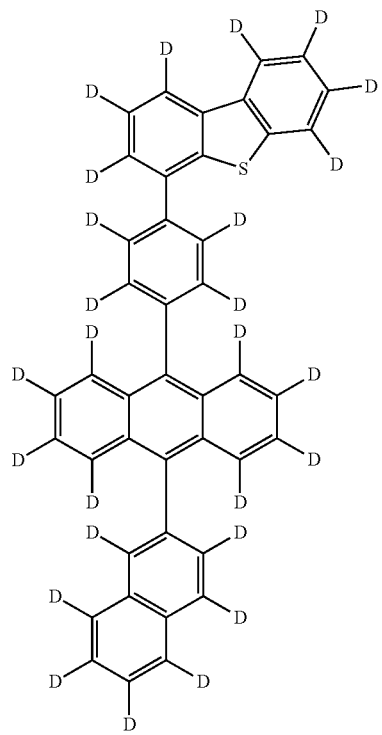

207
-continued
145
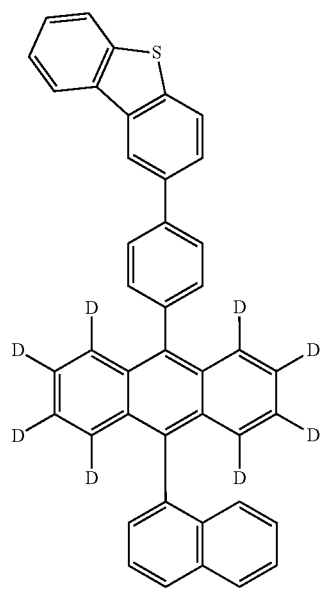
150
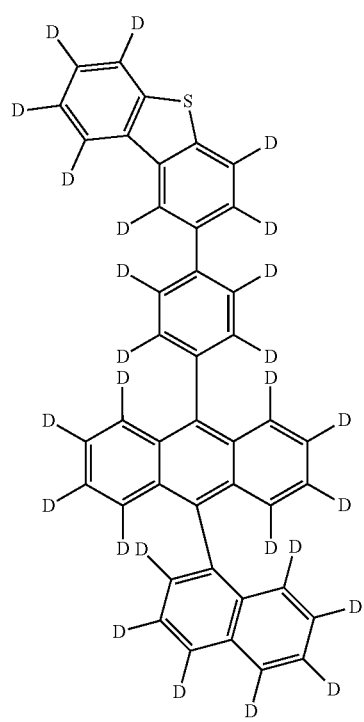
208
-continued
156
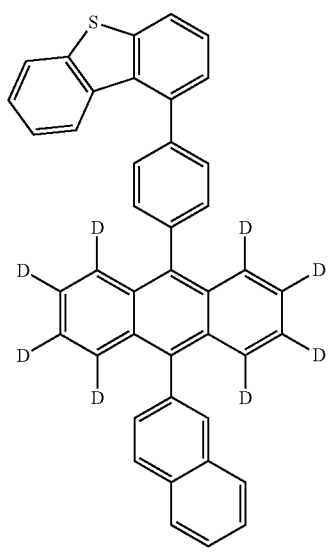
157
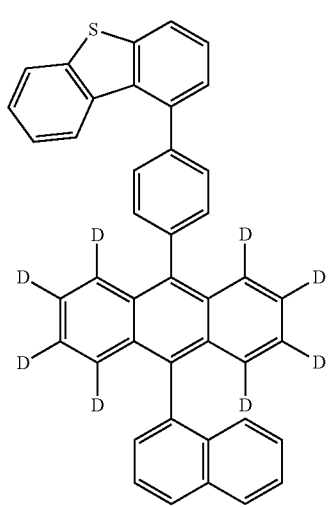

209
-continued
162
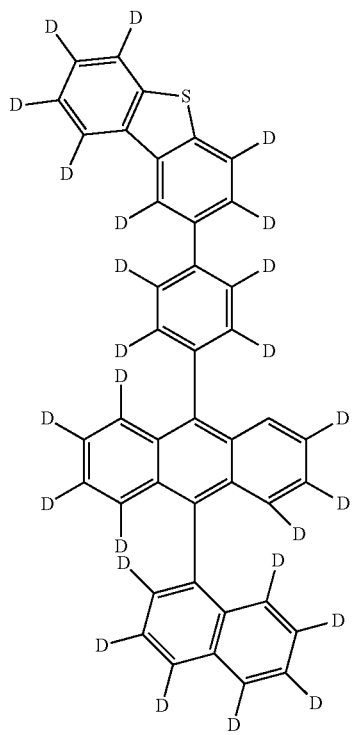
174
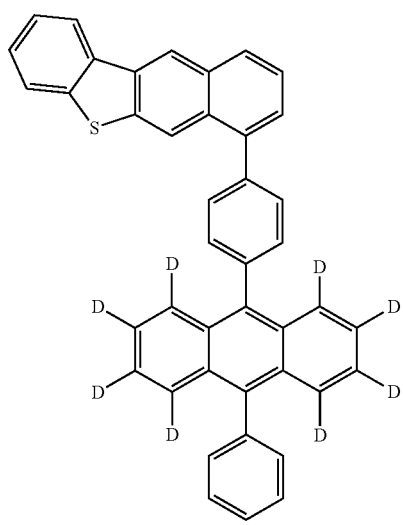
210
-continued
175
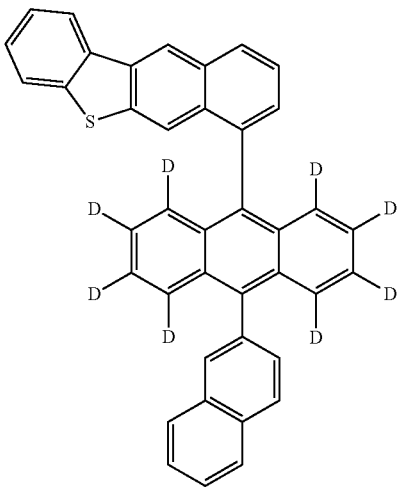
176
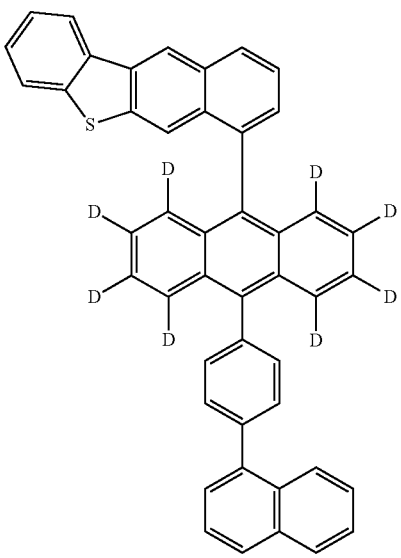
177
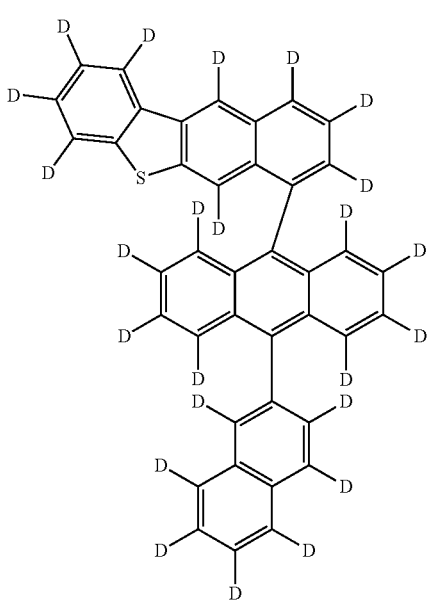

178
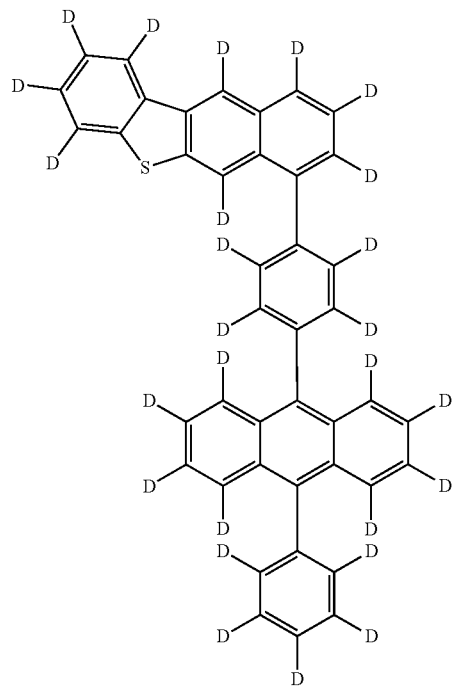
199
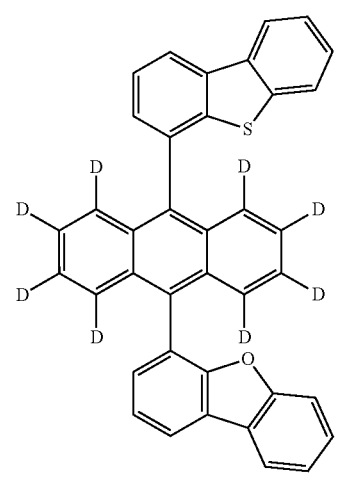
200
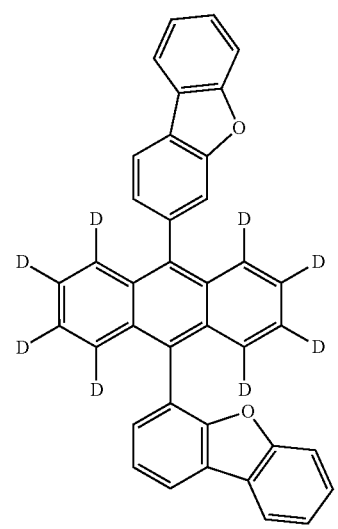
217
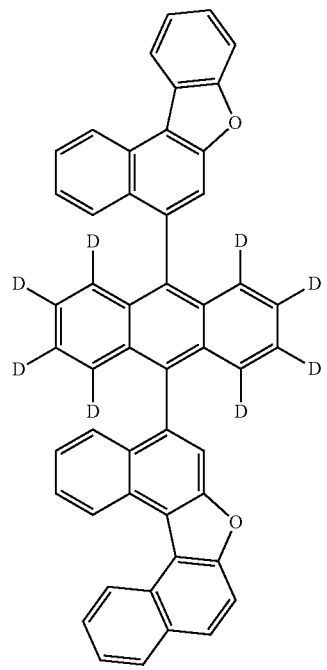
221
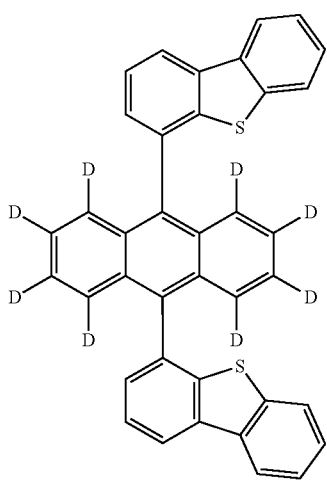
222
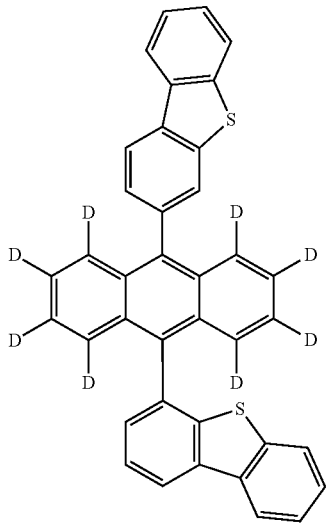

223
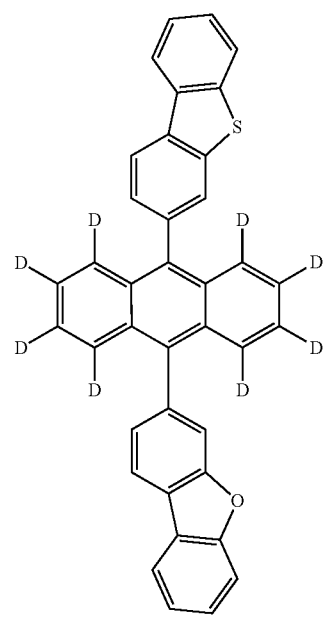
224
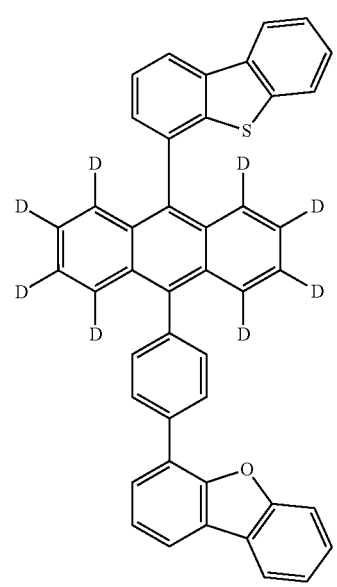
225
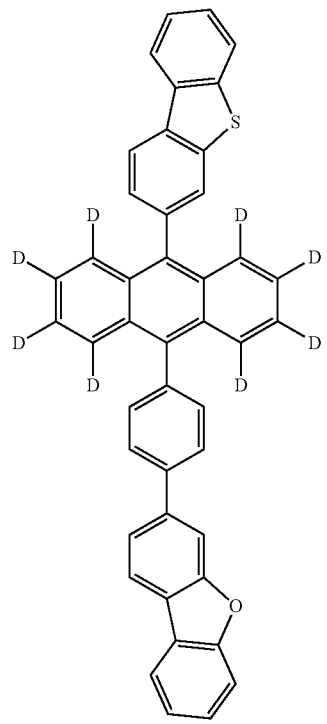
226
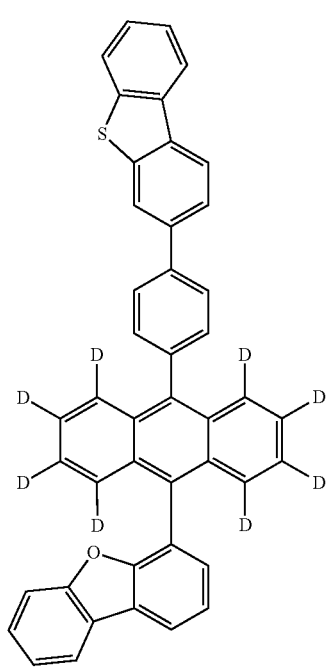

215
-continued
227
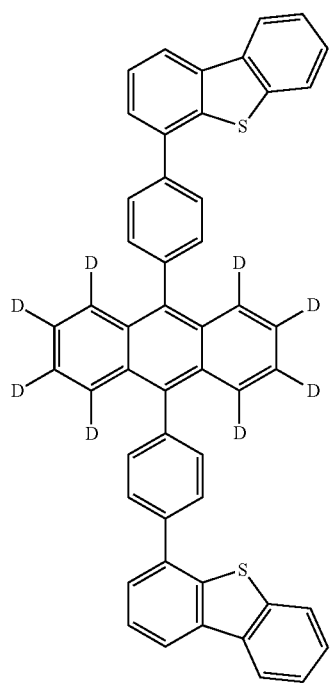
228
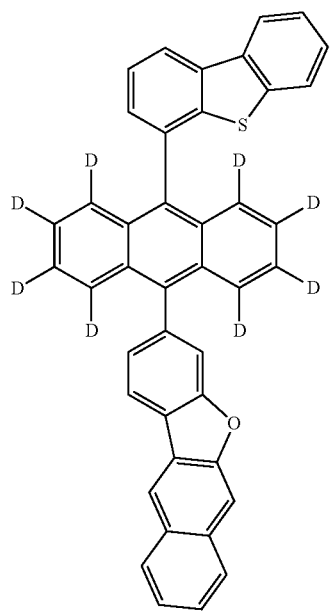
216
-continued
231
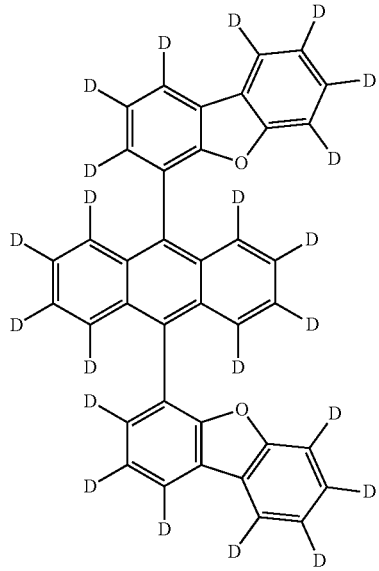
232
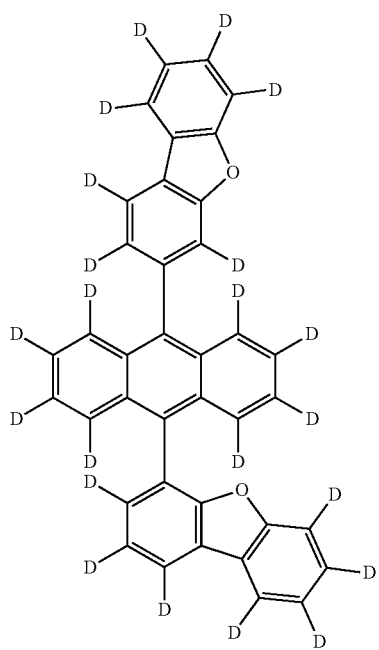

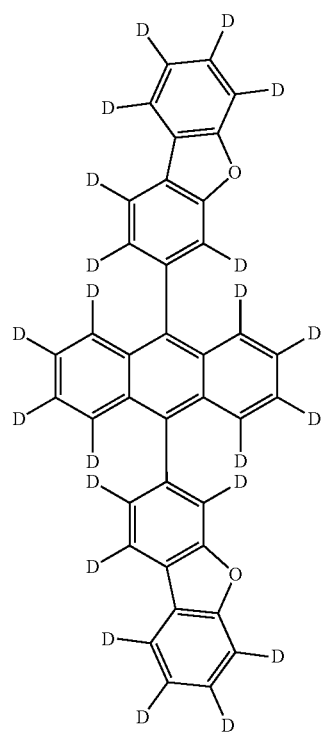

219
-continued
239
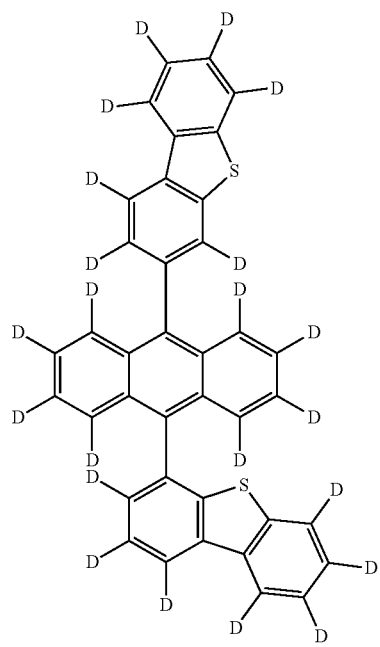
240
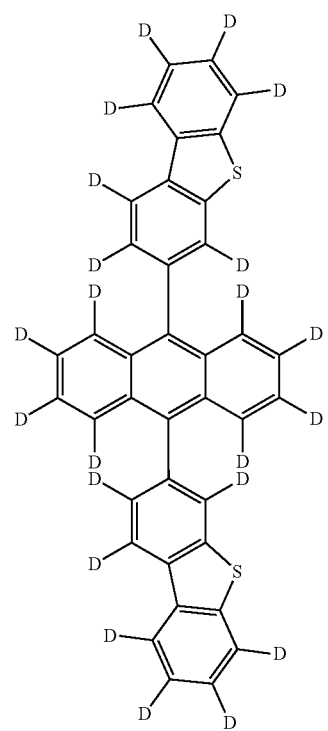
220
-continued
241
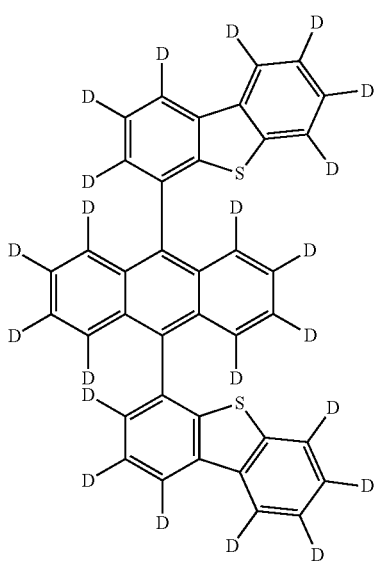
242
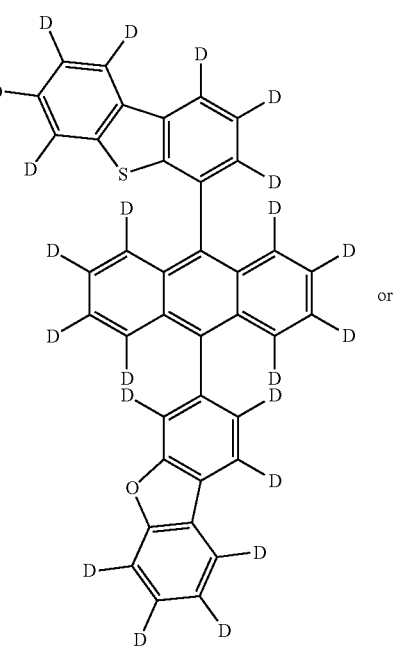
or -continued

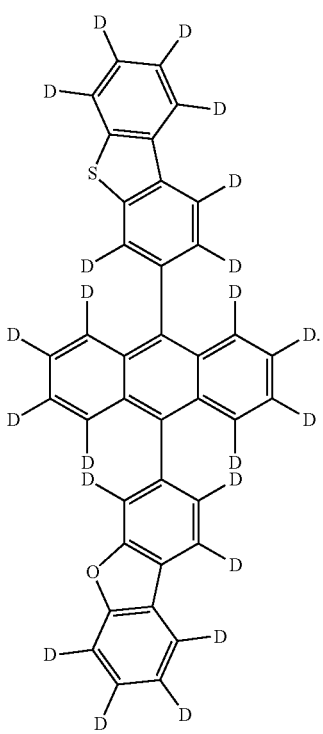

243

5. The organic electroluminescent device of claim 4, wherein the first light emission sub-stack includes a first light-emitting layer, wherein the second light emission sub-stack includes a second light-emitting layer, and wherein at least one of the first light-emitting layer and the second light-emitting layer contains the compound selected from the structures of claim 4 as the host material.

6. The organic electroluminescent device of claim 4, wherein the first light emission sub-stack includes a vertical sequential stack of a first electrode, a first hole-transporting layer, a first light-emitting layer and a first electron-transporting layer, wherein the second light emission sub-stack includes a vertical sequential stack of a second hole-transporting layer, a second light-emitting layer and a second electron-transporting layer, and wherein at least one of the first light-emitting layer and the second light-emitting layer contains the compound selected from the structures of claim 4 as the host material.

* * * * *

UNITED STATES PATENT AND TRADEMARK OFFICE
CERTIFICATE OF CORRECTION

Page 1 of 1

PATENT NO. : 11,342,505 B2
APPLICATION NO. : 16/366975
DATED : May 24, 2022
INVENTOR(S) : Seunghee Yoon et al.

It is certified that error appears in the above-identified patent and that said Letters Patent is hereby corrected as shown below:

On the Title Page

(72) Inventors:
Jin Sun Kim, Anyang-si (KR) should read: --Jin Sung Kim, Asan-si, (KR)--.

Signed and Sealed this
Sixteenth Day of July, 2024

Katherine Kelly Vidal
*Director of the United States Patent and Trademark Office*